(12) United States Patent
Elliman et al.

(10) Patent No.: US 11,903,997 B2
(45) Date of Patent: *Feb. 20, 2024

(54) MODULATORS OF SYNDECAN-2 AND USES THEREOF

(71) Applicant: Orbsen Therapeutics Limited, Galway (IE)

(72) Inventors: Stephen J. Elliman, Galway (IE); Laura Rose Barkley, Galway (IE); Jack Kavanaugh, Los Angeles, CA (US)

(73) Assignee: Orbsen Therapeutics Limited, Galway (IE)

( * ) Notice: Subject to any disclaimer, the term of this patent is extended or adjusted under 35 U.S.C. 154(b) by 1253 days.

This patent is subject to a terminal disclaimer.

(21) Appl. No.: 16/155,732

(22) Filed: Oct. 9, 2018

(65) Prior Publication Data

US 2019/0262421 A1 Aug. 29, 2019

Related U.S. Application Data

(63) Continuation of application No. 15/074,681, filed on Mar. 18, 2016, now Pat. No. 10,124,038.

(30) Foreign Application Priority Data

Mar. 20, 2015 (EP) .................. 15160181

(51) Int. Cl.
| | | |
|---|---|---|
| *A61K 38/17* | (2006.01) | |
| *A61K 9/08* | (2006.01) | |
| *A61K 9/00* | (2006.01) | |
| *A61K 35/545* | (2015.01) | |
| *A61K 35/17* | (2015.01) | |
| *C07K 16/28* | (2006.01) | |

(52) U.S. Cl.
CPC .......... *A61K 38/177* (2013.01); *A61K 9/0019* (2013.01); *A61K 9/08* (2013.01); *A61K 35/17* (2013.01); *A61K 35/545* (2013.01); *C07K 16/2896* (2013.01); *C07K 2317/76* (2013.01)

(58) Field of Classification Search
CPC ............ C07K 2319/30; C07K 2319/32; C07K 2319/33; C07K 2319/70; C07K 2319/73; C07K 2319/74
See application file for complete search history.

(56) References Cited

U.S. PATENT DOCUMENTS

| | | |
|---|---|---|
| 5,486,359 A | 1/1996 | Caplan et al. |
| 5,726,058 A | 3/1998 | Jalkanen et al. |
| 6,355,239 B1 | 3/2002 | Bruder et al. |
| 6,531,295 B1 | 3/2003 | Saunders et al. |
| 10,124,038 B2 | 11/2018 | Elliman |
| 10,920,197 B2 | 2/2021 | Elliman |
| 11,026,994 B2 | 6/2021 | Elliman |
| 2003/0100492 A1* | 5/2003 | Yayon ................ C07K 16/2896 530/397 |
| 2003/0225018 A1 | 12/2003 | Ekker et al. |
| 2004/0258670 A1 | 12/2004 | Laughlin et al. |
| 2005/0059147 A1 | 3/2005 | Seshi |
| 2005/0226864 A1 | 10/2005 | Hinton et al. |
| 2006/0078993 A1 | 4/2006 | Phan et al. |
| 2007/0264239 A1 | 11/2007 | Huard et al. |
| 2008/0241246 A1 | 10/2008 | Sakthivel et al. |
| 2010/0172885 A1 | 7/2010 | Pittenger et al. |
| 2010/0196329 A1 | 8/2010 | Ra et al. |
| 2010/0247577 A1 | 9/2010 | Foussat et al. |
| 2012/0122789 A1* | 5/2012 | Virag .................. A61K 38/177 514/16.4 |
| 2014/0356398 A1 | 12/2014 | Riddell et al. |
| 2015/0030615 A1 | 1/2015 | Derr et al. |
| 2016/0215265 A1 | 7/2016 | Elliman |
| 2019/0015331 A1 | 1/2019 | Elliman et al. |
| 2020/0158725 A1 | 5/2020 | Singh et al. |

FOREIGN PATENT DOCUMENTS

| | | |
|---|---|---|
| CN | 1678734 A | 10/2005 |
| EP | 1795588 A1 | 6/2007 |
| EP | 2545928 A1 | 1/2013 |
| EP | 3416964 A4 | 9/2019 |
| JP | 2016516797 A | 6/2016 |
| JP | 2017532965 A | 11/2017 |
| KR | 20080075959 A | 8/2008 |
| KR | 20100106744 A | 10/2010 |
| KR | 20120013915 A | 2/2012 |
| KR | 101309910 B1 | 9/2013 |
| WO | WO-02087609 A1 | 11/2002 |
| WO | WO-03046141 A2 | 6/2003 |
| WO | WO-03062386 A2 | 7/2003 |
| WO | WO-2004003179 A1 | 1/2004 |

(Continued)

OTHER PUBLICATIONS

Li et al (PLoS One, 2015, vol. 10, No. 2, e0118391, 16 pages) (Year: 2015).*
Shibui et al (Cytokine, 2012, vol. 59, pp. 108-114) (Year: 2012).*
Jafarzadeh et al (Anatolian Journal of Cardiology/Anadolu Kardiyoloji Dergisi, 2009, vol. 9, No. 2, pp. 75-83) (Year: 2009).*
Williams and Hennekens (Expert Opinion in Pharmacotherapeutics, 2004, vol. 5, pp. 109-115) (Year: 2004).*
Green (Clinical Cornerstone, 2001, vol. 3, pp. 50-59) (Year: 2001).*
Brand (Gut, 2009, vol. 58, pp. 1152-1167) (Year: 2009).*
Colombel et al (Inflammatory Bowel Disease, 2009, vol. 15, pp. 1308-1319) (Year: 2009).*

(Continued)

*Primary Examiner* — Karen A. Canella
(74) *Attorney, Agent, or Firm* — Wilson Sonsini Goodrich & Rosati

(57) ABSTRACT

Modulators of syndecan-2, such as an antibody to syndecan-2 that cross-links syndecan-2 on the cell surface or a syndiecan-2 polypeptide that interferes with syndecan-2 receptor binding, is used to regulate a Th17 mediated disease such as an autoimmune disease, fibrosis or cancer.

9 Claims, 17 Drawing Sheets

Specification includes a Sequence Listing.

(56) References Cited

FOREIGN PATENT DOCUMENTS

| WO | WO-2008100083 A1 | 8/2008 |
| --- | --- | --- |
| WO | WO-2009012357 A2 | 1/2009 |
| WO | WO-2009105624 A2 | 8/2009 |
| WO | WO-2010065239 A1 | 6/2010 |
| WO | WO-2011153458 A2 | 12/2011 |
| WO | WO-2012111997 A2 | 8/2012 |
| WO | WO-2013117761 A1 | 8/2013 |
| WO | WO-2013172793 A1 | 11/2013 |
| WO | WO-2014168548 A2 | 10/2014 |
| WO | WO-2014170411 A1 | 10/2014 |
| WO | WO-2015038075 A1 | 3/2015 |
| WO | WO-2017141116 | 8/2017 |
| WO | WO-2018220442 A2 | 12/2018 |
| WO | WO-2020035741 A2 | 2/2020 |

OTHER PUBLICATIONS

The abstract of Desreumax et al (Gastroenterology, 2012, vol. 143, pp. 1207-1217) (Year: 2012).*
Kelsen et al (Clinical and Experimental Immunology, 2005, vol. 141, pp. 549-557) (Year: 2005).*
NCBI (GenPept, UniProtKB/Swiss-Prot, Accession No. P34741) (Year: 2022).*
UniProtKB Accession No. #P34741 (Aug. 21, 2007). (Year: 2007).*
Brazilian Patent Application No. 112015026258-9 Search Report dated Oct. 29, 2019.
Canadian Patent Application No. 2,909,356 Office Action dated Mar. 3, 2020.
Davey et al.: Mesenchymal stem cell-based treatment for microvascular and secondary complications of diabetes mellitus. Frontiers in Endocrinology 5:86 [1-16]. doi: 10.3389/fendo.2014.00086 (2014).
Final Report Summary—Reddstar (Repair of Diabetic Damage by Stromal Cell Administration). European Commission https://cordis.europa.eu/result/rcn/197094_en.html 1-28 (2017).
Final Report Summary—Core of Report—Reddstar (Repair of Diabetic Damage by Stromal Cell Administration). European Commission https://cordis.europa.eu/docs/results/305/305736/final1-reddstar-final-report-core-of-report.pdf 1-44 (2017).
Hagymasi et al.: Stem cell treatment in the treatment of gastrointestinal diseases. Orvosi Hetilap. 149(31):1449-1455 (2008).
Japanese Patent Application No. 2017-550240 Office Action dated Mar. 2, 2020.
Mendez-Ferrer et al.: Mesenchymal and haematopoietic stem cells form a unique bone marrow niche. Nature, 466:829-836 (2010).
Mendez-Ferrer et al.: Mesenchymal and haematopoietic stem cells form a unique bone marrow niche Nature, 466:829-836 (2010) Supplementary Information, 21 pages.
Patil et al.: Enhancement of wound healing with increased angiogenesis in a diabetic rabbit ulcer model by topical application of CD362+ human mesenchymal stem cells (Cyndacel-M) seeded in Excellagen scaffold. Tissue Engineering Part A, 21(Supp. 1):S90 XP05509717 (2015).
PCT/IB2018/000687 International Search Report and Written Opinion dated May 12, 2018.
U.S. Appl. No. 16/009,048 Office Action dated Dec. 13, 2019.
U.S. Appl. No. 16/254,378 Office Action dated Apr. 16, 2020.
Alvarez-Viejo, Maria: CD271 as a marker to identify mesenchymal stem cells from diverse sources before culture. World Journal of Stem Cells, vol. 7, No. 2, Jan. 1, 2015, p. 470.
Carlotti, Francoise, et al., "Isolated human islets contain a distinct population of mesenchymal stem cells," Islets, p. 164-173 May/Jun. 2010.
Chinese Patent Application No. 201380019351.0 Third Office Action dated Jan. 12, 2017.
Christianson and Belting, Heparan sulfate proteoglycan as a cell-surface endocytosis receptor. Matrix Biology, 35:51-55, 2014.
Chung et al., "Human Embryonic Stem Cell Lines Generated without Embryo Destruction." Cell Stem Cell, vol. 2, No. 2, 2008, pp. 113-117.
Chinese Patent Application No. 201480025184.5 Office Action dated Jul. 4, 2018.
Costabel et al., Pirfenidone in idiopathic pulmonary fibrosis: Expert panel discussion on the management of drug-related adverse events. Adv. Ther., 31:375-391, 2014.
Cuthbert et al., "Single-platform quality control assay to quantify multipotential stromal cells in bone marrow aspirates prior to bulk manufacture or direct therapeutic use." Cytotherapy, 2012, vol. 14, No. 4, pp. 431-440.
Dieudonne et al. High Wnt signaling represses the proapoptotic proteoglycan syndecan-2 in osteosarcoma cells. Cancer Res 70(13):5399-5408 (2010).
Duffy et al., Mesenchymal stem cell inhibition of T-helper 17 cell-differentiation is triggered by cell-cell contact and mediated by prostaglandin E2 via the EP4 receptor. European Journal of Immunol., 41:2840-2851, 2011.
European Patent Application No. 14718403.0 Communication dated Apr. 6, 2017.
European Patent Application No. 14718403.0 Communication dated Mar. 6, 2018.
European Patent Application No. 14718403.0 Examination Report dated Jan. 2, 2019.
European Patent Application No. 15158384.6 Communication dated Apr. 7, 2017.
European Patent Application No. 15158384.6 Extended European Search Report dated Jul. 8, 2015, 10 pages.
European Patent Application No. 18190005.1 European Search Report dated May 3, 2019.
GB1202319.8 Search Report dated Jun. 11, 2012, 3 pages.
Gronthos et al. "Molecular and cellular characterisation of highly purified stromal stem cells derived from human bone marrow." (2003) Journal of Cell Science, vol. 116:1827-1835.
Hohki et al., Blockade of interleukin-6 signaling suppresses experimental autoimmune uveoretinitis by the inhibition of inflammatory Th17 responses. Experimental Eye Research, 91:162-170, 2010.
Horwitz et al., Clarification of the nomenclature for MSC: The international society for cellular therapy position statement. Cytotherapy, 7:393-395, 2005.
Hsu et al. Neural stem cells, neural progenitors, and neurotrophic factors. Cell Transplant 16(2):133-150 (2007).
Huang et al., Prognostic significance of altered expression of SDC2 and CYR61 in esophageal squamous cell carcinoma. Oncology Reports, 21:1123-1129, 2009.
"Human/Mouse Integrin [alpha]11 Antibody." Jun. 30, 2015 (Jun. 30, 2015), 1 page, Retrieved from the Internet: URL:http://www.rndsystems.com/pdf/MAB4235.pdf.
Indian Patent Application No. 1777/KOLNP/2014 Office Action dated May 31, 2018.
International Patent Application No. PCT/IB2018/000687 International Search Report and Written Opinion dated Dec. 5, 2018.
International Patent Application No. PCT/IB2018/000939 International Search Report and Written Opinion dated Dec. 19, 2018.
Jones, E., et al., "Large-Scale Extraction and Characterization of CD271+ Multipotential Stromal Cells From Bone in Health and Osteoarthritis," Arthritis & Rhuematism, vol. 62, No. 7, Jul. 2010, pp. 1944-1954.
Kaltz N et al: Novel markers of mesenchymal stem cells defined by genome-wide gene expression analysis of stromal cells from different sources. Experimental Cell Research, Academic Press, US, vol. 316, No. 16, (Oct. 1, 2010), pp. 2609-2617.
Keifer et al.: "Inhibition of NF-ĕB Activity by Thalidomide through Suppression of IĕB Kinase Activity", Journal of Biological Chemistry, American Society for Biochemistry and Molecular Biology, US, vol. 276, No. 25, Jun. 22, 2001, pp. 22382-22387.
Khan et al., CD4+ T Cell-derived Novel Peptide Thp5 Induces Interleukin-4 Production in CD4+ T Cells to Direct T Helper 2 Cell Differentiation. J Biol Chem, 287, 2830-2835, 2011.
Kozanoglu, Ilknur, et al., "Human bone marrow mesenchymal cells express NG2: possible increase in discriminative ability of flow cytometry during mesenchymal stromal cell identification." Cytotherapy (2009) vol. 11, No. 5, pp. 527-533.
KR1317507 Abstract from STN CAPlus database (1 pg) (2015).

(56) References Cited

OTHER PUBLICATIONS

Lambaerts et al., The signalling mechanisms of syndecan heparen sulphate proteoglycans Current Opinion Cell Biol., 21(5):662-669 (2009).
Lim et al., Cell surface heparan sulfate proteoglycans control adhesion and invasion of breast carcinoma cells Molecular Cancer, 14:15, 18 pages, 2015.
Lim et al., Syndecan-2 regulation of morphology in breast carcinoma cells is dependent on RhoGTPases. Biochimica et Biophysica Acta, 1840:2482-2490, 2014.
Llinas, L, et al., "Expression profiles of novel cell surface molecules on B-cell subsets and plasma cells as analyzed flow cytometry," Immunology Letters, vol. 134, No. 2, Jan. 30, 2011, pp. 113-121.
Lyons and Parish, Determination of lymphocyte division by flow cytometry. Journal of Immunological Methods, 171:131-137, 1994.
Manon-Jensen et al., Proteoglycans in health and disease: the multiple roles of syndecan shedding FEBS Journal, 277(19):3876-3889, 2010.
Matesanz-Isabel et al., New B-cell CD molecules. Immunology Letters, 2011, vol. 134, No. 2, pp. 104-112.
Mytilinalou et al., Research Communication: Syndecan-2 is a key regulator of transforming growth factor beta 2/Smad2-mediated adhesion in fibrosarcoma cells. IUBMB Life, 65(2): 134-143 (2013).
Nierhoff et al. New cell surface markers for murine fetal hepatic stem cells identified through high density complementary DNA microarrays. Hepatology 46(2):535-547 (2007).
Nish et al., T cell-intrinsic role of IL-6 signaling in primary and memory responses. Elife, 3:e01949, 21 page (2014).
Paris et al., Opposing Roles of Syndecan-1 and Syndecan-2 in Polyethyleneimine-mediated Gene Delivery. J Biol Chem, 283:7697-7704, 2008.
Parish, Fluorescent dyes for lymphocyte migration and proliferation studies. Immunology and Cell Biology, 77:499-508, 1999.
Park et al., Syndecan-2 mediates adhesion and proliferation of colon carcinoma cells. The Journal of Biological Chemistry, 277(33):29730-29736, 2002.
PCT Patent Application No. PCT/EP2016/056065 International Search Report and Written Opinion dated May 20, 2016.
PCT Patent Application No. PCT/US2016/023178 International Search Report and Written Opinion dated Jun. 13, 2016.
PCT/EP2013/052692 International Preliminary Report on Patentability under Chapter II completed Mar. 13, 2014.
PCT/EP2013/052692 International Search Report completed Jun. 10, 2013.
PCT/EP2013/052692 Written Opinion Report completed Jun. 10, 2013.
PCT/US2017/000091 International Search Report and Written Opinion dated May 12, 2017.
Pennock, Natahan D. et al. T cell response: naive to memory and everything in between. Adv. Physiol. Educ. 37:273-283 (2013).
Rovira-Clave, Xavier et al. Syndecan-2 can promote clearance of T-cell receptor/CD3 from the cell surface. Immunology, 137(3):214-225 (Nov. 2012):E-Pub: Oct. 2, 2012.
Rozemuller, H., et al., Prospective isolation of mesenchymal stem cells from multiple mammalian species using cross-reacting anti-human monoclonal antibodies. Stem Cells and Development, vol. 19, No. 12, Dec. 1, 2010, pp. 1911-1921.
Ruiz et al., Syndecan-2 is a novel target of insulin-like growth factor binding protein-3 and is over-expressed in fibrosis. Plos One, 7(8):1-4, 2012.
Russian Patent Application No. 2014136711 Official Action dated Feb. 23, 2017.
Sanz-Nogués et al.: Angiogenic assessment of Orbcel TM, a novel stromal cell population for treating Critical Limb Ischaemia (CLI); Cytotherapy, vol. 19, S198 (2017).
Sattler et al.: "Inhibition of T-Cell Proliferation by Murine Multipotent Mesenchymal Stromal Cells is Mediated by CD39 Expression and Adensoine Generation", Cell Transplantation, vol. 20, No. 8, Sep. 1, 2011, pp. 1221-1230.
Shi et al., Syndecan-2 exerts antifibrotic effects by promoting caveolin-1-mediated transforming growth factor-$\beta$ receptor I internalization and inhibiting transforming growth factor-$\beta$1 signaling. Am J Respir Crit Care Med, 188:831-841, 2013.
Si et al. CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Silva et al. "The Profile of Gene Expression of Human Marrow Mesenchymal Stem Cells" (2003) Stem Cells: vol. 21: 661-669.
Stepp et al., Syndecan-1 and its expanding list of contacts. Advances in Wound Care, 4(4):235-249, 2015.
Tang et al., Calcitriol suppresses antiretinal autoimmunity through inhibitory effects on the Th17 effector response. The Journal of Immunology, 182:4624-4632, 2009.
Technical Data Sheet, Purified Mouse Anti-human CD271, Jun. 6, 2013, p. 1-2.
Teixe et al., Corrigendum to "Syndecan-2 and -4 expressed on activated primary human CD4+lymphocytes can regulate T cell activation." Molecular Immunology, 51:368, 2012.
Teixe et al., Syndecan-2 and -4 expressed on activated primary human CD4+ lymphocytes can regulate T cell activation. Molecular Immunology, 45:2905-2919, 2008.
Theocharis et al., Insights into the key roles of proteoglycans in breast cancer biology and translational medicine. Biochimica et Biophysica Acta, 1855:276-300, 2015.
U.S. Appl. No. 14/377,597 Final Office Action dated Jan. 14, 2019.
U.S. Appl. No. 14/377,597 Office Action dated Apr. 7, 2016.
U.S. Appl. No. 14/377,597 Office Action dated Aug. 15, 2018.
U.S. Appl. No. 14/377,597 Office Action dated Jan. 30, 2017.
U.S. Appl. No. 14/377,597 Office Action dated May 12, 2017.
U.S. Appl. No. 14/377,597 Office Action dated Nov. 6, 2015.
U.S. Appl. No. 14/377,597 Office Action dated Sep. 9, 2016.
U.S. Appl. No. 14/785,001 Final Office Action dated Jun. 27, 2018.
U.S. Appl. No. 14/785,001 Office Action dated Feb. 15, 2017.
U.S. Appl. No. 14/785,001 Office Action dated Jun. 20, 2016.
U.S. Appl. No. 15/074,681 First Action Interview Pilot Program Pre-Interview Communication dated Dec. 9, 2016.
U.S. Appl. No. 15/074,681 Office Action dated Apr. 27, 2017.
U.S. Appl. No. 15/074,681 Restriction Requirement dated Aug. 22, 2016.
U.S. Appl. No. 15/089,435 Final Office Action dated Sep. 3, 2019.
U.S. Appl. No. 15/089,435 Non-Final Office Action dated Nov. 14, 2018.
U.S. Appl. No. 15/089,435 Office Action dated Oct. 4, 2017.
U.S. Appl. No. 16/009,048 Restriction Requirement dated Jun. 28, 2019.
Uniprot:P34741, XP002726498, 3 pages, printed Jun. 26, 2014, http://ibis.intemal.epo.org/exam/dbfetch.jsp?id=Uniprot•P3474I.
Wieczorek et al., Gene expression profile of mouse bone marrow stromal cells determined by cDNA microarray analysis.Cell Tissue Res. 311(2):227-237 (2003).
Yan, Xin-Long, et al., "Migration of Dorsal Aorta Mesenchymal Stem Cells Induced by Mouse Embryonic Circulation," Dynamics 240: 65-74 (2011).
Frantz et al. The extracellular matrix at a glance. Cell Science at a Glance 123, (2010), 4195-4200.
Hayes et al.: Mesenchymal stem cells—a promising therapy for Acute Respiratory Distress Syndrome. F1000 Med Rep. 4:2:1-7 (2012).
Korean Application No. 10-2015-7032129 Notice of Preliminary Rejection dated Oct. 14, 2021.
Nombela-Arrieta et al.: The elusive nature and function of mesenchymal stem cells. Nature Rev Mol Cell Bio. 12:126-131 (2011).
Prante et al.: The Formation of Extracellular Matrix During Chondrogenic Differentiation of Mesenchymal Stem Cells Correlates with Increased Levels of Xylosyltransferase I. Stem Cells. 24:2252-2261 (2006).
U.S. Appl. No. 14/377,597 Final Office Action dated Oct. 1, 2020.
U.S. Appl. No. 14/377,597 Office Action dated Feb. 20, 2020.
U.S. Appl. No. 14/377,597 Office Action dated Jun. 30, 2021.
U.S. Appl. No. 14/377,597 Office Action dated Oct. 7, 2019.
U.S. Appl. No. 15/089,435 Office Action dated Jun. 10, 2020.

(56) References Cited

OTHER PUBLICATIONS

U.S. Appl. No. 16/009,048 Final Office Action dated Jul. 24, 2020.
U.S. Appl. No. 16/562,206 Final Office Action dated Nov. 27, 2020.
U.S. Appl. No. 16/562,206 Office Action dated Dec. 12, 2019.
U.S. Appl. No. 16/562,206 Office Action dated May 11, 2020.
Xian et al.: Syndecans as receptors and organizers of the extracellular matrix. Cell Tissue Res. 339:31-46 (2010).
U.S. Appl. No. 16/254,378 Final Office Action dated Oct. 15, 2020.

* cited by examiner

Wild Type = 4, 5, 10, 11, 13, 20, 22, wt
Hetero = 1, 3, 7, 12, 14, 16, 17, 18, 19, 23, 24, 25, 26, 27, 29, 31, +ve
Homo = 2, 6, 8, 9, 15, 21, 28, 30

MODULATORS OF SYNDECAN-2 AND USES THEREOF

RELATED APPLICATIONS

This application is a continuation of U.S. application Ser. No. 15/074,681 filed Mar. 18, 2016, now allowed, which claims priority to European Application Serial No. 15160181.2, filed Mar. 20, 2015, the contents of which are hereby incorporated by reference in their entirety.

SEQUENCE LISTING

The present application is accompanied by a Sequence Listing submitted electronically in ASCII format, and which is hereby incorporated by reference in its entirety. Said ASCII copy, created on Oct. 8, 2018, is named 49707-702_301_SL.txt and is 18,236 bytes in size.

BACKGROUND

Provided herein are modulators of syndecan-2 and uses thereof, specifically to syndecan-2 antibodies and other syndecan-2 binding compositions for use in specific therapies and to methods of treatment and combination therapies using the modulators, e.g. antagonists, especially the antibodies.

The immune system has the ability to respond to pathogens using different mechanisms. If a pathogen succeeds in passing the first line of defense and enters the body, the innate immune response is activated, which involves a fast but largely non-specific response to infectious agents. The adaptive immune response is a slower but more specific response to pathogens.

Glycoproteins on the surface of T lymphocytes of the adaptive immune system, CD4 and CD8, give rise to the cells known as $CD4^+$ T cells and $CD8^+$ T cells. These CD molecules interact with other glycoproteins, major histocompatibility complex (MHC), on the surface of cells which then, in some cases, leads to the stimulation of the adaptive immune system. Antigen presenting cells, interact with T cell receptors, presenting antigens and resulting in $CD4^+$ T cell activation. When activated via APCs, $CD4^+$ T cells have the potential to differentiate into effector cells and have further immune functions.

Naïve $CD4^+$ T cells have the potential to differentiate further into different types of effector cells with distinct functions depending on what pattern of signals (e.g. cytokines) they receive when the naïve cell is exposed to antigens. The most well described of these cell types are $Th_1$, $Th_2$, Th17 and $T_{reg}$ cells.

The immune system usually acts as a defense against potential pathogens, for example bacteria, viruses, protozoa, and fungi. It comprises various specific and non-specific defenses, including several specific types of cells usually carried in the blood. Included among these are lymphocytes and in particular T cells, which are involved in the cell-mediated immune system. There are two major subtypes of T cells; namely cytotoxic T cells (Tc cells) and helper T cells (Th cells). T cells recognise antigens in combination with a major histocompatibility complex (MHC). Activation of Th cells causes the cells to release cytokines and other stimulatory signatures that stimulate the activity of macrophages, dendritic cells, neutrophils, natural killer cells or natural killer T-cells (NKT) aiding antigen clearance and also stimulate humoral response by stimulating B cells, with the B cells then producing antigen-specific antibodies.

In certain diseases, the immune system becomes overactive; these diseases including autoimmune diseases. In these diseases, the immune system does not correctly distinguish between "self" and "non-self", and attacks parts of the body rather than or in addition to pathogens. Examples of such diseases include celiac disease, diabetes mellitus type 1, sarcoidosis, systemic lupus erythematosus (SLE), Sjögren's syndrome, Churg-Strauss syndrome, Hashimoto's thyroiditis, Graves' disease, idiopathic thrombocytopenic purpura, Addison's disease, rheumatoid arthritis (RA), polymyositis (PM), and dermatomyositis (DM). New treatments for these and other auto-immune diseases are continually being sought.

Th17 cells are a sub-type of Th cells, which mainly produce their signature cytokine interleukin-17 (IL-17), in addition to the pro-inflammatory cytokines: IL-6, TNF, IL-21 and IL-22. Th17 cells are mainly involved in clearing pathogenic infection during host defense response by stimulating epithelial cells to produce cytokines, such as G-CSF and CXCL1, which act against bacteria and fungi and thus prevent opportunistic infections.

However, these cells are also involved in autoimmune diseases, creating tissue inflammation. The expression of IL-17 appears to be increased in human autoimmune diseases.

Chronic inflammation is also associated with development of cancer. Increases in inflammatory cytokines create an environment where a cancer cell is able to grow and spread to other tissues. Therefore, modulation of inflammatory T cells, such as Th17 cells, such as by modulators and inhibitors of syndecan-2, is useful in treatment of cancer.

Fibrosis in disease is the excessive formation of fibrous connective tissue. This, in some cases, is reparative, i.e. in response to an injury, where the connective tissue is known as scarring, or reactive, i.e. resulting from a disease condition.

Several diseases are associated with fibrosis, for example cystic fibrosis, cirrhosis and Crohn's disease, and in many cases the actual cause or initiation remains unknown.

Reparative fibrosis is regulated by a complex set of interactions, including profibrotic and antifibrotic cytokines and proteins. The proteins include profibrotic proteins, in particular transforming growth factor β (TGFβ) and connective tissue growth factor (CTGF) and antifibrotic proteins such as tumor necrosis factor-α (TNF-α) and interferon-γ (IFN-γ).

TGFβ is generally considered to be the most important inducer of extracellular matrix and is considered to be a principle mediator in fibrosis. It activates and stimulates proliferation of fibroblasts, which synthesize extracellular matrix and collagen, forming the connective tissues.

TGFβ also induces the secretion of CTGF in endothelial cells and is considered a downstream mediator of the effects of TGFβ on fibroblasts.

Additionally TGFβ induces expression of the ED-A form of the matrix protein fibronectin (ED-A FN). This is required for TGFβ1-triggered enhancement of α-SMA and collagen type I expression.

The proinflammatory cytokine TNF-α, is antifibrotic as it suppresses the expression of matrix genes, and is expressed by macrophages during a normal wound healing response. Additionally proinflammatory cytokine IFN-γ released by T cells immediately after injury suppresses collagen synthesis.

In addition TGFβ is involved in the regulation of T helper (Th) cell differentiation. The presence or absence of TGFβ in combination with other cytokines (IL-6, IL-1, or IL-23) is critical for the developmental program of regulatory and effector T helper cells and for the final outcome in terms of anti-infective response, pathogenicity, or suppressive capacity. TGFβ inhibits Th1 and Th2 differentiation. By contrast, TGFβ in combination with IL-6, and IL-21 promotes the development of induced Foxp3+ regulatory T cells to Th17 cells.

TGFβ is released by leukocytes and stromal cells and in a few settings macrophages and dendritic cells too. Recent discoveries reinforce the idea that communication between fibroblasts, macrophages, and CD4 T cells integrates the processes of wound healing and host defense. Signals between macrophages and fibroblasts, under certain conditions, exacerbate, suppress, or reverse fibrosis. Fibroblasts and macrophages are activated by T cells, but their activation also engages negative feedback loops that reduce fibrosis by restraining the immune response, particularly when the Th2 cytokine IL-13 contributes to pathology. Thus the interactions among fibroblasts, macrophages, and CD4 T cells play general and critical roles in initiating, perpetuating, and resolving fibrosis in both experimental and clinical conditions. It is desired to provide improved anti-fibrosis therapies.

Macrophages also promote inflammation by recruiting and activating monocytes and neutrophils, provide antigens to CD4 T cells, and modulate cell responses with costimulation and cytokines. CD4 T cells coordinate the immune response with cytokines, enhancing neutrophil recruitment with IL-17A, activating macrophages with IL-4 and IL-13 or IFN-γ, and inducing collagen production by fibroblasts with IL-4, IL-13, and possibly TGF-β. The combination of activating signals from the inflammatory environment, macrophages, and CD4 T cells stimulate fibroblasts to proliferate and synthesize collagens, matrix metalloproteinases (MMPs), and tissue inhibitors of metalloproteinases (TIMPs) that construct and remodel extracellular matrix and lead to fibrosis.

The syndecans are a family of heparan sulfate proteoglycans expressed on the cell surface of many mammalian cell types. The family members each comprise an extracellular domain and a transmembrane domain. The transmembrane domain is required for endogenous Syndecan-2 dimerization in vivo. Syndecan-2, encoded by the SDC2 locus and sometimes alternately referred to as SDC2, S2, CD362, or fibroglycan, is a member of this family that is primarily expressed in fibroblasts, developing neural tissue, mesenchymal stromal cells (MSCs) and mesenchymal cell types. Syndecan-2 has many roles to play in the body such as growth factor receptor activation and cell-cell adhesion in addition to its role in the immune system.

SUMMARY

The present disclosure provides agents and therapies for autoimmune disease, fibrosis, and cancer. An object of particular embodiments of the disclosure is to provide such agents and therapies based on targeted cellular action of modulators of syndecan-2.

Embodiments herein modulate syndecan-2 (SDC2) expression and/or activity in some cases reducing or reversing key elements of autoimmune disease, fibrosis, and some cancers. Accordingly, the present disclosure provides modulators of SDC2, including fragments of SDC2, antibodies that bind SDC2, antagonists to SDC2, and compositions comprising such active agents for use in treatment of autoimmune disease, fibrosis, and cancer. The present disclosure provides methods of treatment of autoimmune disease and fibrosis comprising administering SDC2 modulators and Th17 modulators as disclosed herein. Often, the administration is intraveinous administration.

Provided herein, in some aspects, are modulators of syndecan-2 for use in treatment of autoimmune disease. Various embodiments of these modulators are recited below, contemplated as distinct or in combination. In some embodiments, a modulator inhibits Th17 cell activity. In some embodiments, a modulator binds to cell surface syndecan-2. In some embodiments, a modulator cross-links cell surface syndecan-2. In some embodiments, a modulator inhibits NFκB. In some embodiments, a modulators is an antibody to syndecan-2. In some embodiments, a modulator comprises a first portion that binds to syndecan-2 and a second portion comprises a homodimerization domain. In some embodiments, the first portion comprises a fragment of syndecan-2. In some embodiments, the fragment is a fragment of the extracellular region of syndecan-2. In some embodiments, the fragment of syndecan-2 has an amino acid sequence selected from MRRAWILLTLGLVACV-SAESRAELTSDKDMYLDNSSIEEASGVYPIDDDD-DYASASGSGADE DVESPELTTSRPLPKILL (SEQ ID NO: 4), MRRAWILLTLGLVACVSAESRAELTSDKDM-YLDNSSIEEASGVYPIDDDDYASASGSGADE DVESPELTTSRPLPKILLTSAAPKVE (SEQ ID NO: 5), MRRAWILLTLGLVACVSAESRAELTSDKDM-YLDNSSIEEASGVYPIDDDDYASASGSGADE DVESPELTTSRPLPKILLTSAAPKVETTTLNIQNKIPAQ (SEQ ID NO: 6), MRRAWILLTLGLVACVSAESRAELT-SDKDMYLDNSSIEEASGVYPIDDDDYASASGSGADE DVESPELTTSRPLPKILLTSAAPKVETTTLNIQNKI-PAQTKSPEETDKEKVHLSDSERKMDPA EEDTN-VYTEKHSDSLFKRTE (SEQ ID NO: 7), MRRAWILLTLGLVACVSAESRAELTSDKDM-YLDNSSIEEASGVYPIDDDDYASASGSGADE DVESPELTTSRPLPKILLTSAAPKVETTTLNIQNKI-PAQTKSPEETDKEKVHLSDSERKMDPA EEDTN-VYTEKHSDSLFKRTEVLAAVIAGGVIGFL-FAIFLILLLVY (SEQ ID NO: 8), TLGLVACVSAESRAELTSDKDMYLDNSSIEE-ASGVYPIDDDDYASASGSGADEDVESPELTT SRPLP-KILL (SEQ ID NO: 9), ESRAELTSDKDMYLDNSSIEE-ASGVYPIDDDDYASASGSGADEDVESPELTTSRPL PKILLTS AAPKVE (SEQ ID NO: 10), ESRAELTSDKDM-YLDNSSIEEASGVYPIDDDDYASASGSGADED-VESPELTTSRPLPKILLTS AAPKVETTTLNIQNKIPAQ (SEQ ID NO: 11), ESRAELTSDKDMYLDNSSIEE-ASGVYPIDDDDYASASGSGADEDVESPELTTSRPLP-KILLTS AAPKVETTTLNIQNKIPAQTKSPEETD-KEKVHLSDSERKMDPAEEDTNVYTEKHSDSLFKRT EVLAAVIAGGVIGFLFAIFLILLLVY (SEQ ID NO: 12), and ESRAELTSDKDMYLDNSSIEEASGVYPIDDD-DYASASGSGADEDVESPELTTSRPLPKILLTS AAPKVETTTLNIQNKIPAQTKSPEETDKEKVHLSD-SERKMDPAEEDTNVYTEKHSDSLFKRT EVLAAVI-AGGVIGELFAIFLILLLVYRMRKKDEGSYDLGERKPS-SAAYQKAPTKEFYA (SEQ ID NO: 13). In some embodiments, the second portion comprises an Fc portion of a fragment thereof. In some embodiments, a modulator comprises first and second portions, both of which bind to syndecan-2. In some embodiments, a modulator is a fragment of syndecan-2. In some embodiments, the fragment of syndecan-2 has an amino acid sequence selected from the list consisting of SEQ ID NOs: 4-13.

Also provided herein, in some aspects are antagonists of syndecan-2 for use in treatment of autoimmune disease. Various embodiments of these modulators are recited below, contemplated as distinct or in combination. In some embodiments, an antagonist inhibits Th17 cell activity. In some embodiments, an antagonist binds to cell surface syndecan-2. In some embodiments, an antagonist cross-links cell surface syndecan-2. In some embodiments, an antagonist inhibits NFκB. In some embodiments, an antagonist is an antibody to syndecan-2. In some embodiments, an antagonist is a fragment of syndecan-2. In some embodiments, the fragment of syndecan-2 has an amino acid sequence of SEQ ID NOs: 4-13.

Also provided herein, in some aspects, are fragments of syndecan-2 for use in treatment of autoimmune disease. In some embodiments, the fragment of syndecan-2 has an amino acid sequence of SEQ ID NOs: 4-13. In some embodiments, the fragment inhibits Th17 cell activity. In some embodiments, the fragment binds to cell surface syndcan-2. In some embodiments, the fragment crosslinks cell surface syndecan-2. In some embodiments, the fragment inhibits NFκB activity. In some embodiments, the autoimmune disease is selected from psoriasis, rheumatoid arthritis, psoriatic arthritis, lupus erythematosus, ulcerative colitis, Crohn's disease, acute respiratory distress syndrome and multiple sclerosis. In some embodiments, a modulator, an antagonist or a fragment for use for treatment of an autoimmune disease. In some embodiments, a composition comprising a modulator, an antagonist, or a fragment is for use for treatment of autoimmune disease by inhibiting Th17 cell activity.

In additional aspects, there are provided, methods of alleviating at least one symptom of an autoimmune disease, comprising administering an effective amount of a modulator of syndecan-2 or an antagonist of syndecan-2 to an individual in need thereof. There is further provided, methods of alleviating at least one symptom of an autoimmune disease, comprising administering an effective amount of a modulator of syndecan-2 or an antagonist of syndecan-2 to an individual in need thereof to inhibit Th17 cell activity. Various embodiments of these methods are recited below, contemplated as distinct or in combination. In some embodiments, the modulator or antagonist binds to cell surface syndecan-2. In some embodiments, the modulator or antagonist cross-links syndecan-2. In some embodiments, the modulator or antagonist inhibits NFκB activity. In some embodiments, the method comprises administering an antibody to syndecan-2. In some embodiments, the method comprises administering a fragment of syndecan-2. In some embodiments, the fragment of syndecan-2 has an amino acid sequence of SEQ ID NOs: 4-13. In some embodiments, the autoimmune disease is selected from psoriasis, rheumatoid arthritis, psoriatic arthritis, lupus erythematosus, ulcerative colitis, Crohn's disease, acute respiratory distress syndrome and multiple sclerosis.

In further aspects, there are provided, modulators of syndecan-2 for use in treatment of fibrosis. Various embodiments of these modulators are recited below, contemplated as distinct or in combination. In some embodiments, a modulator inhibits Th17 activity. In some embodiments, a modulator binds to cell surface syndecan-2. In some embodiments, a modulator cross-links cell surface syndecan-2. In some embodiments, a modulator inhibits NFκB activity. In some embodiments, a modulator is an antibody to syndecan-2. In some embodiments, a modulator is a fragment of syndecan-2. In some embodiments, the fragment of syndecan-2 has an amino acid sequence of SEQ ID NOs: 4-13. In some embodiments, a modulator comprises a first portion that binds to syndecan-2 and a second portion that forms a homodimer with itself. In some embodiments, the first portion comprises a fragment of syndecan-2. In some embodiments, the fragment is a fragment of the extracellular region of syndecan-2. In some embodiments, the fragment of syndecan-2 has an amino acid sequence of SEQ ID NOs: 4-13. In some embodiments, the second portion comprises an Fc portion of a fragment thereof. In some embodiments, a modulator comprises first and second portions, both of which bind to syndecan-2.

In additional aspects, there are provided antagonists of syndecan-2 for use in treatment of fibrosis. Various embodiments of these modulators are recited below, contemplated as distinct or in combination. In some embodiments, the antagonist inhibits Th17 cell activity. In some embodiments, the antagonist binds to cell surface syndecan-2. In some embodiments, the antagonist cross-links cell surface syndecan-2. In some embodiments, the antagonist inhibits NFκB activity. In some embodiments, the antagonist is an antibody to syndecan-2. In some embodiments, the antagonist is a fragment of syndecan-2. In some embodiments, the fragment of syndecan-2 has an amino acid sequence of SEQ ID NOs: 4-13.

Also provided herein, in some aspects, are fragments of syndecan-2 for use in treatment of fibrosis. Various embodiments of these fragments are recited below, contemplated as distinct or in combination. In some embodiments, the fragment of syndecan-2 has an amino acid sequence of SEQ ID NOs: 4-13. In some embodiments, the fragment inhibits Th17 cell activity. In some embodiments, the fragment binds to cell surface syndcan-2. In some embodiments, the fragment crosslinks cell surface syndecan-2. In some embodiments, the fragment inhibits NFκB activity. In some embodiments, the fibrosis is selected from fibrotic diseases of the lung, fibrotic diseases of the liver and fibrotic diseases of the heart. In some embodiments, there are provided compositions comprising modulators, antagonists, or fragments herein, for treatment of fibrosis. In some embodiments, modulators, antagonists, and fragments inhibit Th17 cell activity.

Provided herein, in certain aspects, are methods of alleviating at least one symptom of fibrosis, comprising administering an effective amount of a modulator of syndecan-2, an antagonist of syndecan-2, or a fragment of syndecan-2 to an individual in need thereof. Various embodiments of these fragments are recited below, contemplated as distinct or in combination. In some embodiments, the method comprises administering a modulator of syndecan-2 or an antagonist of syndecan-2 to inhibit Th17 cell activity. In some embodiments, the modulator, antagonist, or fragment binds to cell surface syndecan-2. In some embodiments, the modulator, antagonist, or fragment cross-links syndecan-2. In some embodiments, the modulator, antagonist, or fragment inhibits NFκB activity. In some embodiments, the method comprises administering an antibody to syndecan-2. In some embodiments, the method comprises administering a fragment of syndecan-2. In some embodiments, the fragment of syndecan-2 has an amino acid sequence of SEQ ID NOs: 4-13.

Also provided herein, in some aspects, are modulators of syndecan-2 for use in treatment of cancer. Various embodiments of these modulators are recited below, contemplated as distinct or in combination. In some embodiments, the modulator inhibits Th17 cell activity. In some embodiments, the modulator binds to cell surface syndecan-2. In some embodiments, the modulator cross-links cell surface syndecan-2. In some embodiments, the modulator inhibits NFκB activity. In some embodiments, the modulator is an antibody to syndecan-2. In some embodiments the modulator comprises a first portion that binds to syndecan-2 and a second portion that forms a homodimer with itself. In some embodiments, the first portion comprises a fragment of syndecan-2. In some embodiments, the fragment is a fragment of the extracellular region of syndecan-2. In some embodiments, the fragment of syndecan-2 has an amino acid sequence of SEQ ID NOs: 4-13. In some embodiments, the second portion comprises an Fc portion of a fragment thereof. In some embodiments, the modulator comprises first and second portions, both of which bind to syndecan-2. In some embodiments, the modulator is a fragment of syndecan-2. In some embodiments, the fragment of syndecan-2 has an amino acid sequence of SEQ ID NOs: 4-13.

In further aspects, there are provided antagonists of syndecan-2 for use in treatment of cancer. Various embodiments of these antagonists are recited below, contemplated as distinct or in combination. In some embodiments, the antagonist inhibits Th17 cell activity. In some embodiments, the antagonist binds to cell surface syndecan-2. In some embodiments, the antagonist cross-links cell surface syndecan-2. In some embodiments, the antagonist inhibits NFκB activity. In some embodiments, the antagonist is an antibody to syndecan-2. In some embodiments, the antagonist is a fragment of syndecan-2. In some embodiments, the fragment of syndecan-2 has an amino acid sequence of SEQ ID NOs: 4-13.

Also provided herein, in some aspects, are fragments of syndecan-2 for use in treatment of cancer. Various embodiments of these fragments are recited below, contemplated as distinct or in combination. In some embodiments, the fragment of syndecan-2 has an amino acid sequence of SEQ ID NOs: 4-13. In some embodiments, the fragment inhibits Th17 cell activity. In some embodiments, the fragment binds to cell surface syndcan-2. In some embodiments, the fragment crosslinks cell surface syndecan-2. In some embodiments, the fragment inhibits NFκB activity. In some embodiments, the cancer is selected from breast cancer, colon cancer, rectal cancer, lung cancer, non-Hodgkin's lymphoma, leukemia, lymphoma, ovarian cancer, prostate cancer, skin cancer, brain cancer, bladder cancer, endometrial cancer, kidney cancer, pancreatic cancer, thyroid cancer, and melanoma. In some embodiments, the modulator, the antagonist or the fragment are for use for treatment of a cancer. In some embodiments, the modulator, the antagonist or the fragment inhibit Th17 cell activity.

Also provided herein, in some aspects, are methods of alleviating at least one symptom of cancer, comprising administering an effective amount of a modulator of syndecan-2 or an antagonist of syndecan-2 to an individual in need thereof. In further aspects, there are provided methods of alleviating at least one symptom of cancer, comprising administering an effective amount of a modulator of syndecan-2 or an antagonist of syndecan-2 to an individual in need thereof to inhibit Th17 cell activity. Various embodiments of these fragments are recited below, contemplated as distinct or in combination. In some embodiments, the modulator or antagonist binds to cell surface syndecan-2. In some embodiments, the modulator or antagonist cross-links syndecan-2. In some embodiments, the method comprises administering an antibody to syndecan-2. In some embodiments, the method comprises administering a fragment of syndecan-2. In some embodiments, the fragment of syndecan-2 has an amino acid sequence of SEQ ID NOs: 4-13. In some embodiments, the cancer is selected from breast cancer, colon cancer, rectal cancer, lung cancer, non-Hodgkin's lymphoma, leukemia, lymphoma, ovarian cancer, prostate cancer, skin cancer, brain cancer, bladder cancer, endometrial cancer, kidney cancer, pancreatic cancer, thyroid cancer, and melanoma. In some embodiments, the modulator of or antagonist of syndecan-2 is for use in treatment of autoimmune disease, in combination with a population of mammalian cells at least 30% of which are positive for syndecan-2. In some embodiments, the modulator of or antagonist of syndecan-2 is for use in treatment of autoimmune disease, in combination with a population of mammalian cells comprising CD4+CD25+ Foxp3+ regulatory T cells. In some embodiments, the modulator of or antagonist of syndecan-2 is for use in treatment of fibrosis, in combination with a population of mammalian cells at least 30% of which are positive for syndecan-2. In some embodiments, the modulator of or antagonist of syndecan-2 is for use in treatment of fibrosis, in combination with a population of mammalian cells comprising CD4+CD25+ Foxp3+ regulatory T cells. In some embodiments, the modulator or antagonist of syndecan-2 is for use in treatment of cancer, in combination with a population of mammalian cells at least 30% of which are positive for syndecan-2. In some embodiments, the modulator or antagonist of syndecan-2 is for use in treatment of cancer, in combination with a population of mammalian cells comprising CART cells. In some embodiments, the modulator or antagonist of syndecan-2 is for use in treatment of cancer, in combination with a population of mammalian cells comprising isolated tumor infiltrating lymphocytes. In some embodiments, the modulator or antagonist of syndecan-2 is for use in treatment of cancer, in combination with a population of mammalian cells comprising CCR7+, CD62L+ central memory T cells. In some embodiments, the modulator or antagonist of syndecan-2 is for use in treatment of cancer, in combination with a population of mammalian cells comprising natural killer cells. In some embodiments, 50% or more of the mammalian cells are positive for syndecan-2.

Also provided herein, in some aspects, are fragments of syndecan-2, wherein the fragment has an amino acid sequence comprising at least a portion of a polypeptide having a sequence MRRAWILLTLGLVACVSAESRAELTSDKDMYLDNSSIEEASGVYPIDDDDYASASGSGADE DVESPELTTSRPLPKILLTSAAPKVETTTLNIQNKIPAQTKSPEETDKEKVHLSDSERKMDPA EEDTNVYTEKHSDSLFKRTEVLAAVIAGGVIGFLFAIFLILLLVYRMRKKDEGSYDLGERKPS SAAYQKAPTKEFYA (SEQ ID NO: 1). Various embodiments of these fragments are recited below, contemplated as distinct or in combination. In some embodiments, the fragment comprises consecutive residues comprising at least 70% of the residues in SEQ ID NO: 1. In some embodiments, the fragment comprises at least a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment consists of a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment comprises at least a portion of an extracellular domain of syndecan-2 polypeptide ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVYTEKHSDSLFKRT E (SEQ ID NO: 2). In some embodiments, the fragment comprises a polypeptide having a sequence selected from SEQ ID NOs: 4-13. In some embodiments, the fragment inhibits syndecan-2 activity. In some embodiments, the fragment inhibits NFκB activity.

Also provided herein, in some aspects, are fusion polypeptides comprising a first portion and a second portion, wherein the first portion binds to a syndecan-2 protein. Various embodiments of these fusion polypeptides are recited below, contemplated as distinct or in combination. In some embodiments, the first portion comprises any of the above fragments of syndecan-2. In some embodiments, the first portion comprises an anti-syndecan-2 antibody or fragment thereof. In some embodiments, the first portion comprises at least a portion of a VH domain, a VL domain, a VH-CDR1, VH-CDR2, VH-CDR3, VL-CDR1, VL-CDR2, VL-CDR3 domain, or combinations thereof. In some embodiments, the first portion comprises a single domain antibody binding to syndecan-2. In some embodiments, the second portion comprises a dimerization domain. In some embodiments, the second portion is selected from the group consisting of an Fc polypeptide and a leucine zipper polypeptide. In some embodiments, the polypeptide is modified wherein the modification is selected from the group consisting of a glycosylation and a phosphorylation. In some embodiments, there is provided, a pharmaceutical composition comprising the fragment, the fusion polypeptide, or the modified polypeptide, and a pharmaceutically acceptable buffer or excipient. In some embodiments, the pharmaceutically acceptable buffer or excipient comprises at least one of the group consisting of maleic acid, tartaric acid, lactic acid, citric acid, acetic acid, sodium bicarbonate, sodium phosphate, histadine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitanmonooleate. In some embodiments, the pharmaceutical composition comprises an additional therapeutic agent for treating an autoimmune disease, a fibrosis, or a cancer. In some embodiments, the additional therapeutic agent for treating an autoimmune disease comprises at least one of the group consisting of a non-steroidal anti-inflammatory drug (NSAID), iburprofen, naproxen, meloxicam, etodolac, nabumetone, sulindac, tolementin, choline magnesium salicylate, diclofenac, diflusinal, indomethescin, ketoprofen, meloxicam, oxaprozin, piroxicam, celecoxib, etoricoxib, lumiracoxib, a corticosteroid, methotrexate, hydroxychloroquine, sulfasalazine, leflunomide, a TNFa inhibitor, etanercept, adalimumab, infliximab, certolizumab pegol, golimumab, abatacept, rituximab, tociluzumab, anakinra, cyclosporine, antithymocyte globulin, mycophenolate mofetil, and cyclosphomaide. In some embodiments, the additional therapeutic agent for treating fibrosis comprises at least one of the group consisting of nintedanib, pirfenidone, a corticosteroid, albuterol, levabuterol, salmeterol, formoterol, flovent, and pulmicort. In some embodiments, the additional therapeutic agent for treating cancer comprises at least one of the group consisting of methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl) amine, troxacitabine, uracil mustard, valrubicin, vinblastine, vincristine, vinorelbine, vorinostat, and zosuquidar. In some embodiments, the additional therapeutic agent for treating cancer comprises at least one of the group consisting of hydromorphone, levorphanol, methadone, morphine, oxycodone, hydrocodone, oxymorphone, fentanyl, dolasetron, granisetron, ondansetron, palonosetron, dexamethasone, methylpredinsolone, droperidol, haloperidol, metoclopramide, prochlorperazine, promethazine, lorazepam, alprazolam, dronabinol, nabilone, aprepitant, rolapitant, epoetin, darbepoetin, filgrastim, pegfilgrastim, and sargramostim. In some embodiments, the pharmaceutical composition comprises a population of mammalian cells at least 30% of which are positive for syndecan-2. In some embodiments, the pharmaceutical composition comprises a population of CAR T cells. In some embodiments, the pharmaceutical composition comprises a population of isolated tumor infiltrating lymphcytes. In some embodiments, the pharmaceutical composition comprises a population of CCR7+, CD62L+ central memory T cells. In some embodiments, the pharmaceutical composition comprises a population of natural killer cells. In some embodiments, the pharmaceutical composition comprises a population of CD4+CD25+ Foxp3+ regulatory T cells.

In additional aspects, there are provided methods of reducing at least one symptom in a subject with autoimmune disease comprising identifying a subject having an autoimmune disease and administering an effective amount of a modulator of syndecan-2 sufficient to reduce at least one symptom of the autoimmune disease. Various embodiments of these methods are recited below, contemplated as distinct or in combination. In some embodiments, the method comprises monitoring the subject for improvement in at least one symptom of the autoimmune disease. In some embodiments, the symptom comprises a symptom selected from the group consisting of elevated Th17 cell numbers, Th17 cell activity, Th17 cytokine levels, and IL-17 levels. In some embodiments, the modulator of syndecan-2 comprises an inhibitor of Th17 cell activity. In some embodiments, the modulator comprises a polypeptide that binds to a cell surface syndecan-2. In some embodiments, the modulator comprises a polypeptide that cross-links cell surface syndecan-2. In some embodiments, the modulator comprises an antibody to syndecan-2, or fragment thereof. In some embodiments, the modulator comprises a fusion protein comprising a first portion comprising a polypeptide that binds to syndecan-2 and a second portion comprising a dimerization domain. In some embodiments, the first portion comprises a fragment of syndecan-2. In some embodiments, the fragment of syndecan-2 is a fragment of the extracellular region of syndecan-2 comprising at least a portion of a sequence ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVY TEKHSDSLFKRT E (SEQ ID NO: 2). In some embodiments, the fragment of syndecan-2 has an amino acid sequence of SEQ ID NOs: 4-13. In some embodiments, the second portion comprises an Fc portion of a fragment thereof. In some embodiments, the modulator comprises a fusion protein comprising a first portion and a second portion, wherein the first portion and the second portion each comprise a polypeptide that binds to syndecan-2. In some embodiments, the modulator comprises a fragment of syndecan-2 comprising at least a portion of a sequence MRRAWILLTLGLVACVSAESRAELTSDKDMYLDNSSIEEASGVYPIDDDDYASASGSGADEDVESPELTTSRPLPKILLTSAAPKVETTTLNIQNKIPAQTKSPEETDKEKVHLSDSERKMDPA EEDTNVYTEKHSDSLFKRTEVLAAVIAGGVIGFLFAIFLILLLVYRMRKKDEGSYDLGERKPS SAAYQKAPTKEFYA (SEQ ID NO: 1). In some embodiments, the fragment comprises consecutive residues comprising at least 70% of the residues in SEQ ID NO: 1. In some embodiments, the fragment comprises at least a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment consists of a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment comprises at least a portion of an extracellular domain of syndecan-2 polypeptide ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVYTEKHSDSLFKRT E (SEQ ID NO: 2). In some embodiments, the fragment has an amino acid sequence of SEQ ID NOs: 4-13. In some embodiments, the modulator comprises an antagonist of syndecan-2. In some embodiments, the autoimmune disease is selected from the group consisting of from psoriasis, rheumatoid arthritis, psoriatic arthritis, lupus erythematosus, ulcerative colitis, Crohn's disease, acute respiratory distress syndrome and multiple sclerosis. In some embodiments, the modulator is administered to the subject as a pharmaceutical composition comprising the modulator and at least one pharmaceutically acceptable buffer, carrier or excipient. In some embodiments, the pharmaceutical composition comprises a population of mammalian cells at least 30% of which are positive for syndecan-2. In some embodiments, the pharmaceutical composition comprises a population of CD4+CD25+ Foxp3+ regulatory T cells.

Also provided herein, in some aspects, are methods of reducing at least one symptom in a subject with fibrosis comprising identifying a subject having a fibrosis and administering an effective amount of a modulator of syndecan-2 sufficient to reduce at least one symptom of the fibrosis. Various embodiments of these methods are recited below, contemplated as distinct or in combination. In some embodiments, the method comprises monitoring the subject for improvement in at least one symptom of the fibrosis. In some embodiments, the symptom comprises a symptom selected from the group consisting of elevated Th17 cell numbers, Th17 cell activity, Th17 cytokine levels, and IL-17 levels. In some embodiments, the modulator of syndecan-2 comprises an inhibitor of Th17 cell activity. In some embodiments, the modulator comprises a polypeptide that binds to a cell surface syndecan-2. In some embodiments, the modulator comprises a polypeptide that cross-links cell surface syndecan-2. In some embodiments, the modulator comprises an antibody to syndecan-2, or fragment thereof. In some embodiments, the modulator comprises a fusion protein comprising a first portion comprising a polypeptide that binds to syndecan-2 and a second portion comprising a dimerization domain. In some embodiments, the first portion comprises a fragment of syndecan-2. In some embodiments, the fragment of syndecan-2 is a fragment of the extracellular region of syndecan-2 comprising at least a portion of a sequence ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVYTEKHSDSLFKRT E (SEQ ID NO: 2). In some embodiments, the fragment of syndecan-2 has an amino acid sequence of SEQ ID NOs: 4-13. In some embodiments, the second portion comprises an Fc portion of a fragment thereof. In some embodiments, the modulator comprises a fusion protein comprising a first portion and a second portion, wherein the first portion and the second portion each comprise a polypeptide that binds to syndecan-2. In some embodiments, the modulator comprises a fragment of syndecan-2 comprising at least a portion of a sequence MRRAWILLTLGLVACVSAESRAELTSDKDMYLDNSSIEEASGVYPIDDDDYASASGSGADEDVESPELTTSRPLPKILLTSAAPKVETTTLNIQNKIPAQTKSPEETDKEKVHLSDSERKMDPA EEDTNVYTEKHSDSLFKRTEVLAAVIAGGVIGFLFAIFLILLLVYRMRKKDEGSYDLGERKPS SAAYQKAPTKEFYA (SEQ ID NO: 1). In some embodiments, the fragment comprises consecutive residues comprising at least 70% of the residues in SEQ ID NO: 1. In some embodiments, the fragment comprises at least a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment consists of a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment comprises at least 10 consecutive residues of an extracellular domain of syndecan-2 polypeptide ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVY TEKHSDSLFKRT E (SEQ ID NO: 2). In some embodiments, the fragment has an amino acid sequence of SEQ ID NOs: 4-13. In some embodiments, the modulator comprises an antagonist of syndecan-2. In some embodiments, the fibrosis is selected from the group consisting of fibrotic diseases of the lung, fibrotic diseases of the liver and fibrotic diseases of the heart. In some embodiments, the modulator is administered to the subject as a pharmaceutical composition comprising the modulator and at least one pharmaceutically acceptable buffer, carrier or excipient. In some embodiments, the pharmaceutical composition comprises a population of mammalian cells at least 30% of which are positive for syndecan-2. In some embodiments, the pharmaceutical composition comprises a population of CD4+ CD25+ Foxp3+ regulatory T cells.

Also provided herein, in some aspects, are methods of reducing at least one symptom in a subject with cancer comprising identifying a subject having a cancer and administering an effective amount of a modulator of syndecan-2 sufficient to reduce at least one symptom of the cancer. Various embodiments of these methods are recited below, contemplated as distinct or in combination. In some embodiments, the method comprises monitoring the subject for improvement in at least one symptom of the cancer. In some embodiments, the symptom comprises a symptom selected from the group consisting of elevated Th17 cell numbers, Th17 cell activity, Th17 cytokine levels, and IL-17 levels. In some embodiments, the modulator of syndecan-2 comprises an inhibitor of Th17 cell activity. In some embodiments, the modulator comprises a polypeptide that binds to a cell surface syndecan-2. In some embodiments, the modulator comprises a polypeptide that cross-links cell surface syndecan-2. In some embodiments, the modulator comprises an antibody to syndecan-2, or fragment thereof. In some embodiments, the modulator comprises a fusion protein comprising a first portion comprising a polypeptide that binds to syndecan-2 and a second portion comprising a dimerization domain. In some embodiments, the first portion comprises a fragment of syndecan-2. In some embodiments, the fragment of syndecan-2 is a fragment of the extracellular region of syndecan-2 comprising at least a portion of a sequence ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVYTEKHSDSLFKRT E (SEQ ID NO: 2). In some embodiments, the second portion comprises an Fc portion of a fragment thereof. In some embodiments, the modulator comprises a fusion protein comprising a first portion and a second portion, wherein the first portion and the second portion each comprise a polypeptide that binds to syndecan-2. In some embodiments, the modulator comprises a fragment of syndecan-2 comprising a sequence of at least 10 consecutive residues of the polypeptide sequence MRRAWILLTLGLVACVSAESRAELTSDKDMYLDNSSIEEASGVYPIDDDDYASASGSGADE DVESPELTTSRPLPKILLTSAAPKVETTTLNIQNKIPAQTKSPEETDKEKVHLSDSERKMDPA EEDTNVYTEKHSDSLFKRTEVLAAVIAGGVIGFLFAIFLILLLVYRMRKKDEGSYDLGERKPS SAAYQKAPTKEFYA (SEQ ID NO: 1). In some embodiments, the fragment comprises consecutive residues comprising at least 70% of the residues in SEQ ID NO: 1. In some embodiments, the fragment comprises at least a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment consists of a portion of wildtype syndecan-2 having at least 10, 20, 30, 40, 50, 60, 70, 80, 90, 100, 110, 120, 130, 140, 150, or 160 amino acids of SEQ ID NO: 1. In some embodiments, the fragment comprises at least a portion of an extracellular domain of syndecan-2 polypeptide ESRAELTSDKDMYLDNSSIEEASGVYPIDDDDYASASGSGADEDVESPELTTSRPLPKILLTS AAPKVETTTLNIQNKIPAQTKSPEETDKEKVHLSDSERKMDPAEEDTNVYTEKHSDSLFKRT E (SEQ ID NO: 2). In some embodiments, the fragment has an amino acid sequence of SEQ ID NOs: 4-13. In some embodiments, the modulator comprises an antagonist of syndecan-2. In some embodiments, the cancer is selected from the group consisting of from breast cancer, colon cancer, rectal cancer, lung cancer, non-Hodgkin's lymphoma, leukemia, lymphoma, ovarian cancer, prostate cancer, skin cancer, brain cancer, bladder cancer, endometrial cancer, kidney cancer, pancreatic cancer, thyroid cancer, and melanoma. In some embodiments, the modulator is administered to the subject as a pharmaceutical composition comprising the modulator and at least one pharmaceutically acceptable buffer, carrier or excipient. In some embodiments, the pharmaceutical composition comprises a population of mammalian cells at least 30% of which are positive for syndecan-2. In some embodiments, the pharmaceutical composition comprises a population of CAR T cells. In some embodiments, the pharmaceutical composition comprises a population of isolated tumor infiltrating lymphcytes. In some embodiments, the pharmaceutical composition comprises a population of CCR7+, CD62L+ central memory T cells. In some embodiments, the pharmaceutical composition comprises a population of natural killer cells.

In additional aspects, there are provided compositions comprising a polypeptide comprising a syndecan-2 binding domain and a physiologically acceptable buffer. Various embodiments of these compositions are recited below, contemplated as distinct or in combination. In some embodiments, the syndecan-2 binding domain comprises an antibody variable domain that binds at least one mammalian syndecan-2 protein. In some embodiments, the antibody variable domain binds human syndecan-2. In some embodiments, the antibody variable domain binds a nonhuman mammalian syndecan-2. In some embodiments, the antibody variable domain specifically binds human syndecan-2. In some embodiments, the antibody variable domain is chimeric. In some embodiments, the antibody variable domain is humanized. In some embodiments, the polypeptide comprises a dimerization domain. In some embodiments, the dimerization domain is a homodimerization domain. In some embodiments, the dimerization domain comprises a Fc domain. In some embodiments, the physiologically acceptable buffer comprises at least one compound selected from the group consisting of maleic acid, tartaric acid, lactic acid, citric acid, acetic acid, sodium bicarbonate, sodium phosphate, histadine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitanmonooleate. In some embodiments, the physiologically acceptable buffer is suitable for intravenous administration. In some embodiments, the composition comprises an additional therapeutic agent. In some embodiments, comprises at least one autoimmune disease agent selected from the group consisting of a non-steroidal anti-inflammatory drug (NSAID), iburprofen, naproxen, meloxicam, etodolac, nabumetone, sulindac, tolementin, choline magnesium salicylate, diclofenac, diflusinal, indomethescin, ketoprofen, meloxicam, oxaprozin, piroxicam, celecoxib, etoricoxib, lumiracoxib, a corticosteroid, methotrexate, hydroxychloroquine, sulfasalazine, leflunomide, a TNFa inhibitor, etanercept, adalimumab, infliximab, certolizumab pegol, golimumab, abatacept, rituximab, tociluzumab, anakinra, cyclosporine, antithymocyte globulin, mycophenolate mofetil, and cyclosphomaide. In some embodiments, the additional therapeutic agent comprises at least one fibrosis disease agent selected from the group consisting of nintedanib, pirfenidone, a corticosteroid, albuterol, levabuterol, salmeterol, formoterol, flovent, and pulmicort. In some embodiments, the additional therapeutic agent comprises at least one cancer agent selected from the group consisting of methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar In some embodiments, the additional therapeutic agent comprises at least one cancer agent selected from the group consisting of hydromorphone, levorphanol, methadone, morphine, oxycodone, hydrocodone, oxymorphone, fentanyl, dolasetron, granisetron, ondansetron, palonosetron, dexamethasone, methylpredinsolone, droperidol, haloperidol, metoclopramide, prochlorperazine, promethazine, lorazepam, alprazolam, dronabinol, nabilone, aprepitant, rolapitant, epoetin, darbepoetin, filgrastim, pegfilgrastim, and sargramostim. In some embodiments, the composition comprises a population of mammalian cells at least 30% of which are positive for syndecan-2. In some embodiments, the composition comprises a population of CART cells. In some embodiments, the composition comprises a population of isolated tumor infiltrating lymphcytes. In some embodiments, the composition comprises a population of CCR7+, CD62L+ central memory T cells. In some embodiments, the composition comprises a population of natural killer cells. In some embodiments, the composition comprises a population of CD4+CD25+ Foxp3+ regulatory T cells.

Also provided herein, in some aspects, are compositions comprising a polypeptide comprising a first syndecan-2 binding domain and a second syndecan-2 binding domain. Various embodiments of these compositions are recited below, contemplated as distinct or in combination. In some embodiments, the first syndecan-2 binding domain comprises an antibody variable domain that binds at least one mammalian syndecan-2 protein. In some embodiments, the antibody variable domain binds human syndecan-2. In some embodiments, the antibody variable domain binds a nonhuman mammalian syndecan-2. In some embodiments, the antibody variable domain specifically binds human syndecan-2. In some embodiments, the antibody variable domain is chimeric. In some embodiments, the antibody variable domain is humanized. In some embodiments, the second syndecan-2 binding domain is identical to the first syndecan-2 binding domain. In some embodiments, the second syndecan-2 binding domain comprises an amino acid residue sequence that is identical to the first syndecan-2 binding domain amino acid residue sequence. In some embodiments, the second syndecan-2 binding domain is different form the first syndecan-2 binding domain. In some embodiments, the second syndecan-2 binding domain comprises an amino acid residue sequence that differs from the first syndecan-2 binding domain amino acid residue sequence. In some embodiments, the composition comprises a physiologically acceptable buffer. In some embodiments, the physiologically acceptable buffer comprises at least one compound selected from the group consisting of maleic acid, tartaric acid, lactic acid, citric acid, acetic acid, sodium bicarbonate, sodium phosphate, histadine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitanmonooleate. In some embodiments, the physiologically acceptable buffer is suitable for intravenous administration. In some embodiments, the composition comprises an additional therapeutic agent. In some embodiments, the additional therapeutic agent comprises at least one autoimmune disease agent selected from the group consisting of a non-steroidal anti-inflammatory drug (NSAID), iburprofen, naproxen, meloxicam, etodolac, nabumetone, sulindac, tolementin, choline magnesium salicylate, diclofenac, diflusinal, indomethescin, ketoprofen, meloxicam, oxaprozin, piroxicam, celecoxib, etoricoxib, lumiracoxib, a corticosteroid, methotrexate, hydroxychloroquine, sulfasalazine, leflunomide, a TNFa inhibitor, etanercept, adalimumab, infliximab, certolizumab pegol, golimumab, abatacept, rituximab, tociluzumab, anakinra, cyclosporine, antithymocyte globulin, mycophenolate mofetil, and cyclosphomaide. In some embodiments, the additional therapeutic agent comprises at least one fibrosis disease agent selected from the group consisting of nintedanib, pirfenidone, a corticosteroid, albuterol, levabuterol, salmeterol, formoterol, flovent, and pulmicort. In some embodiments, the additional therapeutic agent comprises at least one cancer agent selected from the group consisting of methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar. In some embodiments, the additional therapeutic agent comprises at least one cancer agent selected from the group consisting of hydromorphone, levorphanol, methadone, morphine, oxycodone, hydrocodone, oxymorphone, fentanyl, dolasetron, granisetron, ondansetron, palonosetron, dexamethasone, methylpredinsolone, droperidol, haloperidol, metoclopramide, prochlorperazine, promethazine, lorazepam, alprazolam, dronabinol, nabilone, aprepitant, rolapitant, epoetin, darbepoetin, filgrastim, pegfilgrastim, and sargramostim. In some embodiments, the composition comprises a population of mammalian cells at least 30% of which are positive for syndecan-2. In some embodiments, the composition comprises a population of CART cells. In some embodiments, the composition comprises a population of isolated tumor infiltrating lymphcytes. In some embodiments, the composition comprises a population of CCR7+, CD62L+ central memory T cells. In some embodiments, the composition comprises a population of natural killer cells. In some embodiments, the composition comprises a population of CD4+CD25+ Foxp3+ regulatory T cells.

In additional aspects, there are provided, compositions comprising a polypeptide comprising at least 20 consecutive residues having at least 80% identity to a mammalian syndecan-2 protein polypeptide; and a pharmaceutically acceptable buffer. Various embodiments of these compositions are recited below, contemplated as distinct or in combination. In some embodiments, the polypeptide comprises at least 50 consecutive residues having at least 80% identity to a mammalian syndecan-2 extracellular domain. In some embodiments, the polypeptide comprises a polypeptide having at least 80% identity to a mammalian syndecan-2 extracellular domain. In some embodiments, the polypeptide comprises a polypeptide having at least 90% identity to a mammalian syndecan-2 extracellular domain. In some embodiments, the polypeptide comprises a polypeptide having at least 95% identity to a mammalian syndecan-2 extracellular domain. In some embodiments, the polypeptide comprises a polypeptide having at least 95% identity to human syndecan-2 extracellular domain. In some embodiments, the polypeptide comprises a polypeptide having a human syndecan-2 extracellular domain. In some embodiments, the physiologically acceptable buffer comprises at least one compound selected from the group consisting of maleic acid, tartaric acid, lactic acid, citric acid, acetic acid, sodium bicarbonate, sodium phosphate, histadine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitanmonooleate. In some embodiments, the physiologically acceptable buffer is suitable for intravenous administration. In some embodiments, the polypeptide does not comprise a full length mammalian syndecan-2 protein. In some embodiments, the polypeptide comprises a full length mammalian syndecan-2 protein. In some embodiments, wherein the polypeptide comprises a dimerization domain. In some embodiments, the dimerization domain comprises a Fc domain. In some embodiments, wherein the polypeptide comprises an additional therapeutic agent. In some embodiments, the additional therapeutic agent comprises at least one autoimmune disease agent selected from the group consisting of a non-steroidal anti-inflammatory drug (NSAID), iburprofen, naproxen, meloxicam, etodolac, nabumetone, sulindac, tolementin, choline magnesium salicylate, diclofenac, diflusinal, indomethescin, ketoprofen, meloxicam, oxaprozin, piroxicam, celecoxib, etoricoxib, lumiracoxib, a corticosteroid, methotrexate, hydroxychloroquine, sulfasalazine, leflunomide, a TNFa inhibitor, etanercept, adalimumab, infliximab, certolizumab pegol, golimumab, abatacept, rituximab, tociluzumab, anakinra, cyclosporine, antithymocyte globulin, mycophenolate mofetil, and cyclosphomaide. In some embodiments, the additional therapeutic agent comprises at least one fibrosis disease agent selected from the group consisting of nintedanib, pirfenidone, a corticosteroid, albuterol, levabuterol, salmeterol, formoterol, flovent, and pulmicort. In some embodiments, the additional therapeutic agent comprises at least one cancer agent selected from the group consisting of methotrexate (RHEUMATREX®, Amethopterin) cyclophosphamide (CYTOXAN®), thalidomide (THALIDO-MID®), acridine carboxamide, Actimid®, actinomycin, 17-N-allylamino-17-demethoxygeldanamycin, aminopterin, amsacrine, anthracycline, antineoplastic, antineoplastic, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar. In some embodiments, the additional therapeutic agent comprises at least one cancer agent selected from the group consisting of hydromorphone, levorphanol, methadone, morphine, oxycodone, hydrocodone, oxymorphone, fentanyl, dolasetron, granisetron, ondansetron, palonosetron, dexamethasone, methylpredinsolone, droperidol, haloperidol, metoclopramide, prochlorperazine, promethazine, lorazepam, alprazolam, dronabinol, nabilone, aprepitant, rolapitant, epoetin, darbepoetin, filgrastim, pegfilgrastim, and sargramostim. In some embodiments, wherein the composition comprises a population of mammalian cells at least 30% of which are positive for syndecan-2. In some embodiments, wherein the composition comprises a population of CAR T cells. In some embodiments, wherein the composition comprises a population of isolated tumor infiltrating lymphcytes. In some embodiments, wherein the composition comprises a population of CCR7+, CD62L+ central memory T cells. In some embodiments, wherein the composition comprises a population of natural killer cells. In some embodiments, wherein the composition comprises a population of CD4+CD25+ Foxp3+ regulatory T cells. In some embodiments, wherein the composition is for use in treating a disorder comprising Th17 misregulation. In some embodiments, wherein the composition is for use in treating at least one disorder selected from the list consisting of an autoimmune disorder and a cancer.

Also provided herein are methods of treating at least one disorder selected from the list consisting of an autoimmune disorder, fibrosis and a cancer, comprising the steps of identifying a subject in need of treatment for at least one disorder selected from the list consisting of an autoimmune disorder, a fibrotic disorder and a cancer; and administering a dosage regimen of a Th17 inhibitor to the subject. Various embodiments of these compositions are recited below, contemplated as distinct or in combination. In some embodiments, the administering comprises intravenously administering the dosage regimen. In some embodiments, the Th17 inhibitor comprises a syndecan-binding any of the above compositions. In some embodiments, the Th17 inhibitor comprises any of the above syndecan-binding compositions.

In some embodiments, the Th17 inhibitor comprises any of the above syndecan-2 polypeptide compositions. In some embodiments, the method comprises monitoring said disorder and adjusting said dosage regimen according to a response from said subject. In some embodiments, the Th17 inhibitor inhibits NFκB activity. In some embodiments, the Th17 inhibitor comprises an additional therapeutic agent. In some embodiments, the additional therapeutic agent comprises a population of mammalian cells at least 30% of which are positive for syndecan-2. In some embodiments, the additional therapeutic agent comprises a population of CAR T cells. In some embodiments, the additional therapeutic agent comprises a population of isolated tumor infiltrating lymphocytes. In some embodiments, the additional therapeutic agent comprises a population of CCR7+, CD62L+ central memory T cells. In some embodiments, the additional therapeutic agent comprises a population of natural killer cells. In some embodiments, the additional therapeutic agent comprises a population of CD4+CD25+ Foxp3+ regulatory T cells.

BRIEF DESCRIPTION OF THE DRAWINGS

Relevant features of the invention are set forth with particularity in the appended claims. A further understanding of the features and advantages of the present disclosure is obtained by reference to the following detailed description that sets forth illustrative embodiments, in which the principles of the invention are utilized, and the accompanying drawings of which:

FIG. 6, at left illustrates flow cytometry analysis of Sdc2$^+$CD271$^+$CD45$^-$ and Sdc2$^+$Sca1$^+$CD45$^-$ mononuclear cells from human and mouse bone marrow respectively. FIG. 6, center illustrates identification of Sdc2$^+$gp38$^+$CD45$^-$ stromal cells in mouse lymph nodes and thymus by flow cytometry analysis. FIG. 6, at right illustrates identification of Sdc2$^+$Sca1$^+$CD45$^-$ stromal cells in mouse adipose and muscle tissue by flow cytometry analysis.

FIG. 7A illustrates flow cytometry of dissected breast tumours from PyMT-ChOVA mice revealing Sdc2$^+$epithelial (mCherry$^{+ve}$ CD45$^{-ve}$), and Sdc2$^+$SC (mCherry$^{-ve}$, CD45$^{-ve}$, GP38$^{+ve}$). FIG. 7B illustrates immunohistochemistry revealing increased levels of Sdc2 protein in human breast tumours. FIG. 7C illustrates ELISA data demonstrating high levels of Sdc2 protein in serum of patients with basal-like breast cancer.

FIG. 8A illustrates ELISA data demonstrating high levels of Sdc2 in stromal cell-conditioned media (SC-CM). FIG. 8B illustrates that SC-CM enhances the migration of MDA-MB-231 breast cancer cells (BCC), and pre-incubation of BCC with recombinant Sdc2 enhances migration towards SC-CM. FIG. 8C illustrates that knockdown of Sdc2 inhibits the ability of BCC to migrate towards serum containing media. FIG. 8D illustrates flow cytometry of CFSE-labeled CD4$^+$ T cells, revealing CD3/CD28-mediated stimulation of proliferation is inhibited by SC overexpressing Sdc2.

FIG. 9A illustrates that MDA-MB-231 cells transduced with AdshSdc2 indicating an attenuated TGFβ-induced increase in SMAD7, PAI-1 and CTFG RNA when compared to control cells expressing empty vector (EV). RT-qPCR demonstrates efficient knockdown of Sdc2. FIG. 9B illustrates RT-qPCR and Western blot analysis demonstrating that Sdc2 knockdown attenuates TGFβ-mediated induction of EMT markers, SNAIL-1 and Fibronectin respectively.

FIG. 10A illustrates the generation of deletion mutants containing different functional domains of Sdc2. Fragments 1-6 contain the signal peptide, whereas fragments 7-8 do not. FIG. 10B illustrates that various Sdc2 functional fragments inhibit migration of MDA-MB-231 towards SC-CM in cis. FIG. 10C illustrates various Sdc2 functional fragments inhibit migration of MDA-MB-231 towards SC-CM in trans. (2-sided Students t-test *p<0.05) FIG. 10D illustrates various Sdc2 fragments significantly inhibit TNF-α/IL-1β-induced NF-κB activation.

DETAILED DESCRIPTION

Figure 1:
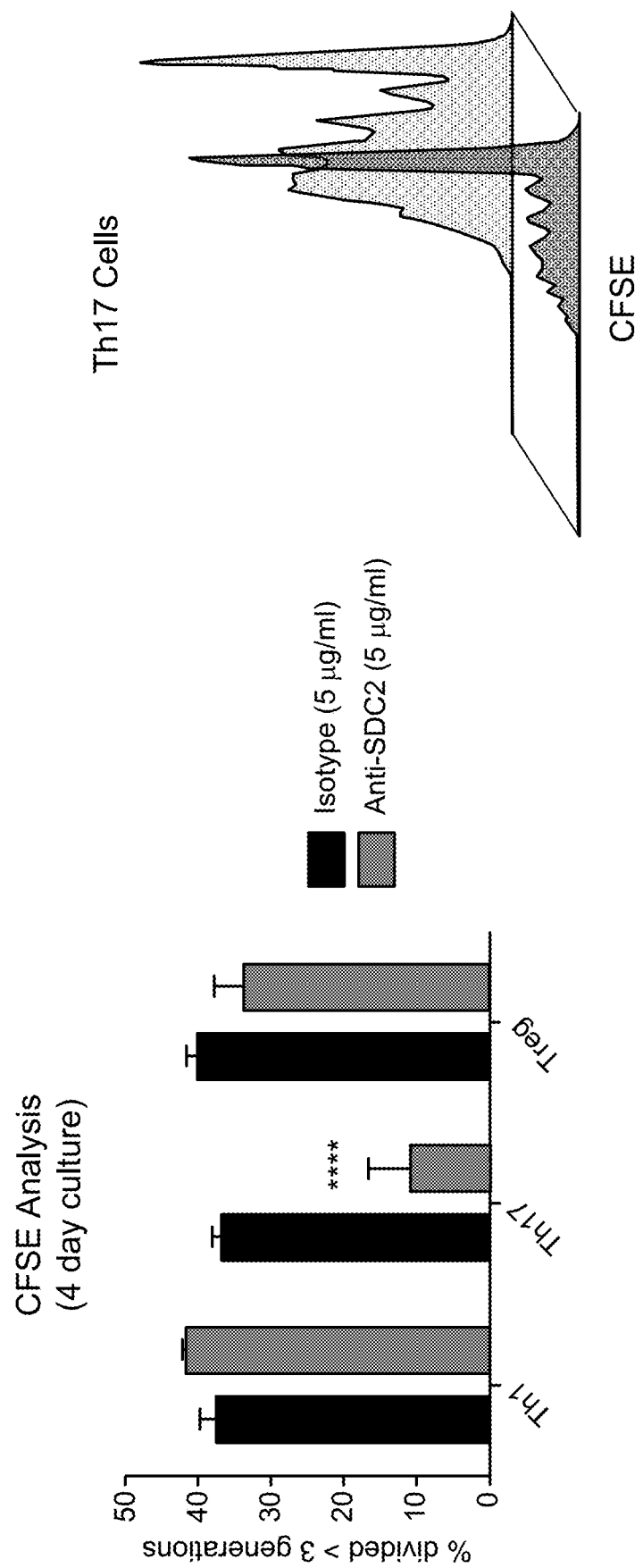
FIG. 1 illustrates a schematic of proliferation seen across cultures of Th1, Th17 and Treg cells.

Provided in the present disclosure are alternative agents and therapies for autoimmune disease, fibrosis, and cancer. Contemplated herein are agents and therapies comprising modulators of syndecan-2. Herein, it is illustrated that modulation of syndecan-2 (SDC2) expression and/or activity have effects that reduce or reverse key elements of autoimmune disease, fibrosis, and cancer.

Modulators and inhibitors of syndecan-2 are provided herein. Some such modulators include but are not limited to antibodies that bind to at least one epitope of syndecan-2 and fragments of syndecan-2 that act as an modulator or inhibitor of syndecan-2. Modulators of syndecan-2 are useful in treatment of diseases including but not limited to autoimmune disease, fibrosis, cancer, and other diseases where aberrant Th17 cell activity is suspected.

Modulators of Syndecan-2

In specific examples, described in more detail below, modulators of syndecan-2 are disclosed. In some cases, the modulator comprises a syndecan-2 binding domain, such that the modulator binds to syndecan-2 on the surface of a cell. In some cases the modulator comprises all or part of an antibody to syndecan-2. The modulator of syndecan-2, in some cases, comprises a first portion that binds to syndecan-2 and a second portion that forms a homodimer with itself. In use, this binds to cell-surface syndecan-2, leaving the second portion exposed and available to bind to another modulator that binds to cell-surface syndecan-2 in the vicinity. The homodimer formation results, in some cases, in 'cross-linking' of syndecan-2 proteins on the surface of a cell. Alternate embodiments bind Syndecan-2 in the absence of a homodimerization domain.

The first portion comprises a fragment of syndecan-2, suitably a fragment of the syndecan-2 extracellular domain. Examples of such fragments include C-terminal deletion fragments, internal fragments and N-terminal deletion fragments, and specific examples include peptides that correspond to amino acids 1-79; 1-87; 1-100; 1-144; 1-169; 1-201; 9-79; 19-87; 19-100; 19-144; 19-169; and 19-201 of human SDC-2. The second portion, when included in the modulator, comprises a dimerization domain, such as an Fc portion of a fragment thereof of an antibody, so as to facilitate formation of modulator dimers. Alternate modulators comprise first and second portions, both of which bind to syndecan-2. As a consequence of these structures, in some cases modulators individually or in aggregate bind to Syndecan-2 surface protein moieties and optionally bind such moieties to one another so as to 'crosslink' such moieties to one another on a single cell surface or among multiple cells.

Data from examples of the use of SDC2 polypeptide demonstrate the role of SDC2, such as fragments of syndecan-2 polypeptide, as a dominant negative inhibitor of the activity of native SDC2. Hence, the invention specifically provides SDC2 antagonists, such as at least a portion of a SDC2 polypeptide or an antibody to SDC2, for use as described herein.

In other embodiments, a modulator of syndecan-2 is a syndecan-2 inhibitory polynucleotide, such as a RNAi, a siRNA, a miRNA, or a shRNA polynucleotide. Such examples of polynucleotide modulators of syndecan-2 act in some cases to decrease syndecan-2 mRNA transcript levels or the rate of translation thereof thereby inhibiting syndecan-2.

Anti-Syndecan-2 Antibodies

Provided herein are antibodies to syndecan-2 (SDC2) for use as described herein, methods of treatment that use an antibody to SDC2, uses of an antibody to SDC2 and pharmaceutical compositions comprising an antibody to SDC2 for use as described herein in treatment of immune disease or fibrosis. Syndecan-2 antibodies are contemplated herein to bind to at least one epitope of a syndecan-2 protein on a cell surface. Specific anti-Syndecan-2 antibodies include an anti-syndecan-2 antibody, orb13481, reactive with at least human, mouse and rat, available from Biorbyt Ltd (12 Pembroke Avenue, Denny Industrial Centre, Waterbeach, Cambridge, CB25 9QR, UK) and SDC2 antibody, catalog number: MAB29651 (Clone 305507), available from R&D Systems, Inc, reactive with human, mouse, rat, equine, rabbit and pig.

Contemplated herein for uses and methods of treatment herein are fragments of syndecan-2 antibodies such as variable domains and syndecan-2 binding portions thereof of orb13481 and MAB29651, such as a VH domain or a VL domain of orb13481 or MAB29651. Alternatively, an anti-syndecan-2 antibody comprises a CDR domain of orb13481 or MAB29651, for example a VH-CDR1, VH-CDR2, VH-CDR3, VL-CDR1, VL-CDR2, or VL-CDR3 domain of orb13481 or MAB29651. Also contemplated herein are chimeric antibodies and humanized antibodies retaining known anti-Syndecan-2 antibody binding domains or binding activities, wherein these are inserted or otherwise introduced into a human or other recipient species antibody scaffold so as to reduce or minimize antibody antigenicity. Antibodies to SDC2 and fragments thereof as disclosed herein that retain the essential function of binding to and antagonizing SDC2 are also embraced within the term anti-SDC2 antibody.

Also contemplated herein are fusion proteins comprising a first portion and a second portion, the first portion comprising a syndecan-2 binding fragment of an anti-syndecan-2 antibody and the second portion comprising a dimerization domain. Contemplated herein, the first portion comprising syndecan-2 binding fragments comprises at least a portion of a VH domain or a VL domain of an anti-syndecan-2 antibody, for example for example a VH-CDR1, VH-CDR2, VH-CDR3, VL-CDR1, VL-CDR2, VL-CDR3 domain, or combinations thereof. Also contemplated herein, the second portion comprises a dimerization domain such as an Fc domain, leucine zipper domain, or any other dimerization known in the art. Fusion proteins comprising syndecan-2 binding fragments of a syndecan-2 antibody also include a first portion and a second portion, where the first and second portions comprise syndecan-2 binding fragments comprises at least a portion of a VH domain or a VL domain of an anti-syndecan-2 antibody, for example for example a VH-CDR1, VH-CDR2, VH-CDR3, VL-CDR1, VL-CDR2, VL-CDR3 domain, or combinations thereof.

The term "antibody" as used herein comprises derivatives or functional fragments thereof which still retain the binding specificity and preferably retain the ability modulate or inhibit syndecan-2 for example by cross-linking at least two cell surface syndecan-2 proteins. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig(s)) of different classes (i.e. IgA, IgG, IgM, IgD and IgE) and subclasses (such as IgG1, IgG2 etc.).

The term "antibody" also includes embodiments such as chimeric, single chain and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind an antigen or epitope independently of other V regions or domains. Such immunoglobulin single variable domains encompass not only an isolated antibody single variable domain polypeptide, but also larger polypeptides that comprise one or more monomers of an antibody single variable domain polypeptide sequence. Molecules that retain antibody binding to syndecan-2 and which form dimers resulting in cross-linking of syndecan-2 are included in the definition of antibodies for the invention.

Syndecan-2 Fragment Polypeptides

Contemplated herein are syndecan-2 fragment polypeptides that modulate or inhibit syndecan-2 activity. Modulation or inhibition is accomplished, for example, by binding to cell surface syndecan-2. Syndecan-2 fragment polypeptides, in some cases, act by cross-linking of syndecan-2 protein at the surface of a cell, optionally, to one or more syndecan-2 proteins on the surface of the same cell or a different cell, and hence to inhibition of Th17 and the desired therapeutic effect. In some cases, syndecan-2 fragment polypeptides bind cell surface syndecan-2 interfering with its ability to interact with receptors or ligands. Alternatively or in combination, syndecan-2 fragment polypeptides act by binding to syndecan receptors or ligands, preventing the receptors or ligands from interacting with full-length syndecan-2, such as is expressed and at least partially exposed on a cell surface.

Provided herein are fragments of syndecan-2, for example fragments of syndecan-2 that comprise at least a portion of the extracellular domain. Fragments of syndecan-2 comprise at least a consecutive series of amino acid residues comprising a portion of a syndecan-2 polypeptide sequence, such as a portion of a syndecan-2 polypeptide sequence as presented below (SEQ ID NO: 1)
MRRAWILLTLGLVACVSAESRAELTSDKDMYLDNSSIEEASGVYPIDDD

DYASASGSGADEDVESPELTTSRPLPKILLTSAAPKVETTTLNIQNKIP

AQTKSPEETDKEKVHLSDSERKMDPAEEDTNVYTEKHSDSLFKRTEVLA

AVIAGGVIGFLFAIFLILLLVYRMRKKDEGSYDLGERKPSSAAYQKAPT

KEFYA.

Fragment inhibitors of syndecan-2 comprise polypeptides having a portion of syndecan-2 polypeptide comprising at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% of the residues in the full-length polypeptide. In some cases, the residues are consecutive or co-linear with those of the full-length polypeptide. Alternately, in some cases regions are rearranged relative to one another's position in the full-length polypeptide. Fragments of syndecan-2 include any portion of the syndecan-2 polypeptide, including but not limited to amino acids at positions or having carboxy-terminal syndecan-2 residue sequence corresponding to the carboxy-terminus of a fragment of 1-200, 1-199, 1-198, 1-197, 1-196, 1-195, 1-194, 1-193, 1-192, 1-191, 1-190, 1-189, 1-188, 1-187, 1-186, 1-185, 1-184, 1-183, 1-182, 1-181, 1-180, 1-179, 1-178, 1-177, 1-176, 1-175, 1-174, 1-173, 1-172, 1-171, 1-170, 1-169, 1-168, 1-167, 1-166, 1-165, 1-164, 1-163, 1-162, 1-161, 1-160, 1-159, 1-158, 1-157, 1-156, 1-155, 1-154, 1-153, 1-152, 1-151, 1-150, 1-149, 1-148, 1-147, 1-146, 1-145, 1-144, 1-143, 1-142, 1-141, 1-140, 1-139, 1-138, 1-137, 1-136, 1-135, 1-134, 1-133, 1-132, 1-131, 1-130, 1-129, 1-128, 1-127, 1-126, 1-125, 1-124, 1-123, 1-122, 1-121, 1-120, 1-119, 1-118, 1-117, 1-116, 1-115, 1-114, 1-113, 1-112, 1-111, 1-110, 1-109, 1-108, 1-107, 1-106, 1-105, 1-104, 1-103, 1-102, 1-101, 1-100, 1-99, 1-98, 1-97, 1-96, 1-95, 1-94, 1-93, 1-92, 1-91, 1-90, 1-89, 1-88, 1-87, 1-86, 1-85, 1-84, 1-83, 1-82, 1-81, 1-80, 1-79, 1-78, 1-77, 1-76, 1-75, 1-74, 1-73, 1-72, 1-71, 1-70, 1-69, 1-68, 1-67, 1-66, 1-65, 1-64, 1-63, 1-62, 1-61, 1-60, 1-59, 1-58, 1-57, 1-56, 1-55, 1-54, 1-53, 1-52, 1-51, 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-201, or corresponding to or having an aminoterminal syndecan-2 fragment corresponding to the amino terminus of a syndecan-2 fragment of 2-201, 3-201, 4-201, 5-201, 6-201, 7-201, 8-201, 9-201, 10-201, 11-201, 12-201, 13-201, 14-201, 15-201, 16-201, 17-201, 18-201, 19-201, 20-201, 21-201, 22-201, 23-201, 24-201, 25-201, 26-201, 27-201, 28-201, 29-201, 30-201, 31-201, 32-201, 33-201, 34-201, 35-201, 36-201, 37-201, 38-201, 39-201, 40-201, 41-201, 42-201, 43-201, 44-201, 45-201, 46-201, 47-201, 48-201, 49-201, 50-201, 51-201, 52-201, 53-201, 54-201, 55-201, 56-201, 57-201, 58-201, 59-201, 60-201, 61-201, 62-201, 63-201, 64-201, 65-201, 66-201, 67-201, 68-201, 69-201, 70-201, 71-201, 72-201, 73-201, 74-201, 75-201, 76-201, 77-201, 78-201, 79-201, 80-201, 81-201, 82-201, 83-201, 84-201, 85-201, 86-201, 87-201, 88-201, 89-201, 90-201, 91-201, 92-201, 93-201, 94-201, 95-201, 96-201, 97-201, 98-201, 99-201, 100-201, 101-201, 102-201, 103-201, 104-201, 105-201, 106-201, 107-201, 108-201, 109-201, 110-201, 111-201, 112-201, 113-201, 114-201, 115-201, 116-201, 117-201, 118-201, 119-201, 120-201, 121-201, 122-201, 123-201, 124-201, 125-201, 126-201, 127-201, 128-201, 129-201, 130-201, 131-201, 132-201, 133-201, 134-201, 135-201, 136-201, 137-201, 138-201, 139-201, 140-201, 141-201, 142-201, 143-201, 144-201, 145-201, 146-201, 147-201, 148-201, 149-201, 150-201, 151-201, 152-201, 153-201, 154-201, 155-201, 156-201, 157-201, 158-201, 159-201, 160-201, 161-201, 162-201, 163-201, 164-201, 165-201, 166-201, 167-201, 168-201, 169-201, 170-201, 171-201, 172-201, 173-201, 174-201, 175-201, 176-201, 177-201, 178-201, 179-201, 180-201, 181-201, 182-201, 183-201, 184-201, 185-201, 186-201, 187-201, 188-201, 189-201, 190-201, 191-201, 192-201, 193-201, 194-201, 195-201, and 196-201 of human syndecan-2 or of another mammalian syndecan-2 family member. It is also contemplated that syndecan-2 fragment polypeptides comprise at least a portion of wildtype syndecan-2 having at least 10, 20, 30, 40, 50, 60, 70, 80, 90, 100, 110, 120, 130, 140, 150, 160, 170, 180, 190 or more than 190 amino acids of the full-length syndecan-2 polypeptide, for example having an amino terminus and carboxy terminus as indicated above or elsewhere herein. It is also contemplated that syndecan-2 fragment polypeptides comprise a portion of wildtype syndecan-2 having at least 10, 20, 30, 40, 50, 60, 70, 80, 90, 100, 110, 120, 130, 140, 150, 160, 170, 180, 190 or more than 190 amino acids of the full-length syndecan-2 polypeptide. It is also contemplated that syndecan-2 fragment polypeptides comprise a portion of wildtype syndecan-2 having no more than 10, 20, 30, 40, 50, 60, 70, 80, 90, 100, 110, 120, 130, 140, 150, 160, 170, 180, 190 or more than 190 amino acids of the full-length syndecan-2 polypeptide. Syndecan-2 fragments in some cases refers only to fragments that uniquely map to the family of Syndecan-2 molecules or a Syndecan-2 family molecule such as a human or other mammalian Syndecan-2 protein. Alternately, Syndecan-2 fragments in some cases refers only to fragments that uniquely map to a single species such as human Syndecan-2. Alternately, syndecan-2 fragments in some cases refers to any syndecan-2 fragment, independent of whether the fragment also maps to a non-syndecan-2 polypeptide. Syndecan-2 fragments in some cases comprise 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 1, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 consecutive residues of human or other mammalian syndecan-2 protein. Syndecan-2 fragment polypeptides are optionally contemplated to comprise an extracellular domain of syndecan-2 polypeptide comprising residues 19-144 of full-length wildtype syndecan-2, for example a polypeptide having the sequence (SEQ ID NO: 2)
ESRAELTSDKDMYLDNSSIEEASGVYPIDDDDYASASGSGADEDVESPEL
TTSRPLPKILLTSAAPKVETTTLNIQNKIPAQTKSPEETDKEKVHLSDSE
RKMDPAEEDTNVYTEKHSDSLFKRTE Optionally, fragments of syndecan-2, disclosed herein, include but are not limited to particular fragments recited herein. Nonhuman mammalian Syndecan-2 orthologues are similarly contemplated herein, both in full and as fragments described herein as above for human syndecan-2.

Full-length syndecan-2 and fragments of syndecan-2 are understood herein to include variants of syndecan-2. Variants herein include but are not limited to changes in the amino acid sequence of a syndecan-2 fragment that are found in some cases to change a train of the resultant molecule, such as to improve solubility, stability, potency, and other desirable traits in a syndecan-2 fragment known by one of skill in the art. Syndecan-2 fragment variants encompass derivatives or analogs in which (i) at least one amino acid residue is substituted with an amino acid residue that is not one encoded by the genetic code, (ii) the mature polypeptide is fused with another compound, such as polyethylene glycol or any other polypeptide residue modification known in the art, or (iii) additional amino acids are fused to the syndecan-2 fragment, such as a leader or secretory sequence or a sequence for purification of the polypeptide.

In some embodiments, the polypeptides described herein incorporate high affinity homologues or variants of syndecan-2 fragment polypeptides. Accordingly, the embodiments presented herein encompass syndecan-2 fragment polypeptides having a sequence that is similar to, but not identical to, the amino acid sequence of wildtype syndecan-2 fragment polypeptide. Thus, also contemplated within the scope of embodiments provided herein are syndecan-2 fragment polypeptides that have a sequence identity over the length of a syndecan-2 fragment linearly aligned with a wildtype syndecan-2 sequence using NCBI BLAST with default parameters provided, for example, at the NCBI webpage, demonstrate a percent identity of no more than, or no less than, about or exactly 99%, 98%, 97%, 96%, 95%, 94%, 93%, 92%, 91%, 90%, 89%, 88%, 87%, 86%, 85%, 84%, 83%, 82%, 81%, or 80% compared to the sequence of a portion of wildtype syndecan-2 fragment polypeptide. Some syndecan-2 fragment polypeptides are contemplated to include polypeptides having sequence wherein at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 1, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200, or more consecutive residues have 100%, 99%, 98%, 97%, 96%, 95%, 94%, 93%, 92%, 91%, 90%, 89%, 88%, 87%, 86%, 85%, 84%, 83%, 82%, 81%, or 80% identity to a portion of wildtype syndecan-2. Some syndecan-2 fragment polypeptides are contemplated to include polypeptides having sequence wherein no more than 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 1, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200, or more consecutive residues have 100%, 99%, 98%, 97%, 96%, 95%, 94%, 93%, 92%, 91%, 90%, 89%, 88%, 87%, 86%, 85%, 84%, 83%, 82%, 81%, or 80% identity to a portion of wildtype syndecan-2. Variant syndecan-2 fragment polypeptides are contemplated to include variant syndecan-2 fragment polypeptides which inhibit syndecan-2 activity with the same or better potency than the wildtype syndecan-2 fragment polypeptide.

Typical modifications of syndecan-2 fragments up to and including full length polypeptides include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are to a number of regions in syndecan-2 fragment polypeptides, including the peptide backbone, the side-chains, and the amino or carboxyl termini. Certain common peptide modifications that are useful for modification of syndecan-2 fragment polypeptides include glycosylation, lipid attachment, sulfation, gamma-carboxylation of glutamic acid residues, hydroxylation, blockage of the amino or carboxyl group in a polypeptide, or both, by a covalent modification, and ADP-ribosylation. Optionally, syndecan-2 fragment polypeptides are glycosylated, for example an O-linked heparin sulfate at residue 41, 55, and/or 57, and/or an O-linked acetylgalactosamine at residue 101; phosphorylated, for example at residue 115 and/or 187.

Moreover, one or more amino acids of the core sequence is altered, in a conservative manner such that the requisite binding is maintained or increased. Typical substitutions are made among the following groups of amino acids: (a) G, A, V, L and I; (b) G and P; (c) S, C, T, M; (d) F, Y, and W; (e) H, K and R; and (f) D, E, N, and Q. Other substitutions include the following groups: (i) S and T; (ii) P and G; a (iii) A, V, L and I.

Also contemplated within the scope of embodiments provided herein are modifications of the syndecan-2 polypeptide wherein the polypeptide is joined to another polypeptide with which it is not normally associated (e.g., Glutathione S-transferase (GST)-fusion protein, beta-galactosidase fusions, yeast two-hybrid GAL fusions, poly-His fusions, Ig fusions and the like). Thus, a syndecan-2 fragment polypeptide is optionally operatively linked, at either its N-terminus or C-terminus, to a heterologous polypeptide having an amino acid sequence not substantially homologous to the syndecan-2 fragment polypeptide. "Operatively linked" indicates that syndecan-2 fragment polypeptide and the heterologous polypeptide are both in-frame. Such a fusion protein alters (e.g., enhances, dampens) the ability of the syndecan-2 fragment polypeptide, or a functional variant thereof, to modulate syndecan-2 activity. Such a fusion protein alternatively alters (enhances, dampens) the pharmacokinetic half-life of the syndecan-2 fragment polypeptide in a human patient or experimental animal. The fusion protein, in some cases, alters the activity that the syndecan-2 fragment polypeptide imparts on myeloid cell activity including phagocytosis and ADCC.

Exemplary syndecan-2 fragment polypeptide fusion protein modulators and inhibitors include, for example fusion proteins comprising a first portion comprising a syndecan-2 fragment polypeptide and a homodimeric second portion. In some cases, the first portion binds to cell-surface syndecan-2, leaving the second portion exposed and available to bind to another modulator that binds to cell-surface syndecan-2 in the vicinity. The homodimer formation results again in cross-linking of the syndecan-2 on the cell surface or of syndecan-2 on two or more cells.

Optionally, the first portion comprises a fragment of syndecan-2, suitably a fragment of its extracellular domain, for example amino acids 19-144. Examples of such fragments include C-terminal deletion fragments, internal fragments and N-terminal deletion fragments, and specific examples are e.g. peptides that correspond to amino acids 1-79; 1-87; 1-100; 1-144; 1-169; 1-201; 9-79; 19-87; 19-100; 19-144; 19-169; 19-201 of human SDC-2.

Optionally, the second portion comprises a dimerization domain. Examples of dimerization domains include, Fc portion or a fragment thereof of an antibody, leucine-zipper dimerization domains or other domains sufficient for homodimerisation or heterodimerization.

Alternate modulators comprise first and second portions, both of which are fragments of syndecan-2 and in some cases, bind to syndecan-2 and a single modulator cross-links two SDC-2 surface proteins on a cell or joins two or more adjacent cells.

Syndecan-2 Inhibitory Polynucleotides

Provided herein are modulators of syndecan-2 comprising syndecan-2 inhibitory polynucleotides. Inhibitory polynucleotides herein include but are not limited to RNAi, siRNA, shRNA, miRNA, and the like. Such inhibitory polynucleotides are known in the art to decrease mRNA levels of a target gene, such as a syndecan-2 mRNA, thereby inhibiting the target gene, such as syndecan-2. Inhibitory polynucleotides comprise a sequence comprising at least a portion reverse-complementary to a syndecan-2 mRNA sequence. The cDNA corresponding to a reverse-transcribed syndecan-2 mRNA is presented below:

(SEQ ID NO: 3)
AGTCGCCCAGGGGAGCCCGGAGAAGCAGGCTCAGGAGGGAGGGAGCCAG

AGGAAAAGAAGAGGAGGAGAAGGAGGAGGACCCGGGGAGGGAGGCGCGG

CGCGGGAGGAGGAGGGGCGCAGCCGCGGAGCCAGTGGCCCCGCTTGGAC

GCGCTGCTCTCCAGATACCCCCGGAGCTCCAGCCGCGCGGATCGCGCGC

TCCCGCCGCTCTGCCCCTAAACTTCTGCCGTAGCTCCCTTTCAAGCCAG

CGAATTTATTCCTTAAAACCAGAAACTGAACCTCGGCACGGGAAAGGAG

TCCGCGGAGGAGCAAAACCACAGCAGAGCAAGAAGAGCTTCAGAGAGCA

GCCTTCCCGGAGCACCAACTCCGTGTCGGGAGTGCAGAAACCAACAAGT

GAGAGGGCGCCGCGTTCCCGGGGCGCAGCTGCGGGCGGCGGGAGCAGGC

GCAGGAGGAGGAAGCGAGCGCCCCGAGCCCCGAGCCCGAGTCCCCGAG

CCTGAGCCGCAATCGCTGCGGTACTCTGCTCCGGATTCGTGTGCGCGGG

CTGCGCCGAGCGCTGGGCAGGAGGCTTCGTTTTGCCCTGGTTGCAAGCA

GCGGCTGGGAGCAGCCGGTCCCTGGGGAATATGCGGCGCGCGTGGATCC

TGCTCACCTTGGGCTTGGTGGCCTGCGTGTCGGCGGAGTCGAGAGCAGA

GCTGACATCTGATAAAGACATGTACCTTGACAACAGCTCCATTGAAGAA

GCTTCAGGAGTGTATCCTATTGATGACGATGACTACGCTTCTGCGTCTG

GCTCGGGAGCTGATGAGGATGTAGAGAGTCCAGAGCTGACAACATCTCG

ACCACTTCCAAAGATACTGTTGACTAGTGCTGCTCCAAAAGTGGAAACC

ACGACGCTGAATATACAGAACAAGATACCTGCTCAGACAAAGTCACCTG

AAGAAACTGATAAAGAGAAAGTTCACCTCTCTGACTCAGAAAGGAAAAT

GGACCCAGCCGAAGAGGATACAAATGTGTATACTGAGAAACACTCAGAC

AGTCTGTTTAAACGGACAGAAGTCCTAGCAGCTGTCATTGCTGGTGGAG

TTATTGGCTTTCTCTTTGCAATTTTTCTTATCCTGCTGTTGGTGTATCG

CATGAGAAAGAAGGATGAAGGAAGCTATGACCTTGGAGAACGCAAACCA

TCCAGTGCTGCTTATCAGAAGGCACCTACTAAGGAGTTTTATGCGTAAA

ACTCCAACTTAGTGTCTCTATTTATGAGATCACTGAACTTTTCAAAATA

AAGCTTTTGCATAGAATAATGAAGATCTTTGTTTTTTGTTTTCATTAAA

GAGCCATTCTGGCACTTTAATGATAAAATCCCATTGTATTTAAAACATT

TCATGTATTTCTTTAGAACAACATAAAATTAAAATTTAACATCTGCAGT

GTTCTGTGAATAGCAGTGGCAAAATATTATGTTATGAAAACCCTCGATG

TTCATGGAATTGGTTTAAACTTTTATGCGCAAATACAAATGATTGTCT

TTTTCCTATGACTCAAAGATGAAAGCTGTTTCATTTGTGTCAGCATGTC

TCAGATTGACCTTACCAAGTTGGTCTTACTTTGTTAATTTATCTGTTGT

CCCCTTCCTCTCCTCTGCCCTCCCTTCTTGTGCCCTTAAAACCAAACCC

TATGCCTTTTGTAGCTGTCATGGTGCAATTTGTCTTTGGAAAATTCAGA

TAATGGTAATTTAGTGTATATGTGATTTTCAAATATGTAAACTTTAACT

TCCACTTTGTATAAATTTTTAAGTGTCAGACTATCCATTTTACACTTGC

TTTATTTTTCATTACCTGTAGCTTTGGGCAGATTTGCAACAGCAAATTA

```
-continued
ATGTGTAAAATTGGATTATTACTACAAAACCGTTTAGTCATATCTATCT

AATCAGATCTTCTTTTGGGAGGATTTGATGTAAGTTACTGACAAGCCTC

AGCAAACCCAAAGATGTTAACAGTATTTTAAGAAGTTGCTGCAGATTCC

TTTGGCCACTGTATTTGTTAATTTCTTGCAATTTGAAGGTACGAGTAGA

GGTTTAAAGAAAAATCAGTTTTTGTTCTTAAAAATGCATTTAAGTTGTA

AACGTCTTTTTAAGCCTTTGAAGTGCCTCTGATTCTATGTAACTTGTTG

CAGACTGGTGTTAATGAGTATATGTAACAGTTTAAAAAAAAGTTGGTA

TTTTATAAGCACAGACAATTCTAATGGTAACTTTTGTAGTCTTATGAAT

AGACATAAATTGTAATTTGGGAACATAAAAACTACTGAATAAATCATGT

GGCCTAATATTGAAAATGTCACTGTTATAAATTTTGTACATTTTTGATC

AAATGTACATCTCCCCTTTGCTAACGGCCGTCTGCTCTCAAGGATGACG

TGGGTTTGATTTCTAAGTGTTTCACAGTGTCTGTAAATCAAGACCAAAG

AGCCTGTCGATGAGACTGTTTATTACCAGATTCACTTCTGAATTGGCCA

GAGGAAATCTGAATGTATTATCCTGTGTGTGTCTAGGTAGAGATATTGG

AAGGCTGCCAGGGGATTTCGAAGTTTGCAACCTTTATAGGATAACTGAT

GGCAATATTAAGACAGACGCCTGCTTTTGCAAATAACTTACAAGACTGT

AAATTCCAAAGATCTGAATGGGGCTTTCCTGATGTTGGTATCTAAGGCT

TAGGCCTATAGATTGATTTACCTTTGGAATTGTGCTCCAAATGTCTACT

GAAGCTTAACCGAAGAACTAATAAATGGACTACAGTAGCTCACGTTACA

GGGAAGGAGGGTAGGCAGGGAGGCTCTGTGTGTTAAAATGAGGGTCTCA

CTGCTTTAGGATTGAAGTGGCTGGAAAGAGTGATGCCTGGGGAAGGAGA

TGGAGTTATGAGGGTACTGTGGCTGGTACTTTCTGTACTAAACATTTCC

TTTTTCTATTTTACCACTAATTTTGTTTTAAACTGTGAGCCGTCCAAGT

CAGAAGAAGACAGCAAAAAAAGCAACTTTTCCAACATACAATTTACTTT

TAATAAAGTATGAATATTTCATTTTGAGAACATTCCCTGGAATTGCCAC

ATAATTCATTAAAAACATTTTTTTAAGCAACACTTGGAACAGTGTTTAC

TTTAAATCCTTAATGGCCTTAATTAATTCTCAGATTCCTGCCCCATCAC

TTACAGAACCAATTCACTTTAGAGTGACTAAAAGGAAACGATAGCCTAG

CTTTCTAAAGCCACGCTGTGTCCCTCAATTACAGAGGGTAGGAATGGGT

ATACCTCTAACTGTGCAAAGCAGAGTGAAATTCAATTCATAGAATAACA

ACTGCTGGGAATATCCGTGCCAGGAAAAGAAAAATTTCTGGCAAATATT

TTGTCACTGCTGTAAAGCAAAATATTTGTGAAAGTGCCAAAATAAAGTC

TGTCATGCCAAAAGTAAATCATTGTATAGACTGACATCCAGTTTTCTTC

AACTGT.
```

Inhibitory polynucleotides are provided as a duplexed RNA (siRNA, miRNA) or a vector expressing a RNA that forms a hairpin structure (shRNA). Inhibitory polynucleotides are generally formulated in liposomal nanoparticle formulations and other formulations that allow delivery of the inhibitory polynucleotide to the target cell or tissue and increase serum half-life and stability. Similarly, inhibitory polynucleotides are contemplated comprising a span of consecutive bases spanning at least, at most, about or exactly 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% of the above-cited human SDC2 transcript or alternately of a syndecan-2 transcript of a mammalian syndecan-2 orthologue. In some cases the span of consecutive bases uniquely maps to human syndecan-2. In some cases the span of consecutive bases uniquely maps to a nonhuman mammalian syndecan-2 orthologue. In some cases the span of consecutive bases uniquely maps the mammalian syndecan-2 family. In some cases the span of consecutive bases also maps non syndecan-2 sequences.

Syndecan-2 Modulator Compositions

Contemplated herein are syndecan-2 modulator and antagonist compositions comprising a syndecan-2 modulator or antagonist herein and one or more pharmaceutically acceptable component, such as a pharmaceutically acceptable carrier, suitable for administration to a subject. Pharmaceutically acceptable carriers, such as buffers, salts, and excipients, include any and all solvents, dispersion media, coatings, antibacterial and antifungal agents, tonicifiers, and absorption delaying agents, and the like that are physiologically compatible. Examples of pharmaceutically acceptable carriers include one or more of water, saline, phosphate buffered saline, dextrose, glycerol, ethanol, and the like, as well as combinations thereof. Pharmaceutically acceptable carriers optionally comprise substances such as wetting or emulsifying agents, preservatives, or buffers, which enhance the self-life or effectiveness of the syndecan-2 modulators and antagonists. Pharmaceutically acceptable buffers are contemplated to include maleic acid, tartaric acid, lactic acid, citric acid, acetic acid, sodium bicarbonate, sodium phosphate, histadine, glycine, and combinations thereof. Pharmaceutically acceptable salts are contemplated to include sodium chloride, potassium chloride, calcium chloride, zinc chloride, and combinations thereof. Pharmaceutically acceptable excipients are contemplated to include water, dextrose, N-methylpyrrolidone, dimethyl sulfoxide, N,N-dimethylacetamide, ethanol, propylene glycol, polyethylene glycol, diethylene glycol monoethyl ether, surfactant polyoxyethylene-sorbitanmonooleate, and combinations thereof. Often, the administration is intraveinous administration; accordingly, preferred carriers are pharmaceutically acceptable carriers consistent with intraveinous administration.

Syndecan-2 modulator and antagonist compositions are contemplated to optionally contain a therapeutically effective amount of a syndecan-2 modulator or antagonist. Therapeutically effective amounts or dosages are contemplated to include dosages of 0.01 mg to 20 mg, for example, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of 0.1 mg to 2.0 mg.

Syndecan-2 modulator and antagonist compositions are contemplated to optionally contain a therapeutically effective amount of a syndecan-2 modulator or antagonist. Therapeutically effective amounts or dosages are contemplated to include dosages of about 0.01 mg to about 20 mg, for example, about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of about 0.1 mg to about 2.0 mg. As used herein "about" is understood to include values plus or minus 10% of the indicated value.

Syndecan-2 modulator and antagonist compositions are also contemplated to optionally comprise at least one additional therapeutic agent useful in treating autoimmune disease. Therapeutic agents useful in treating autoimmune disease include but are not limited to non-steroidal anti-inflammatory drugs (NSAID), iburprofen, naproxen, meloxicam, etodolac, nabumetone, sulindac, tolementin, choline magnesium salicylate, diclofenac, diflusinal, indomethescin, ketoprofen, meloxicam, oxaprozin, piroxicam, celecoxib, etoricoxib, lumiracoxib, a corticosteroid, methotrexate, hydroxychloroquine, sulfasalazine, leflunomide, a TNFa inhibitor, etanercept, adalimumab, infliximab, certolizumab pegol, golimumab, abatacept, rituximab, tociluzumab, anakinra, cyclosporine, antithymocyte globulin, mycophenolate mofetil, and cyclosphomaide.

Syndecan-2 modulator and antagonist compositions are also contemplated to optionally comprise at least one additional therapeutic agent useful in treating fibrosis. Therapeutic agents useful in treating fibrosis include but are not limited to nintedanib, pirfenidone, a corticosteroid, albuterol, levabuterol, salmeterol, formoterol, flovent, and pulmicort.

Syndecan-2 modulator and antagonist compositions are also contemplated to optionally comprise at least one additional therapeutic agent useful in treating cancer. Therapeutic agents useful in treating cancer include but are not limited to methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar. Optionally, syndecan-2 modulator and antagonist compositions comprise or are packaged with a therapeutic agent useful in relieving at least one side-effect of anti-cancer therapeutic, some such therapeutic agents include hydromorphone, levorphanol, methadone, morphine, oxycodone, hydrocodone, oxymorphone, fentanyl, dolasetron, granisetron, ondansetron, palonosetron, dexamethasone, methylpredinsolone, droperidol, haloperidol, metoclopramide, prochlorperazine, promethazine, lorazepam, alprazolam, dronabinol, nabilone, aprepitant, rolapitant, epoetin, darbepoetin, filgrastim, pegfilgrastim, and sargramostim.

The modulators and antagonists of the invention are optionally also be used in combination with cell therapies for various diseases. Accordingly the invention further provides a composition comprising a modulator of or antagonist of syndecan-2 combined for use according to earlier aspects of the invention in treatment of autoimmune disease or fibrosis, in combination with a population of mammalian cells at least 30% of which are positive for syndecan-2. Similarly, in some cases compositions herein comprise, for example regulatory T cells such as CD4+, CD25+, Foxp3+ regulatory cells, in particular for as therapy for autoimmune indications. Similarly, in some cases compositions herein comprise, for example tumour infiltrating lymphocyte (TIL) cells, in particular as therapy for oncology indications. Similarly, in some cases compositions herein comprise, for example engineered stem central memory T (CCR7+, CD62L+) cells, in particular as therapy for oncology indications. Similarly, in some cases compositions herein comprise, for example engineered CD8+ T cell clones, for example as derived from stem central memory T (CCR7+, CD62L+) cells, in particular as therapy for oncology indications. Similarly, in some cases compositions herein comprise, for example engineered CAR-T cell therapy cells, in particular as therapy for oncology indications. Similarly, in some cases compositions herein comprise, for example engineered TCR-T cell therapy cells, in particular as therapy for oncology indications. Similarly, in some cases compositions herein comprise, for example engineered Natural Killer (NK) cell therapy cells, in particular as therapy for oncology indications. Alternately, compositions are administered separately but in combination with cells as mentioned above as part of a treatment regimen.

The cells used in the therapy are generally mouse, rat, equine or human cells, preferably human cells. In embodiments of such therapies, 40% or more or 50% or more or 75% or more of the mammalian cell population are positive for syndecan-2. Further elements of suitable cell therapies, for use in combination with the modulator/antagonist therapies herein are described in WO2013/117761, which is hereby incorporated by reference in its entirety, and in US2014/0356398, published Dec. 4, 2014, which is hereby incorporated by reference in its entirety. In some embodiments of such therapies, therapeutic cells include, for example, regulatory T cells such as CD4+, CD25+, Foxp3+ regulatory T cells, tumour infiltrating lymphocyte (TIL) cells, stem central memory T cells such as CCR7+, CD62L+ cells, cd8+t cell clones derived from central memory cells, CAR-T cells, TCR-T cells or Natural Killer (NK) cells.

Compositions in some cases comprise cells, or are in some cases co-administered with cells as disclosed herein. Compositions variously comprise at least 100 cells, 1,000, cells, 10,000 cells, 100,000 cells, 1,000,000 cells, 10,000, 000 cells, 100,000,000 cells, 1,000,000,000 cells, or more than 1 billion cells. Co-administration variously comprises administration of at least 100 cells, 1,000, cells, 10,000 cells, 100,000 cells, 1,000,000 cells, 10,000,000 cells, 100,000, 000 cells, 1,000,000,000 cells, or more than 1 billion cells. Methods and Compositions in Treatment of Autoimmune and Inflammatory Disease Provided herein are modulators of syndecan-2 for use in treatment of disease, such as autoimmune and inflammatory disease in a patient identified as in need of such treatment. Such modulators of syndecan-2 relieve, reduce, or eliminate at least one symptom of an autoimmune or inflammatory disease. Modulators of syndecan-2 act, at least in part, by inhibiting Th17 cell activity.

Treatment is achieved in embodiments herein using modulator compounds or molecules or compositions that act by binding to cell surface syndecan-2. It has been observed that this leads, in some examples herein, to cross-linking of cell surface syndecan-2, and hence to inhibition of Th17 and the desired therapeutic effect. In some cases, modulator compounds bind cell surface syndecan-2 interfering with its ability to interact with receptors or ligands. In some cases, modulator compounds bind at least one syndecan-2 binding protein or receptor, interfering with its ability to interact with syndecan-2.

Described in more detail below, the modulator is, in some cases, an antibody to syndecan-2. Alternately, the modulator comprises a variable domain or a variable domain region that binds specifically to human syndecan-2, or a mammalian syndecan-2 orthologue.

Also contemplated herein are modulators of syndcan-2 that comprise fragments of syndecan-2, for example fragments of syndecan-2 that comprise at least a portion of the extracellular domain, comprising, for example amino acids 19-144 of a full-length wildtype syndecan-2. Examples of fragments of syndecan-2 include C-terminal deletion fragments, internal fragments and N-terminal deletion fragments, and specific examples are e.g. peptides that correspond to amino acids 1-79; 1-87; 1-100; 1-144; 1-169; 1-201; 9-79; 19-87; 19-100; 19-144; 19-169; 19-201 of human SDC-2.

Other compositions that inhibit are also disclosed herein, for example fusion proteins comprising fragments of syndecan-2. Modulators of syndecan-2 comprise a first portion that binds to syndecan-2 and a homodimeric second portion. In use, the first portion binds to cell-surface syndecan-2, leaving the second portion exposed and available to bind to another modulator that binds to cell-surface syndecan-2 in the vicinity. The homodimer formation results again in cross-linking of the syndecan-2 on the cell surface.

Optionally, the first portion comprises a fragment of syndecan-2, suitably a fragment of its extracellular domain, for example amino acids 19-144. Examples of such fragments include C-terminal deletion fragments, internal fragments and N-terminal deletion fragments, and specific examples are e.g. peptides that correspond to amino acids 1-79; 1-87; 1-100; 1-144; 1-169; 1-201; 9-79; 19-87; 19-100; 19-144; 19-169; 19-201 of human SDC-2.

Optionally, the second portion comprises a dimerization domain. Examples of dimerization domains include, Fc portion or a fragment thereof of an antibody sufficient for homodimerisation.

Alternate modulators comprise first and second portions, both of which bind to syndecan-2—such that a single modulator cross-links two SDC-2 surface proteins on a cell or joins two or more adjacent cells having SDC2 or syndecan-2 protein on their surfaces.

In embodiments provided herein, the effect of the modulator is to counter the activity of syndecan-2. Hence provided herein are antagonists of syndecan-2, such as inhibitors of syndecan-2 activity. Such antagonists of syndecan-2 are beneficial in treatment or alleviation of symptoms of autoimmune disease, such as those treated or alleviated via inhibition of Th17 cell activity. Antagonist activity is contemplated, in some cases, to be achieved via binding to cell surface syndecan-2 proteins, and in some cases through the creation of doubly bound or dimerized 'cross-links' between cell surface syndecan-2.

Modulators provided herein treat or alleviate the symptoms of autoimmune diseases, for example autoimmune and inflammatory diseases that are characterised by elevated levels of Th17 lymphocytes and IL-17 protein. More specifically, the autoimmune disease treated is selected from at least one of psoriasis, rheumatoid arthritis, juvenile rheumatoid arthritis, osteoarthritis, psoriatic arthritis, systemic lupus erythematosus, ulcerative colitis, Crohn's disease, inflammatory bowel disease, asthma, acute respiratory distress syndrome and multiple sclerosis. The modulators provided herein are alternatively also be used to treat autoimmune diseases, including but not limited to, ankylosing spondylitis, Type 1 diabetes, Hashimoto's thyroiditis, polymyalgia rheumatic, reactive arthritis (Reiter syndrome), sarcoidosis, scleroderma, Sjögren's syndrome, Hidradenitis suppurativa, encephalomyelitis, myasthenia gravis, autoimmune thyroiditis, atopic dermatitis, eczematous dermatitis, aphthous ulcer, iritis, conjunctivitis, keratoconjunctivitis, cutaneous lupus erythematosus, scleroderma, vaginitis, proctitis, erythema nodosum leprosum, autoimmune uveitis, allergic encephalomyelitis, acute necrotizing hemorrhagic encephalopathy, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, uveitis posterior, autoimmune polyglandular syndrome, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome, and Behcet's disease.

Some treatments provided herein relieve or alleviate at least one symptom of an autoimmune disease. Symptoms of autoimmune diseases vary depending on the type of autoimmune disease. Some such symptoms are known in the art and include but are not limited to at least one of pain, swelling, fever, rash, fatigue, malaise, diarrhea, bloating, gas, low blood count, osteoporosis, dry mouth, dry eyes, vision loss, impaired coordination, reduced spine flexibility, increased blood sugar, increased thirst, frequent urination, hunger, blurred vision, hair loss, weight loss, muscle pain, joint pain, headache, difficulty breathing, and jaw pain.

Compositions comprising modulators disclosed herein are contemplated. These compositions are used in the disclosed treatments, specifically the recited autoimmune diseases.

Also provided herein are methods of treatment of autoimmune disease, comprising administering to a patient in need thereof an amount of a modulator of syndecan-2 or an antagonist of syndecan-2 effective to inhibit Th17 cell activity. Specific autoimmune diseases are as elsewhere recited. The modulators and antagonists are similarly as elsewhere described; hence for example the modulator or antagonist binds to cell surface syndecan-2, resulting in cross-linking of syndecan-2. Some methods comprise administering an antibody to syndecan-2. Often, the administration is intraveinous administration.

Methods of treatment of autoimmune diseases or disorders comprise administration of a composition herein to a patient in need of alleviation of symptoms. Often, a subject is identified as presenting symptoms of an autoimmune disorder and is selected to receive the treatment comprising a composition as disclosed herein. A composition recited herein is administered to the subject. Administration is intravenous in many preferred embodiments, but alternate routes of administration such as surface administration, or otherwise directly contacting the target tissue are also contemplated. Alternative to intraveinous administration, in some cases compositions are administered locally or systemically, as a salve, lotion or emulsion, are injected, are surgically introduced, are ingested, are administered topically, orally, bucaly, nasally, or are introduced into a cavity of the subject. Compositions are administered singly, or over a time course, such as daily, multiple times weekly, weekly, biweekly, monthly or less frequently. Compositions are administered alone or in concert with additional measures that are in some cases related to treatment of the disorder, such as dietary supplement or adjustment, exercise or other treatment. Administration occurs during or between meals, and is independent of or alternately dependent upon daily administration timing, such as morning administration, evening administration, or multiple administrations relative to sleep, meals or exercise.

In some cases a subject in need of treatment is monitored prior to administration of a composition as presented herein. Symptoms are identified and their severity is assessed. The composition as described herein is administered alone or in combination with additional measures, singly or multiply over time as discussed herein or known to one of skill in the art. The subject is optionally monitored such that the efficacy of the treatment regimen is determined. Optionally, a treatment regimen is modified in response to preliminary treatment outcomes, such that treatment dose or frequency or does and frequency is altered so as to attain a desired level of subject response in light of symptom alleviation, side effect reduction, or a combination of symptom alleviation and side effect reduction. In some cases a report is produced prior to, during, following or prior to, during and following a treatment regimen, and is provided to a doctor, health care practitioner, insurer and/or subject or subject's representative.

The modulators and antagonists disclosed herein are optionally also be used in combination with cell therapies for various diseases. Accordingly, further provided are compositions comprising a modulator of or antagonist of syndecan-2, in combination with a population of mammalian cells at least 30% of which are positive for syndecan-2. Also provided herein are compositions comprising a modulator of or antagonist of syndecan-2 combined with a population of therapeutic cells, such as CD4+CD25+ Foxp3+ regulatory T cells. In some cases the cells are administered as a single composition in combination with a modulator or antagonist disclosed herein. Alternately or in combination, in some cases the cells are administered separately or through a separate route of administration relative to a modulator or antagonist disclosed herein.

The cells used in the therapy are generally mouse, rat, equine or human cells, preferably human cells. In embodiments of such therapies, 40% or more or 50% or more or 75% or more of the mammalian cell population are positive for syndecan-2. Further elements of suitable cell therapies, for use in combination with the modulator/antagonist therapies herein are described in WO2013/117761, which is hereby incorporated by reference in its entirety.

Syndecan-2 modulator and antagonist compositions are contemplated to optionally contain a therapeutically effective amount of a syndecan-2 modulator or antagonist. Therapeutically effective amounts or dosages are contemplated to include dosages of 0.01 mg to 20 mg, for example, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of 0.1 mg to 2.0 mg.

Syndecan-2 modulator and antagonist compositions are contemplated to optionally contain a therapeutically effective amount of a syndecan-2 modulator or antagonist. Therapeutically effective amounts or dosages are contemplated to include dosages of about 0.01 mg to about 20 mg, for example, about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of about 0.1 mg to about 2.0 mg. As used herein "about" is understood to include values plus or minus 10% of the indicated value.

Methods and Compositions in Treatment of Fibrosis

Modulators of syndecan-2, such as those provided herein, are contemplated for therapy against fibrosis such as that associated with disease. Hence, provided herein are modulators of syndecan-2 for use in treatment of fibrosis. In examples, set out below in more detail, a modulator acts in treating fibrosis in diseases by inhibiting Th17 activity.

Specifically, treatment is achieved in some embodiments herein using at least one modulator compound, molecule, or composition that acts by binding to syndecan-2, such as cell surface syndecan-2. It has been observed that this leads in examples to cross-linking of cell surface syndecan-2, and hence to inhibition of Th17 and the desired therapeutic anti-fibrosis effect.

Contemplated herein, the effect of the modulator is to counter the activity of syndecan-2. Hence there is provided an antagonist of syndecan-2 for use in treatment of fibrosis by inhibiting Th17 cell activity. Antagonist activity is typically achieved via binding to cell surface syndecan-2 and creation of cross-links between cell surface syndecan-2. Antibodies are used as antagonists, as described elsewhere herein. Also contemplated herein, are fragments of syndecan-2, which are optionally used as modulators and antagonists, as described in the present disclosure.

The modulator of or an antagonist of syndecan-2 for use as provided herein is for treating fibrosis in general, such as one or more of fibrotic diseases of the lung, fibrotic diseases of the liver and fibrotic diseases of the heart.

Examples of fibrosis in the lung include pulmonary fibrosis, idiopathic pulmonary fibrosis and cystic fibrosis. An example of liver fibrosis is liver cirrhosis. Examples of heart fibrosis include endomyocardial fibrosis, old myocardial infarction and atrial fibrosis. Other diseases comprising fibrosis that are treatable by the invention include mediastinal fibrosis, myelofibrosis (bone marrow), retroperitoneal fibrosis (soft tissue of the retroperitoneum), progressive massive fibrosis (in the lungs, a complication of coal workers' pneumoconiosis), nephrogenic systemic fibrosis (affecting the skin), Crohn's disease (affecting intestine), keloid diseases of the skin, scleroderma/systemic sclerosis (affecting skin and lungs), arthrofibrosis (knee, shoulder, other joints), Peyronie's disease (penis), Dupuytren's contracture (hands, fingers), and some forms of adhesive capsulitis (shoulder).

Some treatments provided herein relieve or reduce at least one symptom of fibrosis. Symptoms of fibrosis are variable depending on the type of fibrosis. Some such symptoms are known in the art and include but are not limited to shortness of breath, dry hacking cough, shallow breathing, weight loss, fatigue, joint pain, muscle pain, clubbing of the fingers and/or the toes, liver dysfunction, heart dysfunction, and other organ failure due to fibrosis.

Compositions comprising the modulator are further provided by the invention. These are for use in the disclosed fibrosis treatments, specifically the recited diseases of fibrosis.

The invention also provides a method of treatment of fibrosis, comprising administering to a patient in need thereof an amount of a modulator of syndecan-2 or an antagonist of syndecan-2 effective to inhibit Th17 cell activity. Often, the administration is intravenous administration. Specific fibrosis diseases are as elsewhere recited. The modulators and antagonists are similarly as elsewhere described; hence for example the modulator or antagonist bind to cell surface syndecan-2, resulting in cross-linking of syndecan-2. One method comprises administering an antibody to syndecan-2.

Methods of treatment of fibrosis diseases or disorders comprise administration of a composition herein to a patient in need of alleviation of symptoms. Often, a subject is identified as presenting symptoms of a fibrosis disease or disorder and is selected to receive the treatment comprising a composition as disclosed herein. A composition recited herein is administered to the subject. Administration is intravenous, in many preferred embodiments, but alternate routes of administration such as surface administration, or otherwise directly contacting the target tissue are also contemplated. Compositions are administered locally or systemically, as a salve, lotion or emulsion, are injected, are surgically introduced, are ingested, are administered topically, orally, bucaly, nasally, or are introduced into a cavity of the subject. Compositions are administered singly, or over a time course, such as daily, multiple times weekly, weekly, biweekly, monthly or less frequently. Compositions are administered alone or in concert with additional measures that are in some cases related to treatment of the disorder, such as dietary supplement or adjustment, exercise or other treatment. Administration occurs during or between meals, and is independent of or alternately dependent upon daily administration timing, such as morning administration, evening administration, or multiple administrations relative to sleep, meals or exercise.

In some cases a subject in need of treatment is monitored prior to administration of a composition as presented herein. Symptoms are identified and their severity is assessed. The composition as described herein is administered alone or in combination with additional measures, singly or multiply over time ad discussed herein or known to one of skill in the art. The subject is optionally monitored such that the efficacy of the treatment regimen is determined. Optionally, a treatment regimen is modified in response to preliminary treatment outcomes, such that treatment dose or frequency or does and frequency is altered so as to attain a desired level of subject response in light of symptom alleviation, side effect reduction, or a combination of symptom alleviation and side effect reduction. In some cases a report is produced prior to, during, following or prior to, during and following a treatment regimen, and is provided to a doctor, health care practitioner, insurer and/or subject or subject's representative.

The modulators and antagonists disclosed herein are optionally also be used in combination with cell therapies for various diseases. Accordingly further provided is a composition comprising a modulator of or antagonist of syndecan-2 combined for use according to earlier aspects herein in treatment of fibrosis, in combination with a population of mammalian cells at least 30% of which are positive for syndecan-2. Also provided herein, is a composition comprising a modulator of or antagonist of syndecan-2 combined with a population of CD4+CD25+ Foxp3+ regulatory T cells. In some cases the cells are administered as a single composition in combination with a modulator or antagonist disclosed herein. Alternately or in combination, in some cases the cells are administered separately or through a separate route of administration relative to a modulator or antagonist disclosed herein.

The cells used in the therapy are generally mouse, rat, equine or human cells, preferably human cells. In embodiments of such therapies, 40% or more or 50% or more or 75% or more of the mammalian cell population are positive for syndecan-2. Further elements of suitable cell therapies, for use in combination with the modulator/antagonist therapies herein are described in WO2013/117761, which is hereby incorporated by reference in its entirety.

Syndecan-2 modulator and antagonist compositions are contemplated to optionally contain a therapeutically effective amount of a syndecan-2 modulator or antagonist. Therapeutically effective amounts or dosages are contemplated to include dosages of 0.01 mg to 20 mg, for example, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of 0.1 mg to 2.0 mg.

Syndecan-2 modulator and antagonist compositions are contemplated to optionally contain a therapeutically effective amount of a syndecan-2 modulator or antagonist. Therapeutically effective amounts or dosages are contemplated to include dosages of about 0.01 mg to about 20 mg, for example, about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of about 0.1 mg to about 2.0 mg. As used herein "about" is understood to include values plus or minus 10% of the indicated value.

Methods and Compositions in Treatment of Cancer

Modulators of syndecan-2, provided herein, are contemplated for therapy against cancer. Therefore, provided herein is a modulator of syndecan-2 for use in treatment of cancer. In examples, set out below in more detail, the modulator acts in treating cancer by decreasing inflammation and cancer cell migration.

Specifically, treatment is achieved in embodiments herein using modulator compounds or molecules or compositions that act by binding to syndecan-2, such as cell surface syndecan-2 and thereby inhibition of inflammation and cancer cell migration.

Contemplated herein, the effect of the modulator is to counter the activity of syndecan-2. Thus, there is provided, an antagonist of syndecan-2 for use in treatment of cancer by inhibiting inflammation and cancer cell migration. Antagonist activity is typically achieved via binding to cell surface syndecan-2

Modulators of syndecan-2, provided herein, are contemplated for treatment of cancer in general and multiple types of cancer. Cancers treatable by modulators of syndecan-2 include but are not limited to cancer comprises Acute lymphoblastic leukemia (ALL); Acute myeloid leukemia; Adrenocortical carcinoma; AIDS-related cancers; AIDS-related lymphoma; Anal cancer; Appendix cancer; Astrocytoma; childhood cerebellar or cerebral; Basal-cell carcinoma; Bile duct cancer; extrahepatic (see Cholangiocarcinoma); Bladder cancer; Bone tumor; Osteosarcoma/Malignant fibrous histiocytoma; Brainstem glioma; Brain cancer; Brain tumor; cerebellar astrocytoma; Brain tumor; cerebral astrocytoma/malignant glioma; Brain tumor; ependymoma; Brain tumor; medulloblastoma; Brain tumor; supratentorial primitive neuroectodermal tumors; Brain tumor; visual pathway and hypothalamic glioma; Breast cancer; Bronchial adenomas/carcinoids; Burkitt's lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer; Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liposarcoma; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Macroglobulinemia, Waldenstrom; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplasia Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma; Squamous neck cancer with occult primary, metastatic; Stomach cancer; Supratentorial primitive neuroectodermal tumor, childhood; T-Cell lymphoma, cutaneous; Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenstrom macroglobulinemia, and Wilms tumor (kidney cancer), childhood.

Some treatments provided herein relieve or reduce at least one symptom of cancer. Symptoms of cancer are variable depending on the type of cancer. Some such symptoms are known in the art and include but are not limited to fatigue, weight loss, fever, pain, constipation, diarrhea, unusual bleeding, and other signs and symptoms of cancer, including early death.

The methods of treatment described herein treat various stages of cancer including stages which are locally advanced, metastatic and/or recurrent. In cancer staging, locally advanced is generally defined as cancer that has spread from a localized area to nearby tissues and/or lymph nodes. In the Roman numeral staging system, locally advanced usually is classified in Stage II or III. Cancer which is metastatic is a stage where the cancer spreads throughout the body to distant tissues and organs (stage IV). Cancer designated as recurrent generally is defined as the cancer has recurred, usually after a period of time, after being in remission or after a tumor has visibly been eliminated. Recurrence is either be local, i.e., appearing in the same location as the original, or distant, i.e., appearing in a different part of the body. In certain instances, a cancer treatable by combination therapies described herein is unresectable, or unable to be removed by surgery.

In some of such embodiments, the methods of treatment described herein provide adjunct therapy to any other cancer therapy prescribed for an individual. Accordingly, in some embodiments, decoy polypeptides described herein are administered in combination with treatment with any other anti-cancer agent including and not limited to methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl) amine, troxacitabine, uracil mustard, valrubicin, vinblastine, vincristine, vinorelbine, vorinostat, zosuquidar, or the like.

In additional embodiments, the methods of treatment described herein i.e., modulators of syndecan-2 described herein are administered in combination with anti-diarrheal agents, anti-emetic agents, analgesics, opioids and/or non-steroidal anti-inflammatory agents.

The modulators and antagonists disclosed herein are optionally also be used in combination with cell therapies for various diseases. Accordingly further provided is a composition comprising a modulator of or antagonist of syndecan-2 combined for use according to earlier aspects herein in treatment of cancer, in combination with a population of mammalian cells at least 30% of which are positive for syndecan-2. Also provided herein, is a composition comprising a modulator of or antagonist of syndecan-2 combined with a population of CAR T cells. Further contemplated herein, is a composition comprising a modulator of or antagonist of syndecan-2 combined with a population of isolated tumor infiltrating lymphocytes. Alternatively, provided herein is a composition comprising a modulator of or antagonist of syndecan-2 combined with a population of CCR7+, CD62L+ central memory T cells. In addition, there is provided a composition comprising a modulator of or antagonist of syndecan-2 combined with a population of natural killer cells. In some cases the cells are administered as a single composition in combination with a modulator or antagonist disclosed herein. Alternately or in combination, in some cases the cells are administered separately or through a separate route of administration relative to a modulator or antagonist disclosed herein.

The cells used in the therapy are generally mouse, rat, equine or human cells, preferably human cells. In embodiments of such therapies, 40% or more or 50% or more or 75% or more of the mammalian cell population are positive for syndecan-2. Further elements of suitable cell therapies, for use in combination with the modulator/antagonist therapies herein are described in WO2013/117761, which is hereby incorporated by reference in its entirety.

In some of the above embodiments, treatment with a decoy polypeptide described herein (e.g., a composition comprising a modulator of syndecan-2) prolongs lifespan and/or increases survival rates for individuals suffering from cancer. In some of the above embodiments, treatment with a modulator of syndecan-2 described herein (e.g., a composition comprising an anti-syndecan-2 antibody or syndecan-2 fragment polypeptide) improves quality of life for an individual suffering from cancer (e.g., an individual needs a lower dose of an anti-cancer drug that causes side-effects when the individual is treated with a decoy polypeptide described herein).

The disclosure further provides for therapy of diseases known to be caused by or to have a related increase in Th17 activity, though being neither autoimmune disease nor fibrosis diseases. Accordingly, the invention provides a modulator or antagonist as described elsewhere herein for use in treatment of a disease selected from Barrett's esophagus, depression, fibromyalgia (FM), gastroesophageal reflux disease (GERD), hypertension, hyperthyroidism, hypothyroidism, irritable bowel syndrome (IBS), interstitial cystitis (IC), kidney stones, multiple chemical sensitivity (MCS), migraine headache, Morgellon's, Raynaud's syndrome/phenomenon, restless leg syndrome, reflex sympathetic dystrophy (RSD), sinusitis, seasonal affective disorder (SAD), ulcerative colitis, uveitis, vertigo, chronic fatigue syndrome (CFS/CFIDS/ME), chronic Lyme disease (borreliosis), Löfgren's syndrome and prostatitis.

Methods and compositions of the invention treat autoimmune disease with a modulator that targets syndecan-2 because syndecan-2 has a controlling effect on Th17 cells, as newly demonstrated by the data in examples herein. The treatment is consistent with the art teaching that Th17 cells are involved in the autoimmune aspect of disease. Clinical trials with anti-IL-17 antibodies as a treatment for human inflammatory diseases including rheumatoid arthritis, uveitis and psoriasis have shown success. Also the functional link of Th17 cells with asthma and COPD and some cancers, especially colon cancer is known.

Targeting Th17 cells has been proposed to treat autoimmune conditions including rheumatoid arthritis, systemic lupus erythematosus, multiple sclerosis, psoriasis, inflammatory bowel disease (Crohn's disease and ulcerative colitis), allergy and asthma. The compositions and methods herein demonstrate targeting and inhibition of Th17 cells.

Th17 cells are involved in fibrotic diseases. Therefore it is reasonable to treat these diseases with an antagonist that targets syndecan-2 because syndecan-2 has a controlling effect on Th17. It is known for example that Th17 cytokines induce pro-fibrotic cytokine release from human eosinophils. Preventing the release of pro-fibrotic cytokines by blocking the effect of Th17 cytokines is now possible with the compositions and methods herein due to the targeted anti-Th17 activities of compounds and compositions of the invention.

Methods of treatment of cancer or cell cycle, cell growth, or cell apoptosis related diseases or disorders comprise administration of a composition herein to a patient in need of alleviation of symptoms. Often, a subject is identified as presenting symptoms of cancer or a cell cycle, cell growth, or cell apoptosis related diseases or disorders and is selected to receive the treatment comprising a composition as disclosed herein. A composition recited herein is administered to the subject. Administration is intravenous, in many preferred embodiments, but alternate routes of administration such as surface administration, or otherwise directly contacting the target tissue are also contemplated. Compositions are administered locally or systemically, as a salve, lotion or emulsion, are injected, are surgically introduced, are ingested, are administered topically, orally, bucaly, nasally, or are introduced into a cavity of the subject. Compositions are administered singly, or over a time course, such as daily, multiple times weekly, weekly, biweekly, monthly or less frequently. Compositions are administered alone or in concert with additional measures that are in some cases related to treatment of the disorder, such as dietary supplement or adjustment, exercise or other treatment. Administration occurs during or between meals, and is independent of or alternately dependent upon daily administration timing, such as morning administration, evening administration, or multiple administrations relative to sleep, meals or exercise.

In some cases a subject in need of treatment is monitored prior to administration of a composition as presented herein. Symptoms are identified and their severity is assessed. The composition as described herein is administered alone or in combination with additional measures, singly or multiply over time ad discussed herein or known to one of skill in the art. The subject is optionally monitored such that the efficacy of the treatment regimen is determined. Optionally, a treatment regimen is modified in response to preliminary treatment outcomes, such that treatment dose or frequency or does and frequency is altered so as to attain a desired level of subject response in light of symptom alleviation, side effect reduction, or a combination of symptom alleviation and side effect reduction. In some cases a report is produced prior to, during, following or prior to, during and following a treatment regimen, and is provided to a doctor, health care practitioner, insurer and/or subject or subject's representative.

Syndecan-2 modulator and antagonist compositions are contemplated to optionally contain a therapeutically effective amount of a syndecan-2 modulator or antagonist. Therapeutically effective amounts or dosages are contemplated to include dosages of 0.01 mg to 20 mg, for example, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of 0.1 mg to 2.0 mg.

Syndecan-2 modulator and antagonist compositions are contemplated to optionally contain a therapeutically effective amount of a syndecan-2 modulator or antagonist. Therapeutically effective amounts or dosages are contemplated to include dosages of about 0.01 mg to about 20 mg, for example, about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 10.1 mg, 10.2 mg, 10.3 mg, 10.4 mg, 10.5 mg, 10.6 mg, 10.7 mg, 10.8 mg, 10.9 mg, 11 mg, 11.1 mg, 11.2 mg, 11.3 mg, 11.4 mg, 11.5 mg, 11.6 mg, 11.7 mg, 11.8 mg, 11.9 mg, 12 mg, 12.1 mg, 12.2 mg, 12.3 mg, 12.4 mg, 12.5 mg, 12.6 mg, 12.7 mg, 12.8 mg, 12.9 mg, 13 mg, 13.1 mg, 13.2 mg, 13.3 mg, 13.4 mg, 13.5 mg, 13.6 mg, 13.7 mg, 13.8 mg, 13.9 mg, 14 mg, 14.1 mg, 14.2 mg, 14.3 mg, 14.4 mg, 14.5 mg, 14.6 mg, 14.7 mg, 14.8 mg, 14.9 mg, 15 mg, 15.1 mg, 15.2 mg, 15.3 mg, 15.4 mg, 15.5 mg, 15.6 mg, 15.7 mg, 15.8 mg, 15.9 mg, 16 mg, 16.1 mg, 16.2 mg, 16.3 mg, 16.4 mg, 16.5 mg, 16.6 mg, 16.7 mg, 16.8 mg, 16.9 mg, 17 mg, 17.1 mg, 17.2 mg, 17.3 mg, 17.4 mg, 17.5 mg, 17.6 mg, 17.7 mg, 17.8 mg, 17.9 mg, 18 mg, 18.1 mg, 18.2 mg, 18.3 mg, 18.4 mg, 18.5 mg, 18.6 mg, 18.7 mg, 18.8 mg, 18.9 mg, 19 mg, 19.1 mg, 19.2 mg, 19.3 mg, 19.4 mg, 19.5 mg, 19.6 mg, 19.7 mg, 19.8 mg, 19.9 mg, or 20 mg. Therapeutically effective amounts or dosages, in some cases, are contemplated to include dosages of about 0.1 mg to about 2.0 mg. As used herein "about" is understood to include values plus or minus 10% of the indicated value.

Turning to the figures, one sees the following. FIG. 1 illustrates: Schematic of proliferation seen across Donor 1 cultures of Th1, Th17 and Treg cells with proliferation represented as the percentage of cells that divided more than 3 times (left). Histogram of significant difference, as indicated in left panel, in CFSE levels represented on the FITC fluorochrome in Th17 cultures stimulated by isotype control and α-syndecan-2 antibody with greater levels indicating less proliferation (*p<0.05, p<0.01, *p<0.001, ****p<0.0001).

FIG. 1 compares proliferation of Th1, Th17 and Treg cells when anti-CD3 stimulated them in the presence of either the isotype control antibody or the α-syndecan-2 antibody. Treatment of cells with the α-syndecan-2 antibody resulted in a significant decrease in the proliferation of Th17 cells. This significant difference is represented by CFSE dilution on the FITC fluorochrome in the histograms shown (right).

Figure 2:
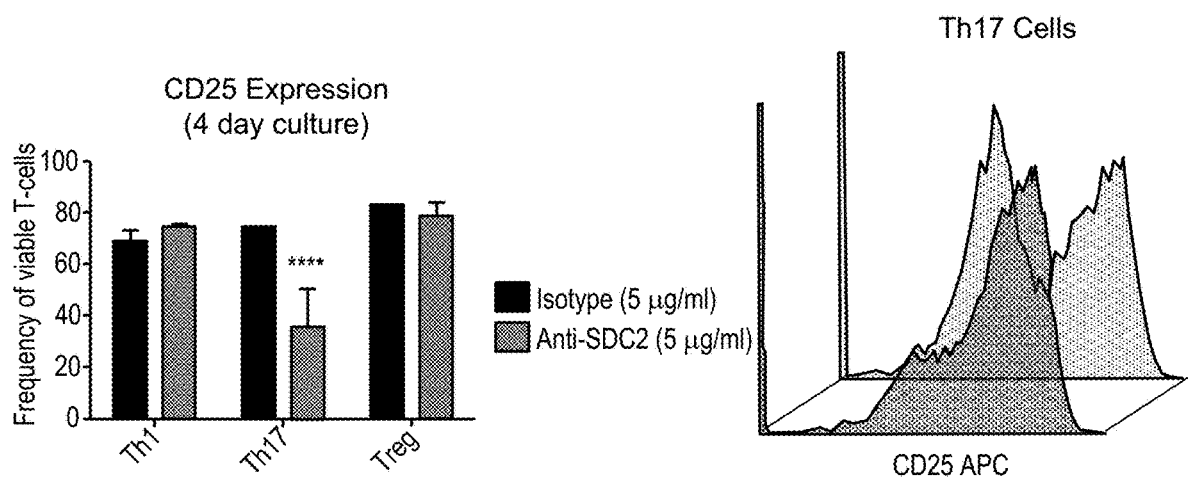
FIG. 2 illustrates a schematic of maturation marker, CD25 expression, seen across cultures of Th1, Th17 and Treg cells represented as frequency of viable T-cells.
Figure 2:
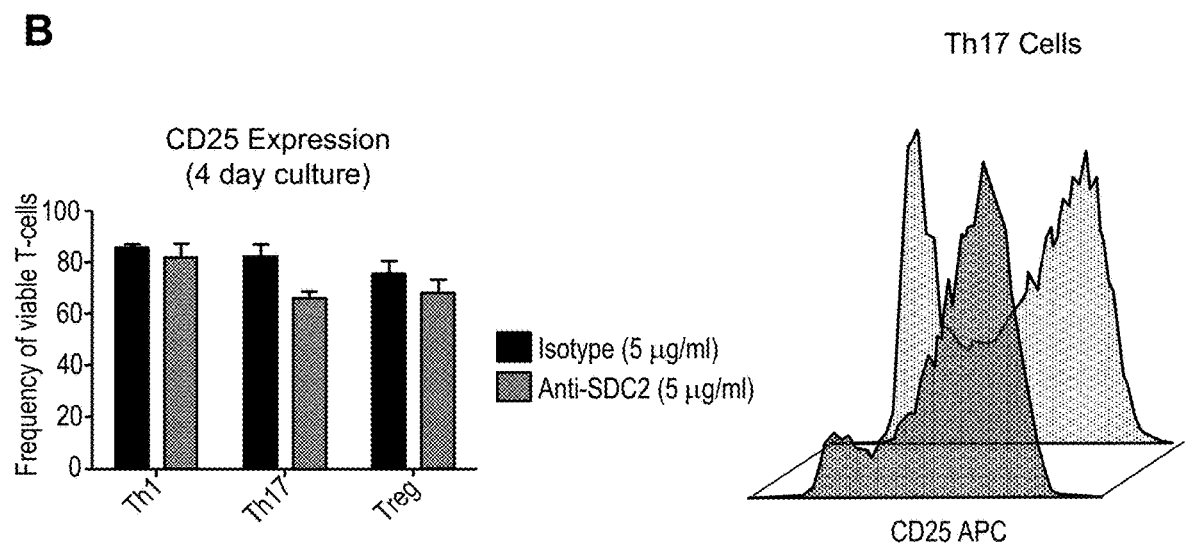

FIG. 2 illustrates A) Schematic of maturation marker, CD25 expression, seen across Donor 1 cultures of Th1, Th17 and Treg cells represented as frequency of viable T-cells (left). Histogram of significant difference, as indicated in left panel, in CD25 in Th17 cultures stimulated by isotype control and α-syndecan-2 antibody. B) Data generated from Donor 2 cells (*p<0.05,  p<0.01, * p<0.001, ****p<0.0001).

FIG. 2 compares expression of a maturation marker, CD25, on Th1, Th17 and Treg cells when anti-CD3 stimulated them in the presence of either the isotype control antibody or the α-syndecan-2 antibody. In each donor, it can be seen that treatment with the α-syndecan-2 antibody resulted in a significant decrease in the expression of CD25 on Th17 cells. However, the most significant result is seen in the case of Donor 1. This significant difference is represented on the APC fluorochrome in the histograms shown (right).

Figure 3:
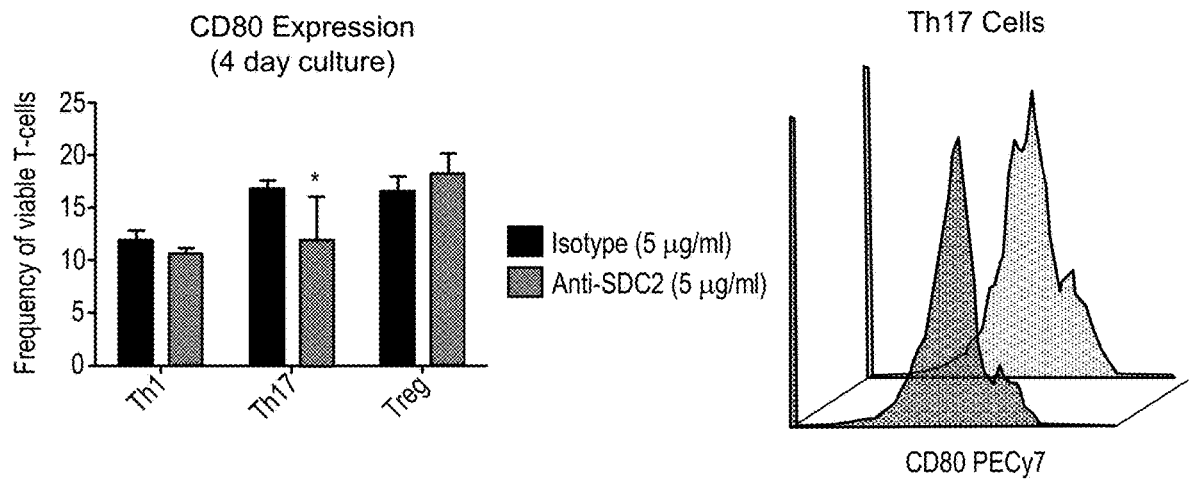
FIG. 3 illustrates a schematic of maturation marker, CD80 expression, seen across cultures of Th1, Th17 and Treg cells represented as frequency of viable T-cells.
Figure 3:
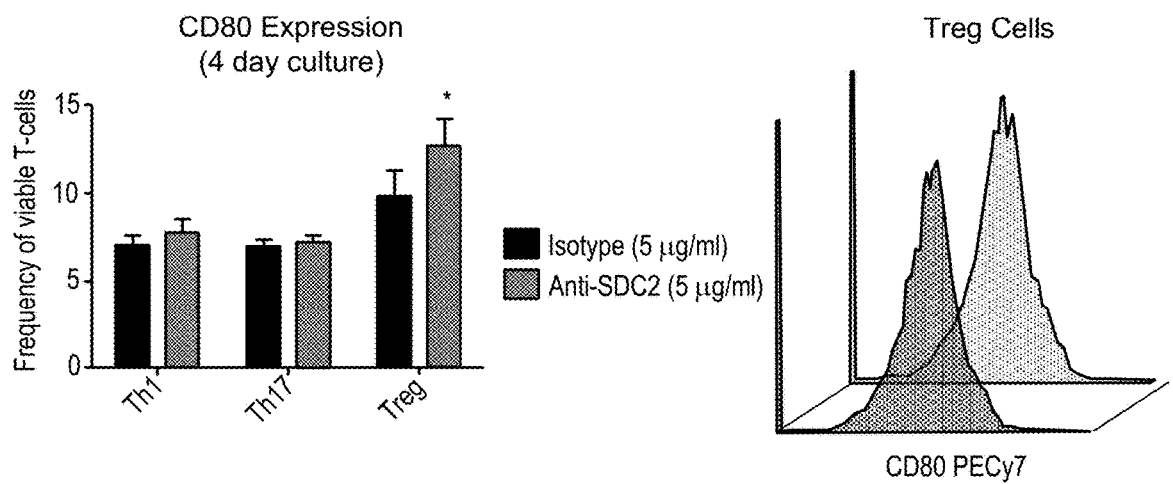

FIG. 3 illustrates: A) Schematic of maturation marker, CD80 expression, seen across Donor 1 cultures of Th1, Th17 and Treg cells represented as frequency of viable T-cells (left). Histogram of significant difference, as indicated in left panel, in CD80 represented on the PECy7 fluorochrome in Th17 cultures stimulated by isotype control and α-syndecan-2 antibody. B) Data generated from Donor 2 cells (*p<0.05,  p<0.01, * p<0.001, ****p<0.0001).

FIG. 3 compares expression of a maturation marker, CD80, on Th1, Th17 and Treg cells when stimulated by either the isotype control antibody or the α-syndecan-2 antibody with the data presented as the frequency of viable T cells. In Donor 1, it can be seen that treatment with the α-syndecan-2 antibody resulted in a significant decrease in the expression of CD80 on Th17 cells. This significant difference is represented on the PECy7 fluorochrome for Th17 cells.

Figure 4:
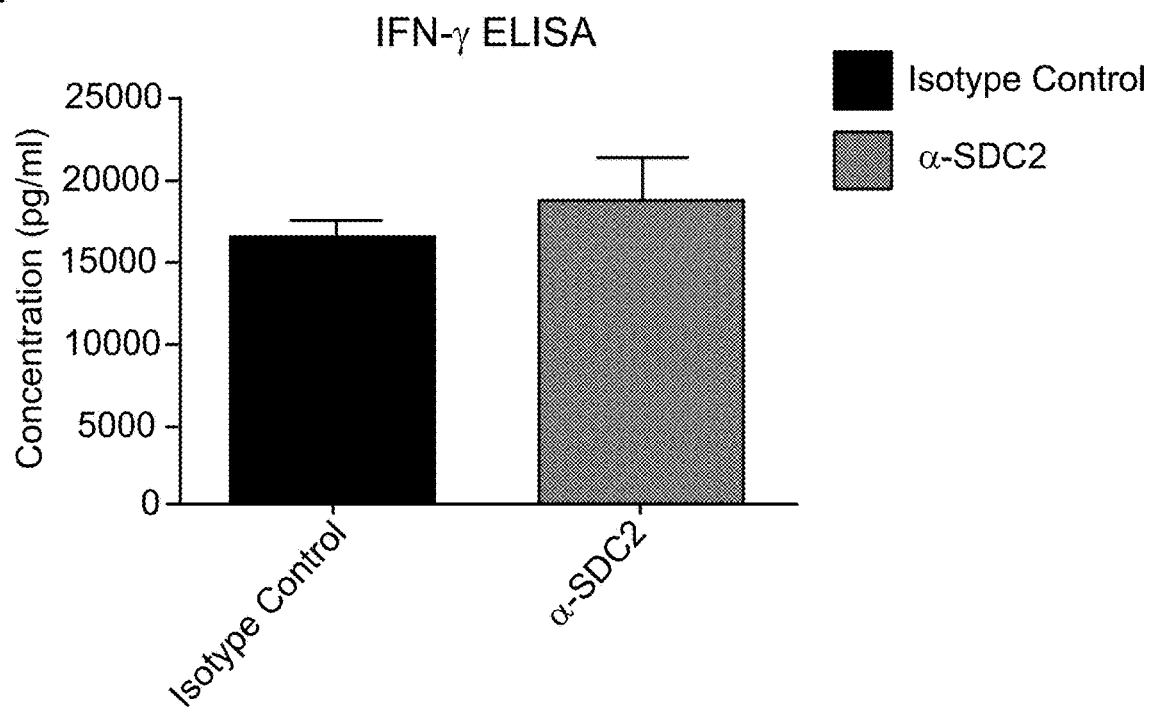
FIG. 4 illustrates a schematic of concentrations of IFN-γ in supernatants removed following 4 day incubation of Th1 cultures following treatment with isotype control or α-syndecan-2 antibody.
Figure 4:
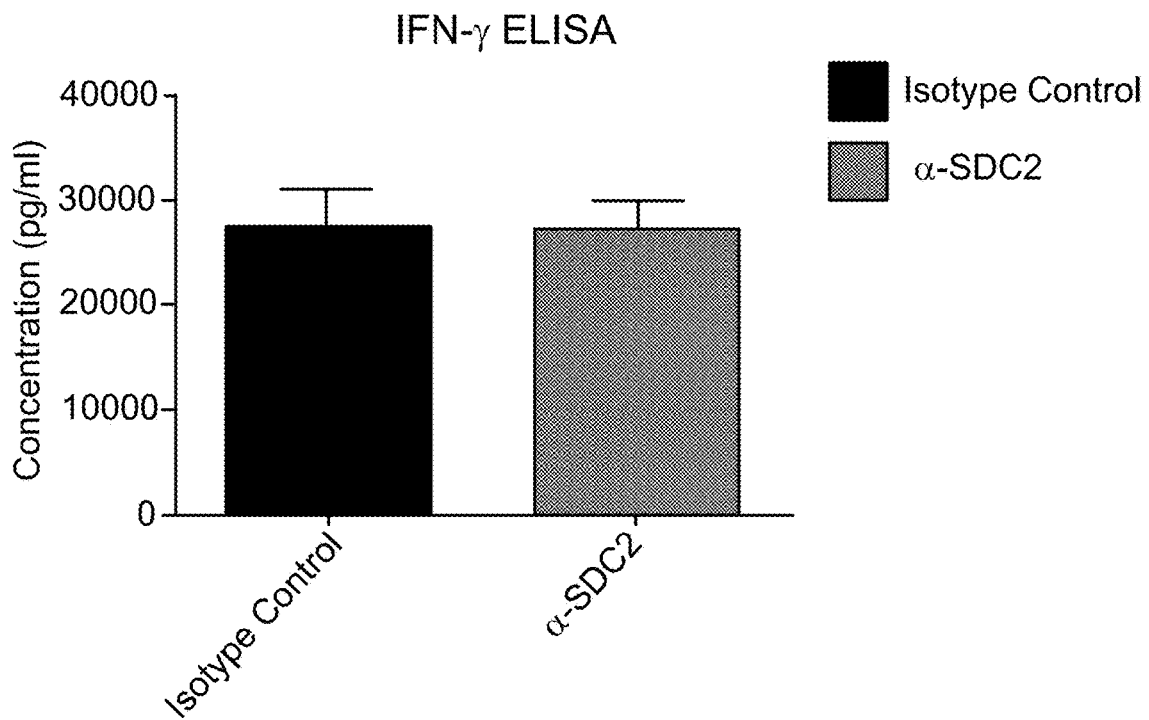

FIG. 4 illustrates: A) Schematic of concentrations of IFN-γ in supernatants removed following 4 day incubation of Donor 1 Th1 cultures following treatment with isotype control or α-syndecan-2 antibody, B) Schematic of concentrations of IFN-γ in supernatants removed following 4 day incubation of Donor 2 Th1 cultures following treatment with isotype control or α-syndecan-2 antibody, FIG. 4 compares IFN-γ concentrations in Th1 cultures following treatment with either the control isotype antibody or α-syndecan-2 antibody. There was no significant change observed in the concentration of IFN-γ following α-syndecan-2 antibody treatment in either donor.

Figure 5:
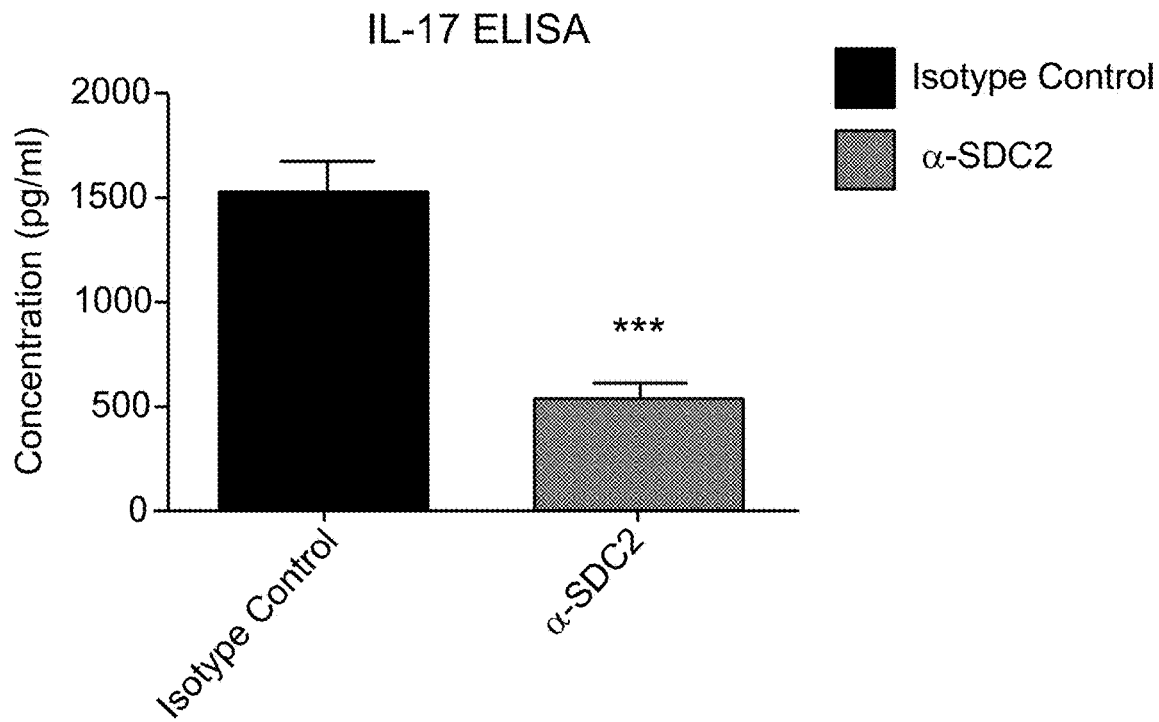
FIG. 5 illustrates a schematic of concentrations of IL-17 in supernatants removed following 4 day incubation of Th17 cultures following treatment with isotype control or α-syndecan-2 antibody.
Figure 5:
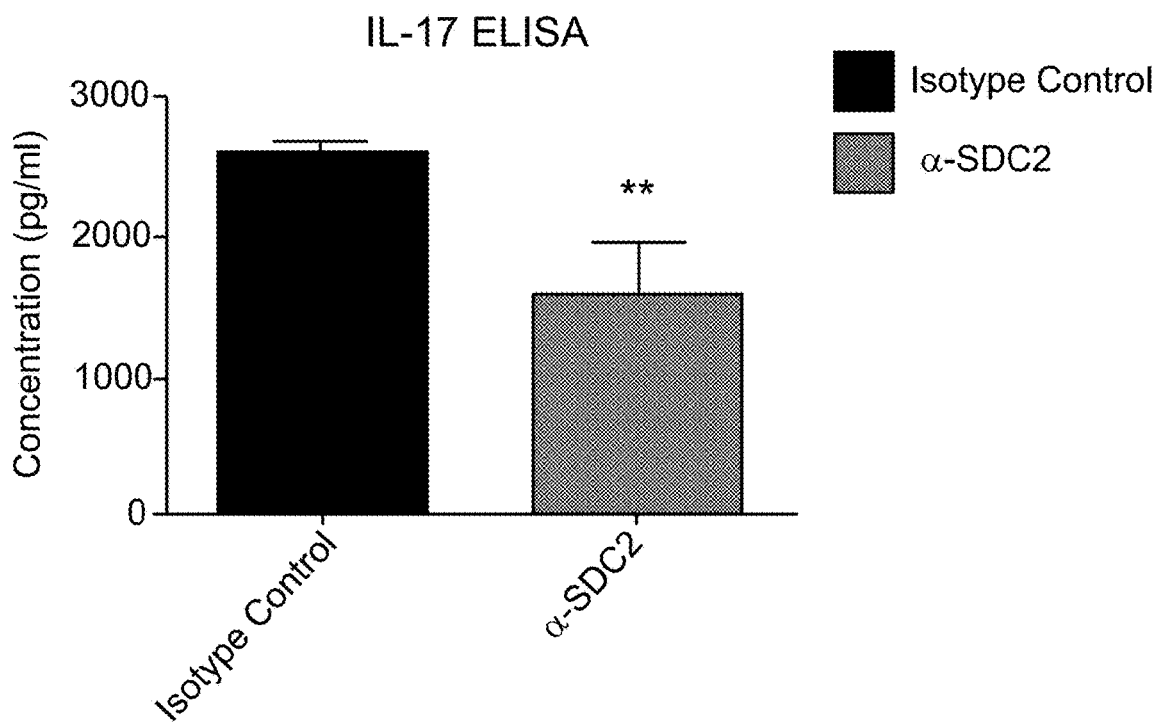

FIG. 5 illustrates: A) Schematic of concentrations of IL-17 in supernatants removed following 4 day incubation of Donor 1 Th17 cultures following treatment with isotype control or α-syndecan-2 antibody, B) Data generated from Donor 2 cells.

FIG. 5 compares IL-17 concentrations in Th17 cultures following treatment with either the control isotype antibody or α-syndecan-2 antibody. It can be observed that following α-syndecan-2 antibody treatment, IL-17 concentrations are significantly decreased in both donors. However, the most significant result is observed in the case of Donor 1.

Figure 6:
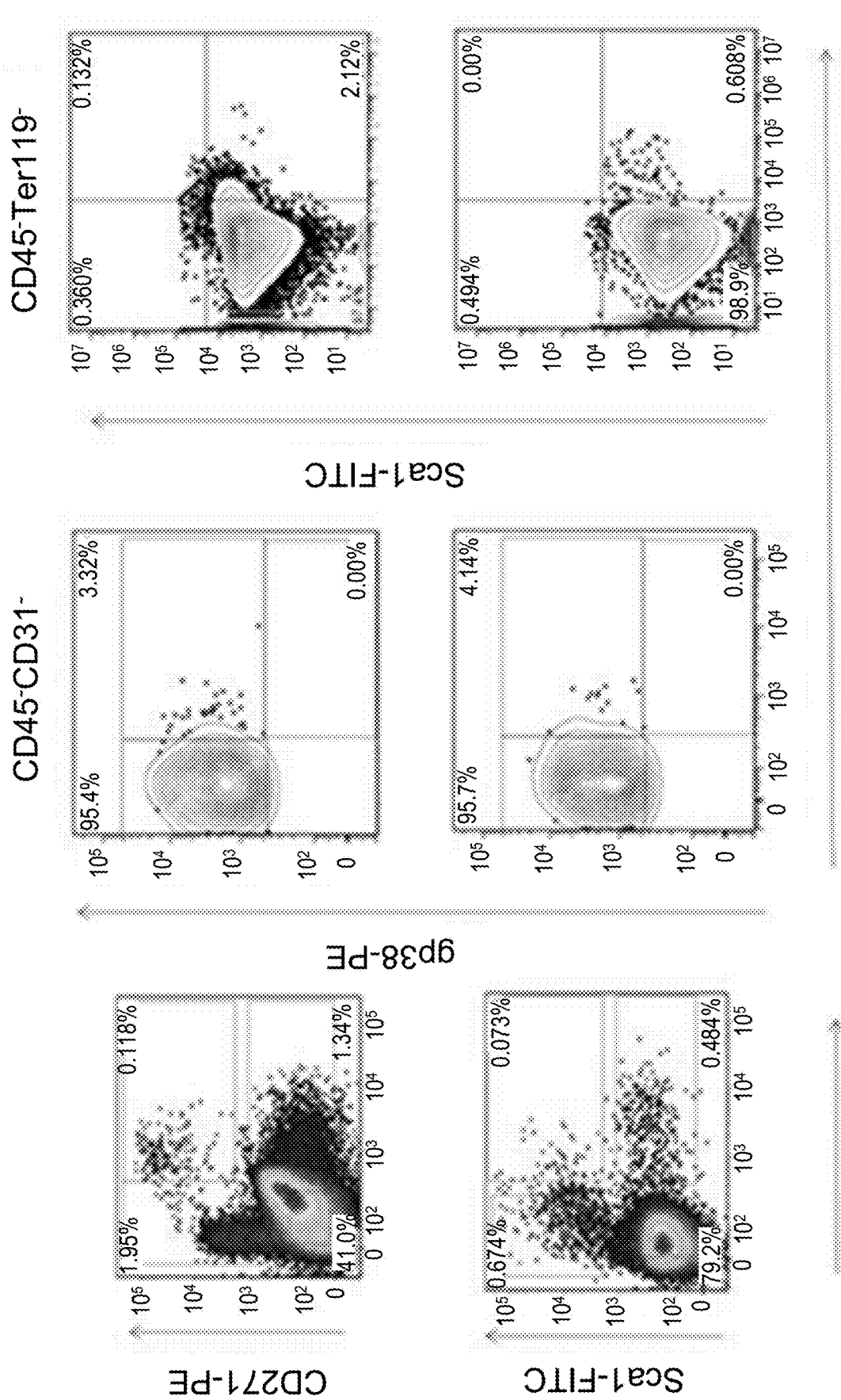
FIG. 6 illustrates SDC2 as a novel marker for identification of stromal cells (SC) from murine and human tissue.

SDC2 is a novel marker for identification of stromal cells (SC) from murine and human tissue. Flow cytometry analysis, shown in FIG. 6, at left, of Sdc2$^+$CD271$^+$CD45– and Sdc2$^+$Sca1$^+$CD45$^-$ mononuclear cells from human and mouse bone marrow respectively. Identification of Sdc2$^+$gp38$^+$CD45$^-$ stromal cells (FIG. 6, center) in mouse lymph nodes and thymus by flow cytometry analysis. Finally identification of Sdc2$^+$Sca1$^+$CD45$^-$ stromal cells (FIG. 6, at right) in mouse adipose and muscle tissue by flow cytometry analysis. This illustrates that Sdc2 is a novel marker that can be used to isolate stromal cells from normal and tumor tissue.

Figure 7A:
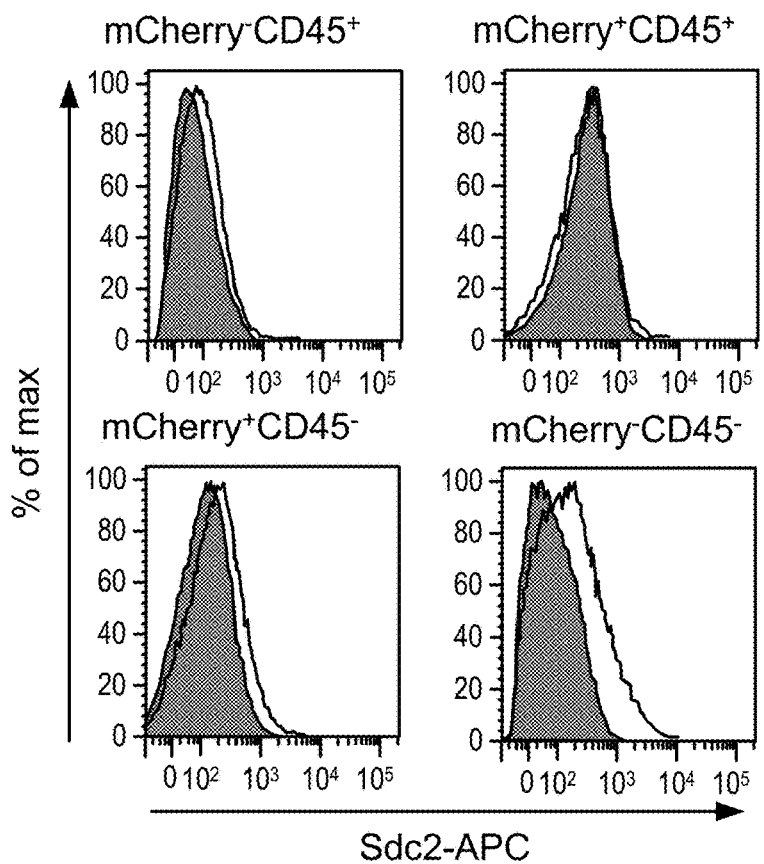
FIGS. 7A-C illustrate Sdc2 is present in the stroma, epithelium and serum of breast cancers.
Figure 7B:
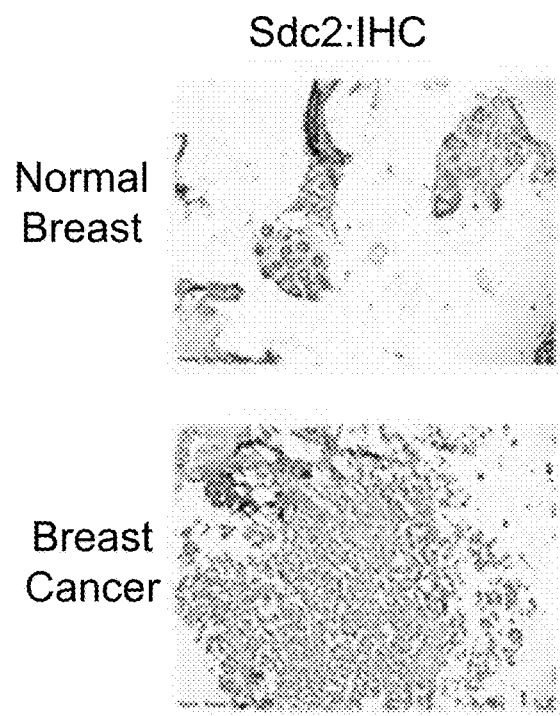
Figure 7C:
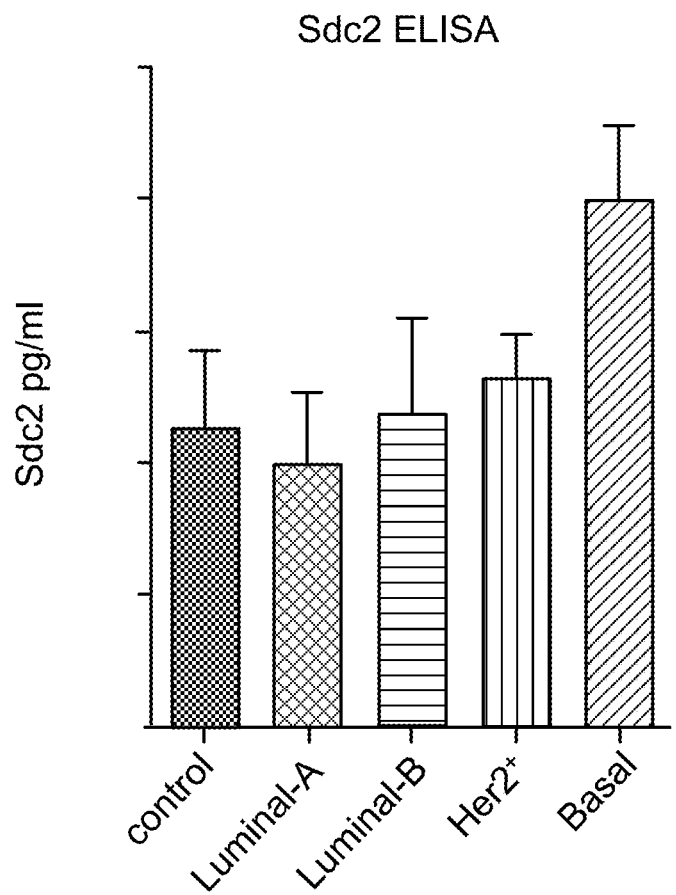

Sdc2 is present in the stroma, epithelium and serum of breast cancers. This was shown by flow cytometry of dissected breast tumours (FIG. 7A) from PyMT-ChOVA mice revealing Sdc2$^+$epithelial (mCherry$^+$ve, CD45-ve), and Sdc2$^+$SC (mCherry-ve, CD45-ve, GP38$^+$ve). Immunohistochemistry (FIG. 7B) revealed increased levels of Sdc2 protein in human breast tumours. ELISA demonstrated high levels of Sdc2 protein in serum of patients with basal-like breast cancer (FIG. 7C).

Figure 8A:
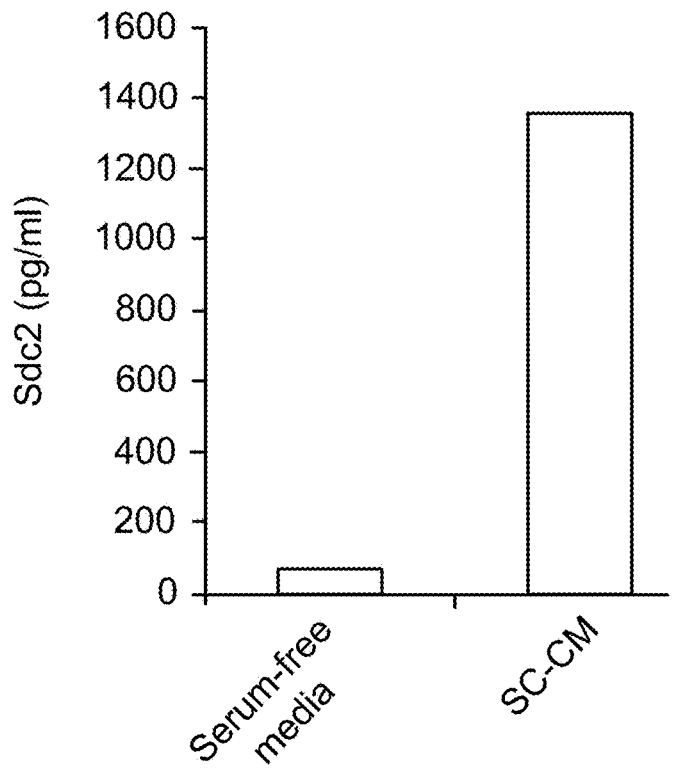
FIGS. 8A-D illustrate that Sdc2 enhances breast cancer cell migration and inhibits T-cell proliferation.
Figure 8B:
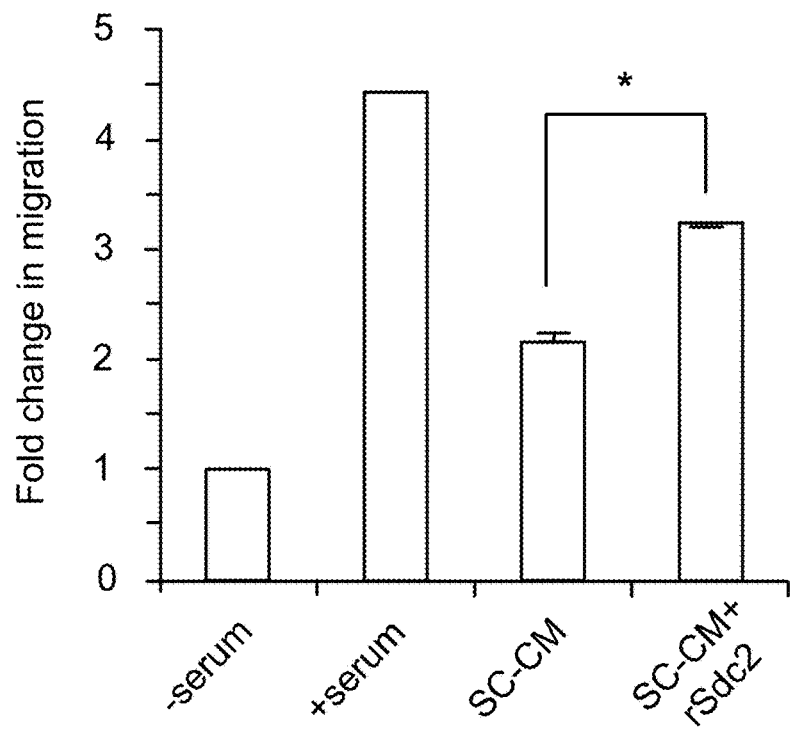
Figure 8C:
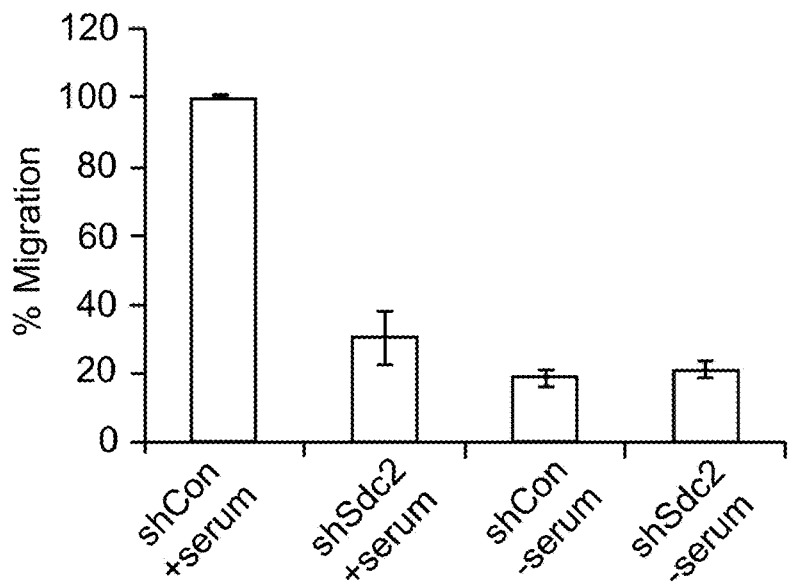
Figure 8D:
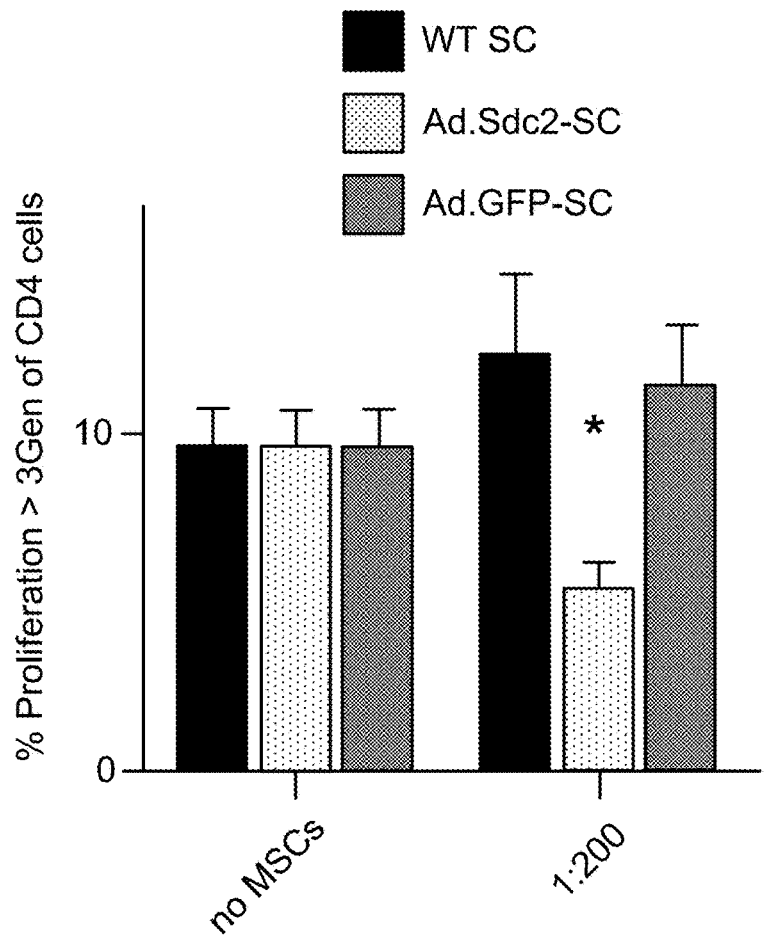

Sdc2 enhances breast cancer cell migration and inhibits T-cell proliferation. ELISA demonstrated high levels of Sdc2 in stromal cell-conditioned media (SC-CM) (FIG. 8A). SC-CM enhanced the migration of MDA-MB-231 breast cancer cells (BCC), and pre-incubation of BCC with recombinant Sdc2 enhances migration towards SC-CM (FIG. 8B). Inhibition of Sdc2 activity, in this case by knockdown of Sdc2 inhibited the ability of BCC to migrate towards serum containing media (FIG. 8C). Flow cytometry of CFSE-labeled CD4$^+$ T cells, revealed CD3/CD28-mediated stimulation of proliferation is inhibited by SC overexpressing Sdc2 (FIG. 8D). Thus, inhibition of Sdc2, for example using a Syndecan-2 extracellular domain or a polypeptide having a Syndecan-2 binding domain, is a method of inhibiting BCC migration and therefore of treating cancer.

Figure 9A:
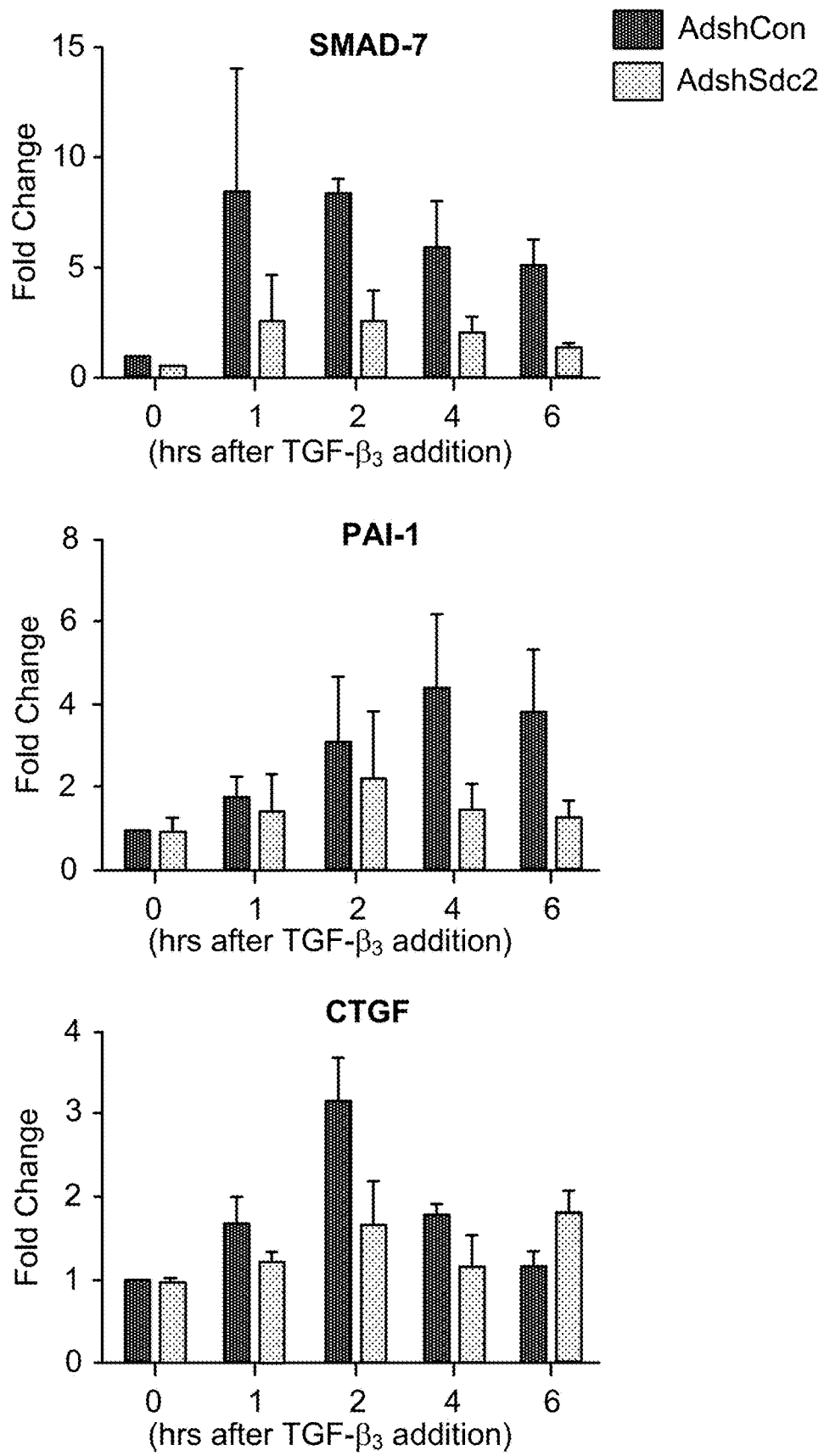
FIGS. 9A-B illustrates that Sdc2 is required for TGF-β-induced epithelial to mesenchymal transition (EMT).
Figure 9B:
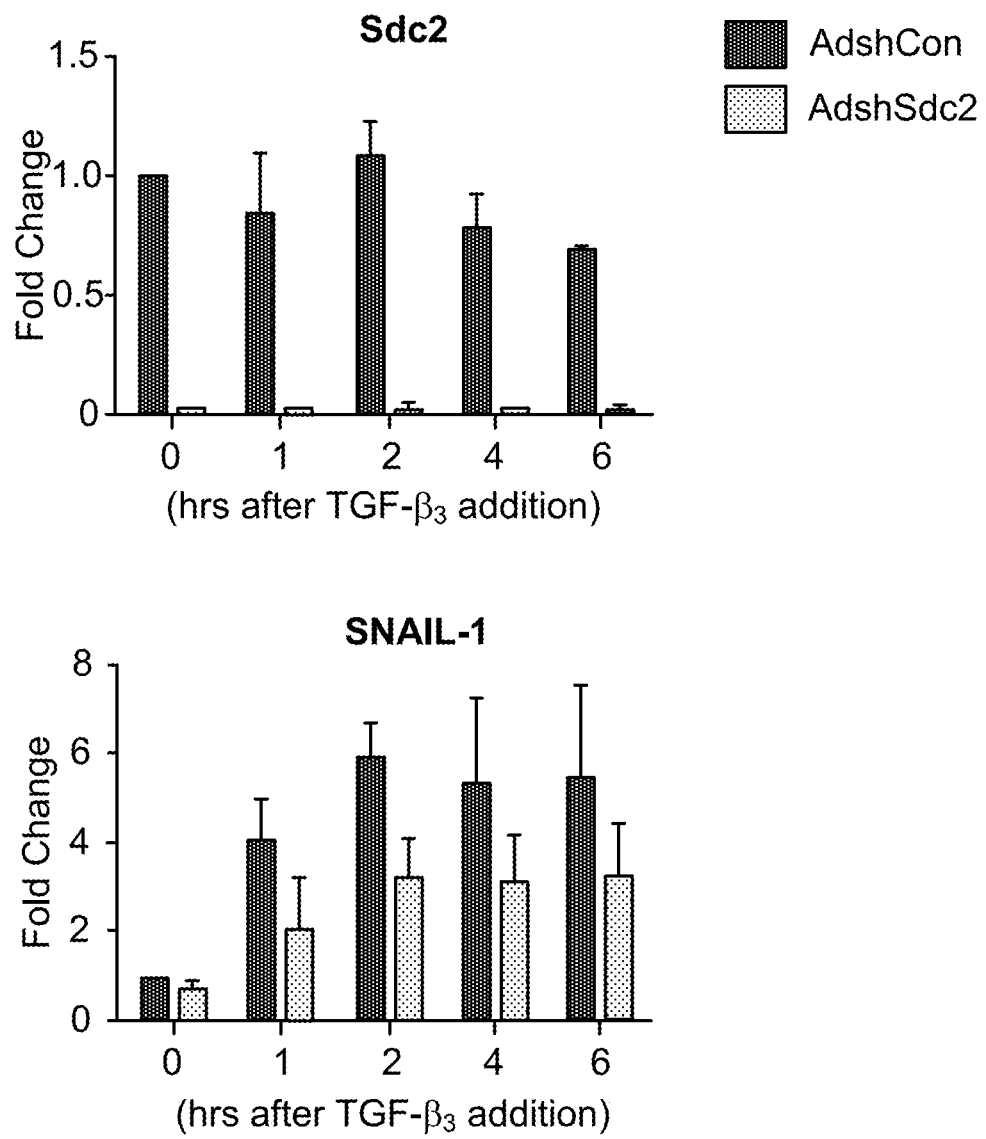
Figure 9B:
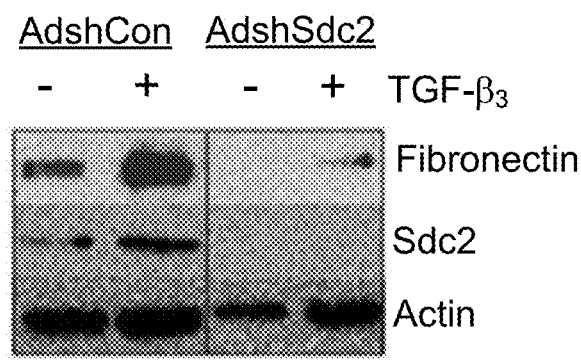

Sdc2 is required for TGF-β-induced epithelial to mesenchymal transition (EMT). MDA-MB-231 cells transduced with AdshSdc2 showed an attenuated TGFβ-induced increase in SMAD7, PAI-1 and CTFG RNA when compared to control cells expressing empty vector (EV). RT-qPCR demonstrated efficient knockdown of Sdc2 (FIG. 9A). RT-qPCR and Western blot analysis demonstrated that Sdc2 knockdown attenuates TGFβ-mediated induction of EMT markers, SNAIL-1 and Fibronectin respectively (FIG. 9B).

Figure 10A:
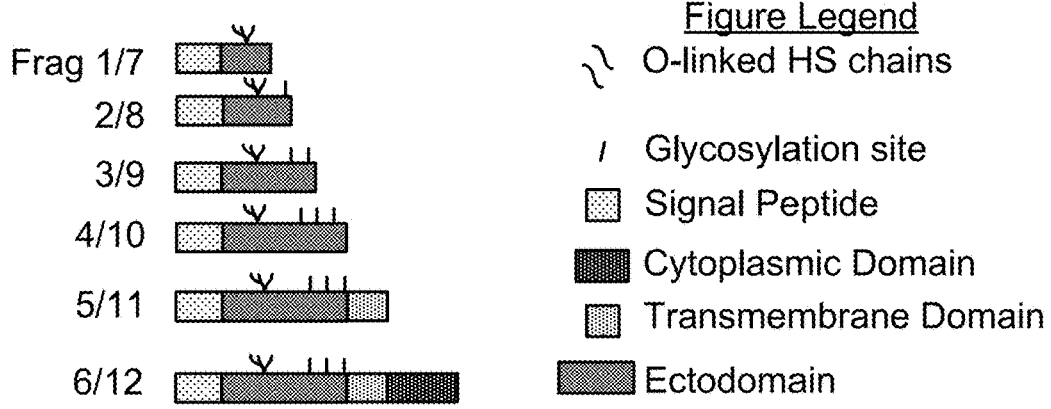
FIG. 10A-D illustrate that Sdc2 peptides have anti migratory and anti-inflammatory properties in vitro.
Figure 10B:
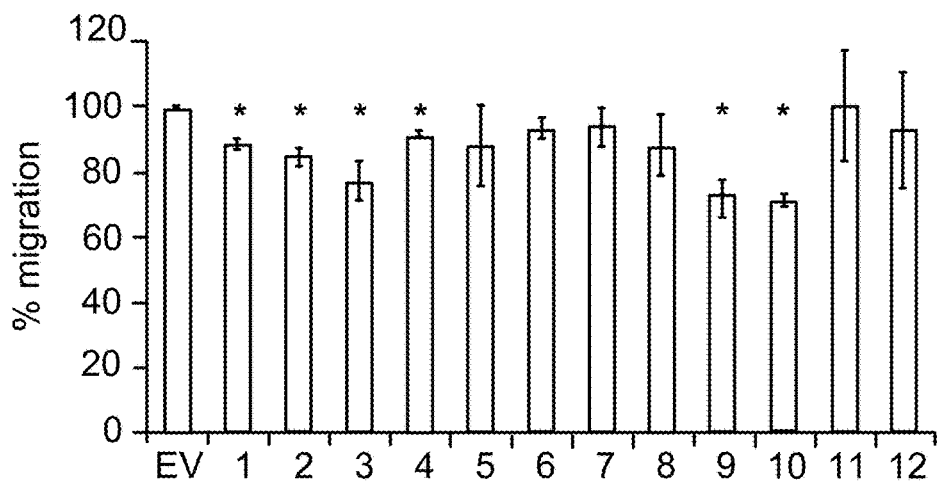
Figure 10C:
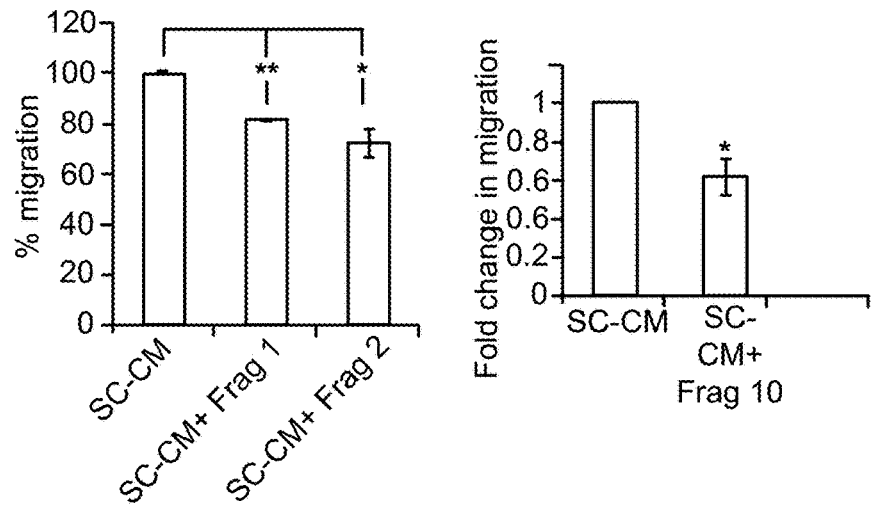
Figure 10D:
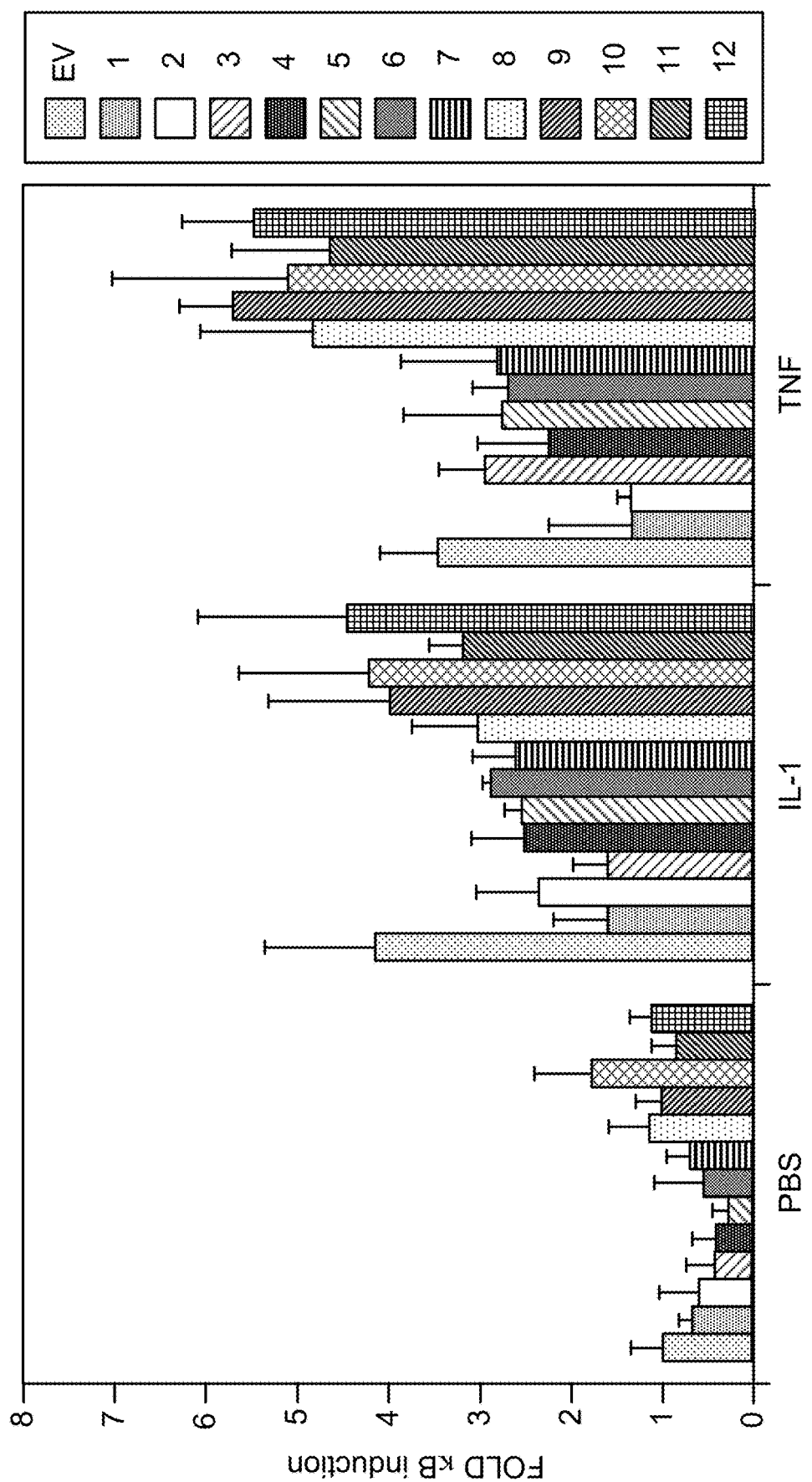

Sdc2 peptides have anti migratory and anti-inflammatory properties in vitro. Generation of deletion mutants containing different functional domains of Sdc2. Fragments 1-6 contain the signal peptide, whereas fragments 7-8 do not (FIG. 10A). Various Sdc2 functional fragments inhibited migration of MDA-MB-231 towards SC-CM in cis (FIG. 10B). Various Sdc2 functional fragments inhibited migration of MDA-MB-231 towards SC-CM in trans (FIG. 10C). (2-sided Students t-test *p<0.05) Various Sdc2 fragments significantly inhibited TNF-α/IL-1β-induced NF-κB activation (FIG. 10D).

Figure 11:
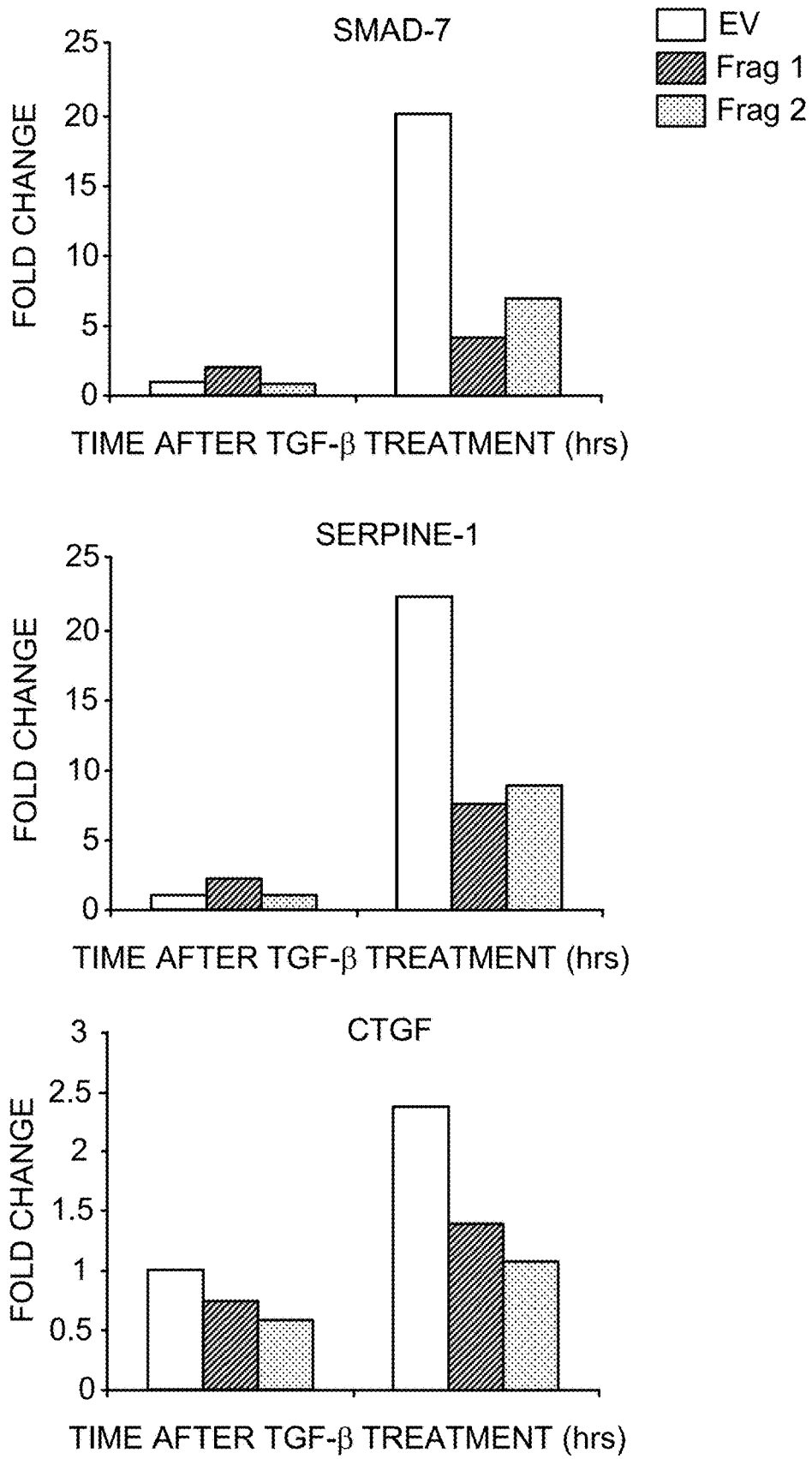
FIG. 11 illustrates Sdc2 peptides attenuate upregulation of TGF-β regulated genes. RT-qPCR analysis demonstrates that Sdc2-Fragment 1 and Sdc2-Fragment2 cause a reduction in TGFβ-mediated SMAD7, Serpine-1 and CTGF induction.

Sdc2 peptides attenuated upregulation of TGF-β regulated genes. RT-qPCR analysis demonstrated that Sdc2-Fragment 1 and Sdc2-Fragment2 caused a reduction in TGFβ-mediated SMAD7, Serpine-1 and CTGF induction (FIG. 11).

Figure 12:
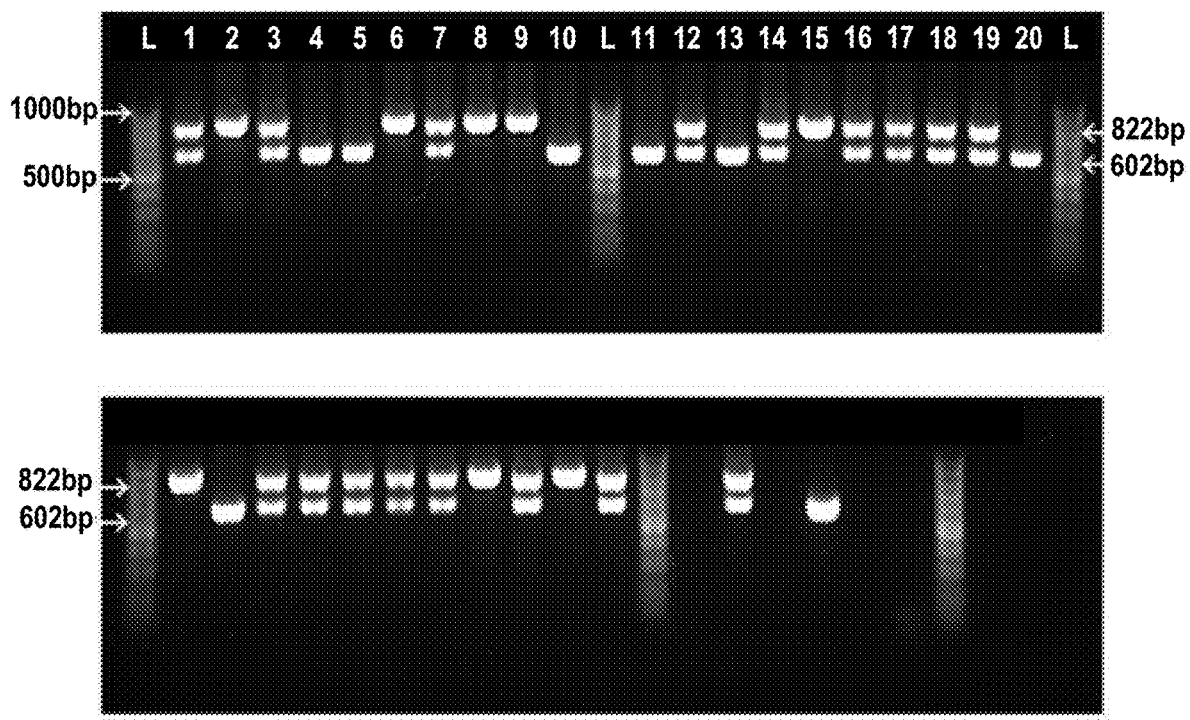
FIG. 12 illustrates genotyping results of DNA from ear punches of Sdc2$^{fl/fl}$ mice.

Sdc2 fl/fl mice were made using standard techniques known to one of skill in the art. Genotyping results of DNA from ear punches of Sdc2 fl/fl mice are shown in FIG. 12.

Figure 13:
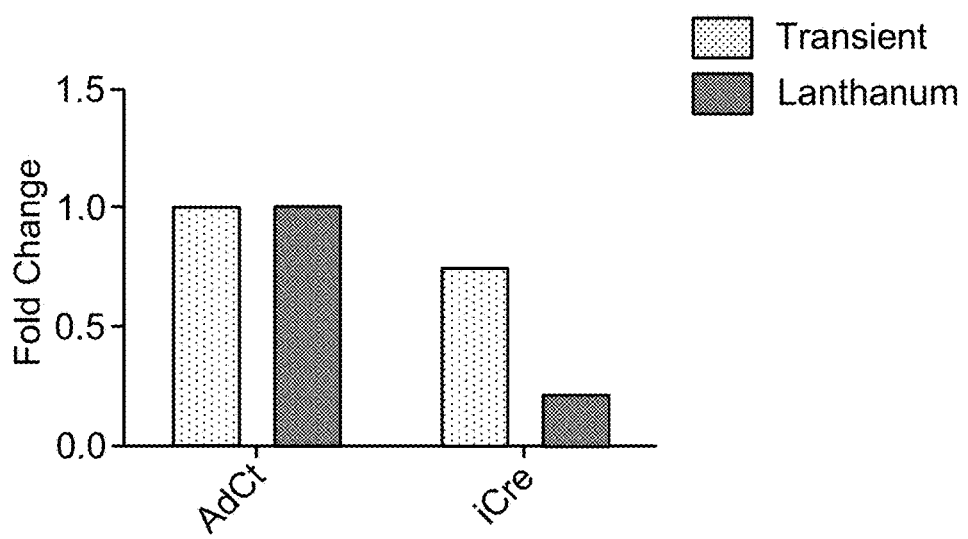
FIG. 13 illustrates Syndecan-2 knockdown in MSCs isolated from the Sdc2$^{fl/fl}$ mouse.

Mesenchymal Stem Cells (MSCs) were isolated from Sdc2fl/fl mice and treated with an adenovirus overexpressing cre recombinase. In some of the treated cells, lanthanum was added to the transfection. Syndecan-2 expression was measured in the treated cells (FIG. 13). Syndecan-2 showed decreased expression in MSCs treated with cre recombinase and lanthanam further increased this effect.

Figure 14:
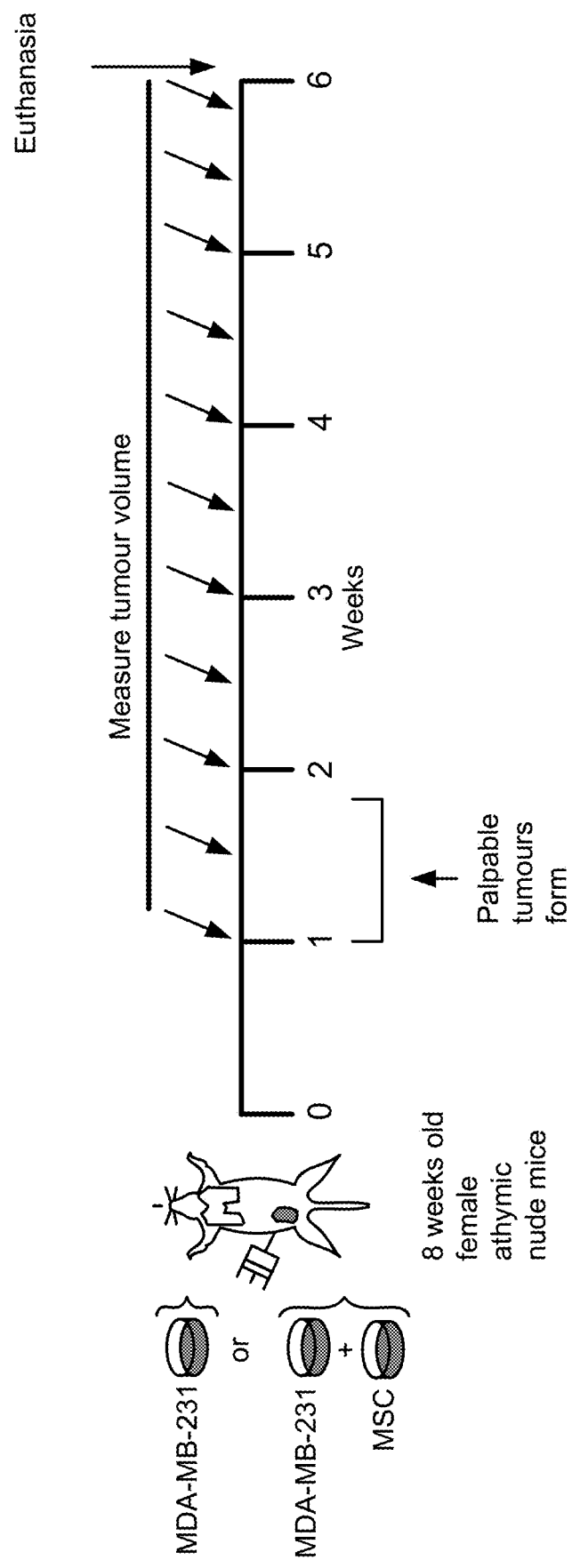
FIG. 14 illustrates a schematic of an in vivo test of Sdc2 knockdown in a mouse model of breast cancer.

FIG. 14 illustrates a schematic of an in vivo test of Sdc2 knockdown in a mouse model of breast cancer.

Certain Definitions

As used herein "treatment" or "treating" or "treated" refers to therapeutic treatment wherein the object is to slow (lessen) the progression of, stop the progression of, reverse the progression of, or alleviate or resolve an undesired physiological condition, disorder or disease, to alleviate at least one symptom thereof, up to and including to resolve or 'cure' an undesired physiological condition, or to otherwise obtain beneficial or desired clinical results. For the purposes described herein, beneficial or desired clinical results include, but are not limited to, alleviation of symptoms; diminishment of the extent of the condition, disorder or disease; stabilization of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

"In combination with", "combination therapy" and "combination products" refer, in certain embodiments, to the concurrent administration to a patient of a first therapeutic and the compounds as used herein. When administered in combination, each component is alternatively administered at the same time or sequentially in any order at different points in time. Thus, each component, in some cases, is administered separately but sufficiently closely in time so as to provide the desired therapeutic effect.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients are alternatively solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The term "antibody" is used in the broadest sense and specifically covers monoclonal antibodies (including full length monoclonal antibodies), polyclonal antibodies, multi specific antibodies (e.g., bispecific antibodies), peptibodies, human antibodies, humanized antibodies, camelid antibodies (including camelid single domain antibodies), alternative scaffold antibodies (e.g., affibodies, avimers, Fn3 domains, DARPins, Kunitz domains, SMIPs, Domain antibodies, BiTEs, Adnectins, Nanobodies, Stable scFvs, Anticalins) and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity.

As used herein, the term "about" a quantity refers to that quantity plus or minus up to 10% of that quantity.

EXAMPLES

Example 1: Antagonists to Syndecan-2 Suppress T Cell Differentiation

Introduction 1.1 The following examples were carried out to illustrate an antagonist to syndecan-2, specifically crosslinking of syndecan-2 with an anti-syndecan-2 antibody, suppressed T cell differentiation.

Materials and Methods

Donors Used

Three donors were used for the purpose of this study. Blood was isolated from each of the three individuals and each set of experiments was carried out three times on the CD4$^+$ cells harvested from each donor. Donor 1 was a male smoker in his twenties, donor 2 was a female smoker in her twenties, while subject 3 was a male smoker in his forties.

CD4$^+$ T Cell Isolation

For each Donor used, blood was collected in BD Vacutainer EDTA tubes and was left at room temperature until ready to process.

In each case, the blood was diluted 1:1 with phosphate buffered saline (PBS) and 2.5 ml of Ficoll-Hypaque™ reagent was added to each falcon tube used. Following this, 8 ml of blood was gently layered on top of this dense reagent. Each tube was then centrifuged at 700 rcf (relative centrifugal force) for 25 minutes, at room temperature in the absence of a brake to avoid disturbing the large pellet of red blood cells at the bottom of the tubes. After centrifugation, a buffy coat containing PBMCs formed. This buffy coat was gently removed using a pipette, ensuring as little Ficoll-Hypaque™ reagent as possible was taken up along with the PBMCs. The cells were then washed in PBS and centrifuged again at 400 rcf for 5 minutes. Following centrifugation, the waste PBS was disposed of and the PBMC pellet was re-suspended in 1 ml of PBS. From the total cell volume of 1 ml, 10 μl of cells was added to 980 μl PBS and 10 μl of trypan blue dye to make a 1/100 dilution of cells. 10 μl of this solution was pipetted into a haemocytometer and viewed under a 10× magnification on a microscope. The following equation was used to count the cells:

$$\frac{n \times 10^4 \times N}{s},$$

That is, $n \times 10^4 \times N/S$, wherein S=number of square chambers counted, N=dilution factor, and n=number of visible viable cells. Following this cell count, the cells were washed again in PBS and centrifuged at 300 rcf for 10 minutes.

The pellet formed during centrifugation was resuspended in 40 μl of MACS buffer per $10^7$ or 10 million cells. Following this, 10 μl of CD4$^+$ T cell Biotin-Antibody Cocktail (Miltenyi Biotec) per $10^7$ cells was added and the mixture was incubated for 5 minutes in the fridge at 4° C. After incubation, 30 μl of MACS buffer was added per $10^7$ cells along with 20 μl of CD4$^+$ Microbead Cocktail (Miltenyi Biotec) per $10^7$ cells and incubated for 10 minutes in the fridge at 4° C. During this incubation time, the LS column containing the iron wool mesh was placed in the magnetic field and washed through with 3 ml of MACS buffer. Following the incubation, the cell suspension was applied to the column, along with another 3 ml of MACs buffer and the flow through was collected. This flow through was washed in PBS and centrifuged at 400 rcf for 5 minutes. The pellet formed during centrifugation was resuspended in 1 ml of PBS. 10 μl of this 1 ml of cells suspended in PBS was added to 480 μl of PBS and 10 μl of trypan blue dye, to make a 1/50 dilution of cells. 10 μl of this solution was pipetted into the haemocytometer and counted again using the equation outlined above. In all experiments, 3 wells of no-stain controls were included, therefore at this point, 300,000 cells were removed from the tube of cells prior to CFSE staining to allow for each well to contain 100,000 cells.

Following this the cells were stained with CFSE (carboxyfluorescein succinimidyl ester), which is a widely used fluorescent cell staining dye (Parish, 1999). This staining allows the cellular proliferation of the cells to be analysed as the quantity of dye is progressively halved in each daughter cell after every division and thus the number of proliferation events of the cells can therefore be recorded using flow cytometry (section iv) (Lyons and Parish, 1994).

The CD4$^+$ T cells isolated by MACS were then re-suspended in pre-warmed PBS supplemented with 0.1% BSA, using 1 ml solution for each 5×$10^7$ cells. Each vial of CFSE was supplemented with 8 μl of DMSO (dimethyl sulfoxide) was vortexed for 30 seconds. From this vial, 2 μl/ml was added to the tube containing the cells. This tube was then incubated for 37° C. in a water bath for 6 minutes. Following this incubation, the same volume of ice-cold 10% complete media as BSA/PBS solution was added. The tube of cells was then centrifuged at 400 rcf for 5 minutes and resuspended in 10 ml of T cell media (TCM). This flow through was washed again in TCM and centrifuged at 400 rcf for 5 mins. The pellet formed during centrifugation was resuspended in 1 ml of PBS. From this solution, 10 μl was added to 480 μl of PBS and 10 μl of trypan blue dye, to make a 1/50 dilution of cells. 10 μl of this solution was pipetted into the haemocytometer and counted again using the equation outlined above.

In each case, these CD4$^+$ T cells were then prepared for addition to the antibody-coated plates, which had been coated overnight. Excess antibody was disposed of and the wells were washed in PBS prior to the addition of cells. T cell media was added to the cells to achieve 100,000 cells per well or 1×$10^6$ cells/ml.

The Optimisation Phase of the Project

The activation and stimulation of naïve CD4$^+$ T cells to differentiate into the four T-helper cell subsets i.e. Th1, Th2, Th17 and Treg, requires the addition of antibodies (α-CD3 and α-CD28) and cytokines. However, each T-helper cell subset requires a unique combination of cytokines combined with a unique concentration of antibody to obtain optimal differentiation, viability and proliferation. Therefore, in optimising this experiment, a broad range and combinations of cytokines were used to obtain such optimal results for each of the T-helper subsets. The results of the optimisation phase of this experiment determined the best concentration and combination of antibodies and cytokines to move to the experimental phase of the experiment.

The Experimental Phase of the Project

Three donors were used in the experimental phase of the experiment. One donor's blood was used at a time i.e. blood was extracted, cells were isolated, stimulated and then analysed before moving on to the next donor. For each donor, a plate for each of the T-helper cell subsets was coated with antibody. Some wells of the plates were coated with anti-CD3 (α-CD3) alone while others were coated with α-CD3 with either isotype control antibody or α-syndecan-2 antibody. The purpose of this was to see the effect of syndecan-2 on the differentiation of naïve CD4$^+$ T cells into the T-helper cell subsets by comparing engaged and un-engaged syndecan-2. In the addition of the antibodies to the wells labelled "24, 48, 72 and 96 hour samples for PCR", a concentration of 0.5 μg/ml of α-CD3 was added per well with PBS to make up a final volume of 100 μl per well. A concentration of 0.5 μg/ml of α-CD3 was also added to the "No stain control" with PBS to make up 100 μl, containing cells removed prior to CFSE staining. 5 μg/ml of the isotype control antibody with 0.5 μg/ml concentration of α-CD3 was added to the isotype assigned wells. 5 μg/ml of the isotype control antibody with 0.5 μg/ml concentration of α-CD3 was added to the isotype assigned wells. These plates were then left overnight at 4° C. in the refrigerator to allow the antibodies to adhere to the plates.

Following the overnight incubation, the CD4$^+$ T cells were isolated from the donors using Ficoll-Hypaque™ and MACS. 100 μl containing 100,000 cells per well of CD4$^+$ T cells were added to the assigned wells. 100 μl of media was then added per well. The media added was made up with cytokines specific for each T cell subset, therefore, there was specific media made up for each plate as there was a plate for each of these subsets in the case of each donor. The purpose of adding anti-IL-17, anti-IL-10, anti-IL-4 and anti-IFN-γ was to prevent any inhibitory effects of certain cytokines on the stimulation of the T helper cell subtypes. There was a total volume of 200 μl in each well. These plates were then placed in an incubator at 37° C. for 4 days. At 24, 48, 72 and 96 hours after this point of placing the plates in the incubator, the samples were taken off. These samples were centrifuged at 400 rcf for 5 minutes to allow for the formation of a pellet of cells and the separation of the media from the cells. For each time-point and T-helper cell subset, the media was stored for analysis of the cytokines present in the media using ELISA while cells were stored in 100 µl RNA Later® for analysis of syndecan-2 kinetics by quantitative polymerase chain reaction (qPCR). The media and cells were stored in the −80° C. freezer until required.

Analysis of Activation, Proliferation and Differentiation of CD4+ T Cells

In this study, MACS facilitated the isolation of CD4+ T cells and flow cytometry was used for analytical purposes in this study.

The plates that were incubated at 37° C. for 96 hours were removed from the incubator. Their contents were counted and re-suspended at 500,000 cells/ml. Therefore, each 200 µl contained 100,000 cells. Following this, analysis and staining of maturation markers, surface syndecan-2 and intracellular syndecan-2 took place.

(a) Surface Syndecan-2 Analysis

In preparing for surface syndecan-2 analysis, cells were restimulated for 5 hours. The purpose of this was to re-stimulate the cells prior to analysis by flow cytometry. The reason underlying this is that the cytokine profiles were being analysed in these cases. Re-stimulation prior to cytokine analysis causes the T-helper cell subsets to increase the rate of cytokine production that may have decreased over the course of the 96-hour incubation time. The cells being used to analyse surface syndecan-2 levels were re-stimulated for 5 hours with plate-bound α-CD3 that was coated overnight at 4° C. in the refrigerator with 5 µg/ml µ-CD3 antibody. The cells were added for restimulation at 100,000 cells/well. Following restimulation, the cells were transferred to a vee-bottomed plate, washed in PBS, centrifuged at 400 rcf for 5 minutes and resuspended in 90 µl PBS. Surface syndecan-2 staining was then carried out by adding a 10 µl solution of the following reagents to each well of the vee-bottomed plate.

TABLE 1

Reagents added to wells for surface syndecan-2 staining.
Surface syndecan-2 staining

| | |
|---|---|
| Fixable Viability Dye on APC-Cy7 Fluorochrome | 5 µg/ml |
| Anti-syndecan-2 antibody on APC Fluorochrome | 20 µg/ml |
| Cytokines on PE Fluorochrome | 5 µg/ml α-IFN-Y to $Th_1$ cultures/ 5 µg/ml α-IL-4 to $Th_2$ cultures/ 10 µg/ml α-IL-17 to $Th_{17}$ cultures & 5 µg/ml α-IL-10 to $T_{reg}$ cultures |
| CD4 on PECy7 Fluorochrome | 2 µg/ml |

The plate was placed in the refrigerator at 4° C. for 30 minutes. Following refrigeration, 100 µl of FACS buffer was added per well. The plate was centrifuged at 400 rcf for 5 minutes. The media was disposed of to leave the pellet of cells in the plate and 100 µl of clean FACS buffer was added per well. FACS tubes were labelled according to each well contained in the plate. 100 µl of FACS buffer was added per FACS tube along with the contents of one well per tube for analysis by flow cytometry.

(b) Analysis of Maturation Marker Expression

In carrying out analysis of expression of maturation markers, syndecan-2 was crosslinked with an anti-syndecan-2 antibody to analyse the effects of syndecan-2 on the expression of maturation markers CD25 and CD80. The cells were added at 100,000 cells/well from the 96 hour culture to a vee-bottomed plate, washed in PBS, centrifuged at 400 rcf for 5 minutes and resuspended in 90 µl PBS. Maturation marker staining was then carried out by adding a 10 µl solution of the following reagents to each well of the vee-bottomed plate.

TABLE 2

Reagents added to wells for staining of maturation markers CD25 and CD80.
Staining for maturation markers CD25 and CD80

| | |
|---|---|
| Fixable Viability Dye on APC Cy7 Fluorochrome | 5 µg/ml |
| CD80 antibody on PE Cy7 Fluorochrome | 5 µg/ml |
| CD25 antibody on APC Fluorochrome | 5 µg/ml |

The plate was placed in the refrigerator at 4° C. for 30 minutes. Following refrigeration, 100 µl of FACS buffer was added per well. The plate was centrifuged at 400 rcf for 5 minutes. The media was disposed of to leave the pellet of cells in the plate and 100 µl of clean FACS buffer was added per well. FACS tubes were labelled according to each well contained in the plate. 100 µl of FACS buffer was added per FACS tube along with the contents of one well per tube for analysis by flow cytometry.

(c) Analysis of Intracellular Syndecan-2

In preparing for intracellular syndecan-2 analysis, cells were restimulated for 5 hours. The cells being used to analyse intracellular syndecan-2 levels were re-stimulated with plate-bound µ-CD3 that was coated overnight at 4° C. in the refrigerator with 5 µg/ml α-CD3 antibody, at 100,000 cells/well. The wells assigned to intracellular syndecan-2 and cytokine analysis required an extra step—the addition of GolgiPlug™. Addition of BD GolgiPlug™, a protein transport inhibitor containing brefeldin A, to in vitro- or in vivo-stimulated lymphoid cells blocks their intracellular protein transport processes. This results in the accumulation of cytokines in the Golgi complex, which enhances the detectability of cytokine-producing cells with immunofluorescent staining and analysis by flow cytometry. 1 µl of GolgiPlug™ was added per ml of media into the α-CD3 coated plates and were left to re-stimulate for 5.5 hours. The cells were then transferred to a vee-bottomed plate, washed in PBS, centrifuged at 400 rcf for 5 minutes and resuspended in 90 µl PBS. Intracellular syndecan-2 staining was then carried out by adding a 10 µl solution of the following reagents to each well of the vee-bottomed plate. These wells received 100 µl of BD Fix/Perm™ and were placed in the refrigerator at 4° C. for 20 minutes in order to fixate and permeabilise the cells to facilitate the entry of antibodies for the intracellular staining of syndecan-2 or cytokines. BD Perm/Wash™, was used to wash the cells following refrigeration.

TABLE 3

Reagents added to wells for surface syndecan-2 staining.
Intracellular syndecan-2 staining

| | |
|---|---|
| Fixable Viability Dye on APC-Cy7 Fluorochrome | 5 µg/ml |
| Anti-syndecan-2 antibody on APC Fluorochrome | 20 µg/ml |
| Cytokines on PE Fluorochrome | 5 µg/ml α-IFN-Y to $Th_1$ cultures/ 5 µg/ml α-IL-4 to $Th_2$ cultures/ 10 µg/ml α-IL-17 to $Th_{17}$ cultures & 5 µg/ml α-IL-10 to $T_{reg}$ cultures |
| CD4 on PECy7 Fluorochrome | 2 µg/ml |

Following this, 50 µl of BD Perm/Wash™ was added with 10 µl FACS containing 7 µl solution of PBS containing the above reagents per well (Table 2.7). The plate was placed in the refrigerator at 4° C. for 30 minutes to allow entry of antibodies into cells. Following this the cells were washed again using BD Perm/Wash™. Finally, the contents of these final wells were transferred into FACS tubes and were analysed using FACS. Software compatible with the BD-FACS Canto® machine, FlowJo® was used to compile results.

Several ELISAs were carried out to determine the presence of differentiated T cells by testing for the cytokines they produce. IFN-γ is an indicator for the presence of Th1 cells, IL-4 indicated the presence of Th2 cells, IL-17 indicates the presence of Th17 cells and IL-10 is an indicator for the presence of Treg cells. The kits used in carrying out the ELISAs in this study were the DuoSet® ELISA development systems by R+D Systems, specific to each cytokine being tested for. In each ELISA carried out, a separate plate was used for each of the cytokines being tested for.

A 96-well Nunc Maxisorp plate was coated overnight with capture antibody diluted overnight in PBS at room temperature. In each case, 4 μg/ml concentration of antibody was made up. 100 μl was added to each well and left overnight. Following the overnight coating of the plates, each well was washed 3 times with 200 μl of wash buffer (0.05% Tween in PBS). Following washing, each plate was blotted on paper to remove all excess liquid. Following this the plates were blocked with 200 μl reagent diluent (Bovin Serum Albumin (BSA) in PBS with concentrations made up as per manufacturers guidelines) for 1 hour at room temperature. Following this blocking, the plates were washed again 3 times using 200 μl wash buffer each time.

At this point, the standards and samples were added for 2 hours at room temperature. Standards were made up by serial dilutions and 100 μl of standard or sample was added to each well. Reagent diluent containing 1% BSA in PBS was used for hIFN-γ and IL-4 ELISAs and 0.1% BSA in PBS was used for hIL-17 and hIL-10 ELISAs.

Following the addition of sample and standards for 2 hours, the plates were washed again 3 times with 200 μl of wash buffer each time. Following this, 100 μl of detection antibody was added for 2 hours at room temperature. 166 μl of detection antibody specific to each cytokine was added to 10 ml reagent diluent and 100 μl was added to each well of each 96-well plate (hIFN-γ RD was supplemented with 2% heat inactivated normal goat serum). Following this 2 hour incubation time, the plates were washed again. At this point, 100 μl of streptavadin-HRP diluted in reagent diluent was added for 20 minutes at room temperature (50 μl of Sav-HRP+9950 μl RD to make a 1:200 dilution). Following this, the plates were washed again. 100 μl of substrate reagent was added for 20 minutes at room temperature protected from light. After this, 50 μl of stop solution (1M sulfuric acid) was added. The plates were read at 450 nm and 550 nm to analyse cytokine concentrations and standard curves were constructed for each cytokine from which the unknown concentrations of cytokines from supernatants could be measured Results Optimisation Phase Determining Optimal Antibody Concentration In determining the optimal antibody combination and concentration, various concentrations of each antibody, α-CD3 and α-CD28, were tested in this experiment.

0.5 μg/ml α-CD3 stimulated optimal proliferation of CD4⁺ T cells. There was no statistical difference in the viability of cells receiving 0 μg/ml α-CD3 and 0.5 μg/ml α-CD3, therefore treatment with this concentration did not affect viability of cells. Therefore, 0.5 μg/ml α-CD3 and 0 μg/ml α-CD28 were selected as the concentrations of antibody that caused proliferation of CD4⁺ T cells and did not have any adverse effect on cell viability.

Determining the Optimal Combination and Concentration of Cytokines

Many concentrations and combinations of cytokines were used in determining the optimum combination and concentration of cytokines that results in the highest proliferation and viability during T helper differentiation. Proliferation was measured using CFSE dye while viability was measured using FVD and analysis was then carried out using flow cytometry. ELISA was carried out on T-helper subsets to measure effector cytokines produced by each subset; Th1 cells produce IFN-γ, Th2 cells produce IL-4, Th17 cells produce IL-17 and Treg cells produce IL-10. Tukey's multiple comparisons test was used in determining the significance of differences in cytokine concentrations between conditions.

TABLE 4

Various concentrations of IL-2, IL-12 and IFN-γ used in determining optimal concentration for stimulating naïve CD4⁺ T cells to polarize into Th₁ cells.

| | C1 | C2 | C3 | C4 | C5 | C6 | C7 | C8 | C9 | C10 | C11 | C12 |
|---|---|---|---|---|---|---|---|---|---|---|---|---|
| IL-2 (ng/ml) | 2 | 2 | 2 | 2 | 5 | 5 | 5 | 5 | 10 | 10 | 10 | 10 |
| IL-12 (ng/ml) | 5 | 5 | 10 | 10 | 5 | 5 | 10 | 10 | 5 | 5 | 10 | 10 |
| IFNγ (ng/ml) | 5 | 10 | 5 | 10 | 5 | 10 | 5 | 10 | 5 | 10 | 5 | 10 |

| | C13 | C14 | C15 | C16 | C17 | C18 |
|---|---|---|---|---|---|---|
| xIL-2 (ng/ml) | 2 | 2 | 5 | 5 | 10 | 10 |
| IL-4 (ng/ml) | 25 | 50 | 25 | 50 | 25 | 50 |

TABLE 5

Various concentrations of IL-2 and IL-4 used in determining optimal concentration for stimulating naïve CD4⁺ T cells to polarize into Th₂ cells.

| | C19 | C20 | C21 | C22 | C23 | C24 |
|---|---|---|---|---|---|---|
| IL-1β (ng/ml) | 10 | 10 | 10 | 10 | 10 | 10 |
| IL-6 (ng/ml) | 10 | 25 | 10 | 25 | 10 | 25 |
| IL-23 (ng/ml) | 10 | 10 | 25 | 25 | 50 | 50 |
| TGFβ (ng/ml) | 5 | 5 | 5 | 5 | 5 | 5 |

Table 6 Various concentrations of IL-1β, IL-6, IL-23 and TGFβ used in determining optimal concentration for stimulating naïve CD4⁺ T cells to polarize into Th₁₇ cells.

| | C25 | C26 | C27 | C28 | C29 | C30 |
|---|---|---|---|---|---|---|
| IL-2 (ng/ml) | 2 | 2 | 5 | 5 | 10 | 10 |
| TGFβ (ng/ml) | 2 | 5 | 2 | 5 | 2 | 5 |

Table 7 Various concentrations of IL-2 and TGFβ used in determining optimal concentration for stimulating naïve CD4⁺ T cells to polarize into T$_{reg}$ cells.

Th₁ cultures: The maximum concentration of IL-2 yields the most significant cytokine production, while the maximum concentration of recombinant IL-12 and IFN-γ has no effect on cytokine production relative to their lower concentrations. Therefore, as the proliferation of C9 was significantly lower than in other conditions, C10 was selected as the optimal cytokine concentration for the experimental phase of the project.

Th$_2$ cultures: All conditions have similar viability with no significant difference seen between conditions. Thus, it is clear that Th2 cells require further optimisation.

Th$_{17}$ cultures: As the most significant levels of IL-17 were produced following the addition of 25 ng/ml recombinant IL-6 and IL-23, C22 was selected as the optimal concentration of cytokine to stimulate the differentiation of Th$_{17}$ cells.

T$_{reg}$ cultures: As the optimal results were seen in the cases of C27 and C28, with no significant difference between these conditions, C27 was therefore selected as the optimal cytokine concentration for the experimental phase of the project.

Kinetics of Syndecan-2 During T Cell Differentiation

Intracellular and surface syndecan-2 was analysed using flow cytometry. In analysing the kinetics of syndecan-2, various gates had to be used. The addition of gates allowed certain cells to be selected from others. The first gate applied to the cells allowed the viable cells to be selected from other cells using viability dye which was placed on the APC Cy7 fluorochrome. The second gate selected the single cells from the viable cells by plotting the data on forward scatter height against forward scatter area. This gate was employed on the principle of the linear relationship between the height and area and therefore any cells outside of this line can be classed doublets or cell that have adhered to one another. The third gate facilitated the separation of the single viable cells into their respective generation which was analysed by CFSE which was placed on the FITC fluorochrome. From this, the mean fluorescence intensity of intracellular and surface syndecan-2 was measured and analysed, where syndecan-2 was placed on the APC fluorochrome.

We compared intracellular syndecan-2 levels to surface syndecan-2 levels in Th1 cultures that have been restimulated for 5 hours. There are significantly higher levels of intracellular syndecan-2 seen in each generation of cells in each donor (****$p<0.0001$).

We compared intracellular syndecan-2 levels to surface syndecan-2 levels in Th17 cultures that have been restimulated for 5 hours. There are significantly higher levels of intracellular syndecan-2 seen in each generation of cells in each donor.

We compared intracellular syndecan-2 levels to surface syndecan-2 levels in Treg cultures that have been restimulated for 5 hours. There are significantly higher levels of intracellular syndecan-2 seen in each generation of Treg cells in Donor 1, while significantly greater levels of intracellular syndecan-2 is seen in all generations of Donor 2 cells apart from G1.

We found that a significantly higher level of intracellular syndecan-2 is observed across generations of each culture. However, another trend is observed in analysing the kinetics of syndecan-2. Syndecan-2 increased in its expression as the T cells differentiated and proliferated into the effector T cell subsets.

Levels of syndecan-2 mRNA levels were measured by qPCR. There was no significant difference seen in either donor. However, some trends can be seen in the data. An increase is seen at the 24 hour time-point across cultures in each donor, particularly in Donor 2. Another trend is seen toward increased mRNA levels in Th17 cells in each donor, particularly at the 48 hour time-point.

Analysis of Crosslinking Syndecan-2
Proliferation of CD4$^+$ T Cells

FIG. 1 illustrates: Schematic of proliferation seen across Donor 1 cultures of Th1, Th17 and Treg cells with proliferation represented as the percentage of cells that divided more than 3 times (left). Histogram of significant difference, as indicated in left panel, in CFSE levels represented on the FITC fluorochrome in Th17 cultures stimulated by isotype control and α-syndecan-2 antibody with greater levels indicating less proliferation (*$p<0.05$, $p<0.01$, *$p<0.001$, ****$p<0.0001$).

FIG. 1 compares proliferation of Th1, Th17 and Treg cells when anti-CD3 stimulated them in the presence of either the isotype control antibody or the α-syndecan-2 antibody. Treatment of cells with the α-syndecan-2 antibody resulted in a significant decrease in the proliferation of Th17 cells. This significant difference is represented by CF SE dilution on the FITC fluorochrome in the histograms shown (right).

Analysis of Maturation Markers—CD25

FIG. 2 illustrates A) Schematic of maturation marker, CD25 expression, seen across Donor 1 cultures of Th1, Th17 and Treg cells represented as frequency of viable T-cells (left). Histogram of significant difference, as indicated in left panel, in CD25 in Th17 cultures stimulated by isotype control and α-syndecan-2 antibody. B) Data generated from Donor 2 cells (*$p<0.05$,  $p<0.01$, * $p<0.001$, ****$p<0.0001$).

FIG. 2 compares expression of a maturation marker, CD25, on Th1, Th17 and Treg cells when anti-CD3 stimulated them in the presence of either the isotype control antibody or the α-syndecan-2 antibody. In each donor, it can be seen that treatment with the α-syndecan-2 antibody resulted in a significant decrease in the expression of CD25 on Th17 cells. However, the most significant result is seen in the case of Donor 1. This significant difference is represented on the APC fluorochrome in the histograms shown (right).

Analysis of Maturation Markers—CD80

FIG. 3 illustrates: A) Schematic of maturation marker, CD80 expression, seen across Donor 1 cultures of Th1, Th17 and Treg cells represented as frequency of viable T-cells (left). Histogram of significant difference, as indicated in left panel, in CD80 represented on the PECy7 fluorochrome in Th17 cultures stimulated by isotype control and α-syndecan-2 antibody. B) Data generated from Donor 2 cells (*$p<0.05$,  $p<0.01$, * $p<0.001$, ****$p<0.0001$).

FIG. 3 compares expression of a maturation marker, CD80, on Th1, Th17 and Treg cells when stimulated by either the isotype control antibody or the α-syndecan-2 antibody with the data presented as the frequency of viable T cells. In Donor 1, it can be seen that treatment with the α-syndecan-2 antibody resulted in a significant decrease in the expression of CD80 on Th17 cells. This significant difference is represented on the PECy7 fluorochrome for Th17 cells.

Analysis of Cytokine Production by ELISA
Th$_1$ Cultures

FIG. 4 illustrates: A) Schematic of concentrations of IFN-γ in supernatants removed following 4 day incubation of Donor 1 Th1 cultures following treatment with isotype control or α-syndecan-2 antibody, B) Schematic of concentrations of IFN-γ in supernatants removed following 4 day incubation of Donor 2 Th1 cultures following treatment with isotype control or α-syndecan-2 antibody, FIG. 4 compares IFN-γ concentrations in Th1 cultures following treatment with either the control isotype antibody or α-syndecan-2 antibody. There was no significant change observed in the concentration of IFN-γ following α-syndecan-2 antibody treatment in either donor.

Analysis of Cytokine Levels

Th$_{17}$ Cultures

FIG. 5 illustrates: A) Schematic of concentrations of IL-17 in supernatants removed following 4 day incubation of Donor 1 Th17 cultures following treatment with isotype control or α-syndecan-2 antibody, B) Data generated from Donor 2 cells.

FIG. 5 compares IL-17 concentrations in Th17 cultures following treatment with either the control isotype antibody or α-syndecan-2 antibody. It can be observed that following α-syndecan-2 antibody treatment, IL-17 concentrations are significantly decreased in both donors. However, the most significant result is observed in the case of Donor 1.

Conclusions

Optimisation Phase

The results of the optimisation phase indicated that plate-bound α-CD28 antibody was not required for T cell activation, although many publications use a combination of soluble α-CD28 and α-CD3 antibodies in activating naïve CD4$^+$ T cells (Khan et al., 2011, Nish et al., 2014). Therefore, due to the addition of the α-CD28 antibody having no additive effect to plate-bound α-CD3 stimulus alone on the proliferation of the cells, it was omitted from the project.

In determining the optimal concentration and combination of cytokines in the T helper subsets, the optimisation of Th2 cells was unsuccessful. Therefore, Th2 cells were excluded from the study.

Kinetics of Syndecan-2 During T Cell Differentiation

Syndecan-2 is expressed both intracellularly and on the cell surface of the T-helper subsets. However, MFI of intracellular syndecan-2 is significantly greater in most generations of cells from each donor when compared to surface syndecan-2. The presence of syndecan-2 intracellularly may be due to mechanisms of syndecan endocytic routes as suggested by Lambaerts et al (Lambaerts et al., 2009). Following activation and clustering, syndecans reportedly appear to be internalised by clathrin- and caveolin-independent mechanisms. Suggestions have been made of the occurrence of macropinocytosis in the internalisation of syndecans. However, syndecan-1 and -2 have been shown to mediate opposing effects on post endocytic gene delivery. Polyethyleneimines (PEIs) are non-viral vectors for gene transfer and HS proteoglycans, such as syndecans, have been suggested to be the receptors for PEI-DNA complexes (polyplexes). Paris et al have shown that syndecan-1 and -2 have a direct involvement in polyplex binding and that syndecan-2 strongly delays polyplex endocytosis and has an inhibitory effect on PEI-mediated gene expression (Paris et al., 2008). However, the fate syndecans following internalisation is not fully understood.

qPCR involved measuring levels of syndecan-2 mRNA. Therefore, this was a general measure of syndecan-2 mRNA and was not specific to either measuring intracellular or surface mRNA. Some trends can be seen in the data. An increase was seen at the 24 hour time-point across cultures in each donor, particularly in Donor 2. The trends seen in Th17 cells show increased levels of syndecan-2 mRNA, particularly at the 48 hour time-point. This trend towards increased syndecan-2 may correspond to the inhibitory effects of syndecan-2 on Th17 cells. These effects on Th17 cells may be occurring when syndecan-2 is at its highest levels at the 48 hour time-point.

Effects of Crosslinking Syndecan-2 with Anti-Syndecan-2 Antibody

Crosslinking syndecan with the α-syndecan-2 antibody, compared to the isotype control antibody, leads to significantly decreasing proliferation of Th17 cells. CD25 expression was also significantly decreased in Th17 cells as a result of crosslinking with α-syndecan-2. Another maturation marker, CD80, was also significantly decreased in Donor 1 Th17 cells. CD25 and CD80 are maturation markers and a significant decrease in these markers would therefore suggest that α-syndecan-2 is inhibiting the growth and maturation of Th17 cells. Furthermore, ELISA results show that there was significantly lower concentrations of IL-17 in Th17 cells in both donors as a result of crosslinking with the α-syndecan-2 antibody. Therefore, antibody treatment with α-syndecan-2 also inhibited Th17 effector cell differentiation.

Crosslinking syndecan with the α-syndecan-2 antibody in Treg cultures does not have any significant effect on proliferation or CD25 expression. The effect of crosslinking Treg cultures with the α-syndecan-2 antibody may have opposing effects on CD80 to the effects seen in Th17 cultures.

Crosslinking syndecan with the α-syndecan-2 antibody in Th1 cultures had no significant effect on proliferation, CD25 expression, CD80 expression or IFN-γ production. This suggests that syndecan-2 does not have a role to play in Th1 polarisation and thus, the effects on Th17 and Treg cells may be specific. This may be related to the role of TGF-β in the polarisation of Th17 and Treg cells as TGF-β was used to differentiate both Th17 and Treg cells but not Th1. Syndecan-2 has been shown to have an inhibitory role to play in TGF-β signalling and therefore may have a role to play in the inhibitory effects of α-syndecan-2 treatment on Th17 proliferation, maturation markers and cytokine production (Shi et al., 2013, Mytilinaiou et al., 2013). Therapeutic administration of syndecan-2 was shown to abrogate TGF-β-dependent lung fibrosis in mice by inhibiting TGF-β signalling (Shi et al., 2013)

Inter-Individual Variation Between Donors

The responses of individual T cells to TCR stimuli may vary. In all cases, Donor 1 Th17 cultures seem to be particularly sensitive to the stimulus of the α-syndecan-2 antibody. Results are more statistically significant in the case of Donor 1 Th17 cells in terms of decreases seen in proliferation, CD25 expression, CD80 expression and also IL-17 production when compared to Donor 2 results.

Originally, the experimental design of this study included the participation of three blood donors. Cells were isolated from the blood of Donors 1-3 and were stimulated in the exact same manner. However, the vast majority of Donor 3 cells did not activate or proliferate following analysis by flow cytometry. However, a very small proportion of proliferation was observed in IL-2 treated cultures (Th1 and Treg cultures). Therefore, the CD4$^+$ T cells from this donor may be particularly sensitive to this stimulus and may require a much greater concentration of IL-2 for sufficient proliferation for analysis of properties of syndecan-2 in these cells. Another possibility could be that Donor 3 cells may require stimulation by α-CD28 antibody. However, repeating the Donor 3 experiment with altered stimuli to facilitate growth and proliferation would involve altering the experimental design and therefore results could not be compared to Donors 1 and 2. Therefore, Donor 3 was excluded from the study.

Conclusion

It can be concluded that syndecan-2 does indeed have a role to play in T cell differentiation. Syndecan-2 was expressed intracellularly and on the cell surface as the T-helper cell subtypes differentiated and proliferated. Crosslinking with an anti-syndecan-2 antibody suppressed Th17 proliferation, maturation and cytokine production.

Accordingly, the present invention provides the therapeutic and diagnostic uses of antibodies to syndecan-2 and antagonists of syndecan-2 as herein disclosed and described.

Example 2: Syndecan-2 Promotes Inflammation in Cancer

SDC2 is a novel marker for identification of stromal cells (SC) from murine and human tissue. Flow cytometry analysis, shown in FIG. 6, at left, of Sdc2$^+$CD271$^+$CD45− and Sdc2$^+$Sca1$^+$CD45$^−$ mononuclear cells from human and mouse bone marrow respectively. Identification of Sdc2$^+$gp38$^+$CD45$^−$ stromal cells (FIG. 6, center) in mouse lymph nodes and thymus by flow cytometry analysis. Finally identification of Sdc2$^+$Sca1$^+$CD45$^−$ stromal cells (FIG. 6, at right) in mouse adipose and muscle tissue by flow cytometry analysis. This illustrates that Sdc2 is a novel marker that can be used to isolate stromal cells from normal and tumor tissue.

Sdc2 is present in the stroma, epithelium and serum of breast cancers. This was shown by flow cytometry of dissected breast tumours (FIG. 7A) from PyMT-ChOVA mice revealing Sdc2$^+$epithelial (mCherry$^+$ve, CD45-ve), and Sdc2$^+$SC (mCherry-ve, CD45-ve, GP38$^+$ve). Immunohistochemistry (FIG. 7B) revealed increased levels of Sdc2 protein in human breast tumours. ELISA demonstrated high levels of Sdc2 protein in serum of patients with basal-like breast cancer (FIG. 7C).

Sdc2 enhances breast cancer cell migration and inhibits T-cell proliferation. ELISA demonstrated high levels of Sdc2 in stromal cell-conditioned media (SC-CM) (FIG. 8A). SC-CM enhanced the migration of MDA-MB-231 breast cancer cells (BCC), and pre-incubation of BCC with recombinant Sdc2 enhances migration towards SC-CM (FIG. 8B). Knockdown of Sdc2 inhibited the ability of BCC to migrate towards serum containing media (FIG. 8C). Flow cytometry of CFSE-labeled CD4$^+$ T cells, revealed CD3/CD28-mediated stimulation of proliferation is inhibited by SC overexpressing Sdc2 (FIG. 8D).

Sdc2 is required for TGF-β-induced epithelial to mesenchymal transition (EMT). MDA-MB-231 cells transduced with AdshSdc2 showed an attenuated TGFβ-induced increase in SMAD7, PAI-1 and CTFG RNA when compared to control cells expressing empty vector (EV). RT-qPCR demonstrated efficient knockdown of Sdc2 (FIG. 9A). RT-qPCR and Western blot analysis demonstrated that Sdc2 knockdown attenuates TGFβ-mediated induction of EMT markers, SNAIL-1 and Fibronectin respectively (FIG. 9B).

Sdc2 peptides have anti migratory and anti-inflammatory properties in vitro.

Generation of deletion mutants containing different functional domains of Sdc2. Fragments 1-6 contain the signal peptide, whereas fragments 7-8 do not (FIG. 10A). Various Sdc2 functional fragments inhibited migration of MDA-MB-231 towards SC-CM in cis (FIG. 10B). Various Sdc2 functional fragments inhibited migration of MDA-MB-231 towards SC-CM in trans (FIG. 10C). (2-sided Students t-test *p<0.05) Various Sdc2 fragments significantly inhibited TNF-α/IL-1β-induced NF-κB activation (FIG. 10D).

Sdc2 peptides attenuated upregulation of TGF-β regulated genes. RT-qPCR analysis demonstrated that Sdc2-Fragment 1 and Sdc2-Fragment2 caused a reduction in TGFβ-mediated SMAD7, Serpine-1 and CTGF induction (FIG. 11).

Sdc2 fl/fl mice were made using standard techniques known to one of skill in the art. Genotyping results of DNA from ear punches of Sdc2 fl/fl mice are shown in FIG. 12.

Mesenchymal Stem Cells (MSCs) were isolated from Sdc2fl/fl mice and treated with an adenovirus overexpressing cre recombinase. In some of the treated cells, lanthanum was added to the transfection. Syndecan-2 expression was measured in the treated cells (FIG. 13). Syndecan-2 showed decreased expression in MSCs treated with cre recombinase and lanthanam further increased this effect.

FIG. 14 illustrates a schematic of an in vivo test of Sdc2 knockdown in a mouse model of breast cancer.

Example 3: Sdc2 Fragment Therapeutics

Fragments of Sdc2 are selected by their ability to inhibit Syndecan-2 activity in vitro. Some such fragments include peptides with sequences as indicated herein. Sdc2 fragments are provided as a formulation for administration to a subject in need of treatment with an inhibitor of Syndecan-2 activity.

To illustrate in vitro efficacy, Sdc2 fragments are incubated tested in a tumor migration assay.

To illustrate therapeutic efficacy, Sdc2 fragments are administered in a mouse model of arthritis, such as collagen-induced arthritis.

Example 4: Anti-Sdc2 Antibody Therapeutics

Anti-Sdc2 antibodies that have the ability to inhibit Syndecan-2 activity are useful in therapeutics for administration to a subject in need of treatment with an inhibitor of Syndecan-2 activity.

To illustrate in vitro efficacy, anti-Sdc2 antibodies are incubated tested in a tumor migration assay.

To illustrate therapeutic efficacy, anti-Sdc2 antibodies are administered in a mouse model of arthritis, such as collagen-induced arthritis.

Example 5: Treatment of a Xenograft Tumor Model

An Sdc2 fragment of Example 3 is evaluated in a xenograft model.

Female immune-deficient NOD/scid mice are sub-lethally irradiated (2 Gy) and subcutaneously inoculated with 4×106 Ramos RA1 cells into the right dorsal flank. When tumors reach 100 to 200 mm3, animals are allocated into 3 treatment groups. Groups 2 and 3 (8 animals each) are intraperitoneally injected with 1.5×107 activated human T-cells. Three days later, animals from Group 3 are subsequently treated with a total of 9 intravenous doses of 50 μg Sdc2 fragment of Example 3 (qdx9d). Groups 1 and 2 are only treated with vehicle. Body weight and tumor volume are determined for 30 days.

Animals treated with the Sdc2 fragment of Example 3 have a statistically significant delay in tumor growth in comparison to the respective vehicle-treated control group.

Example 6: Treatment of Cancer (Phase I/II)

This is a Phase I/II clinical trial for studying the Sdc2 fragment of Example 3 as a treatment for colon carcinoma.
Study Outcomes:
Primary: Maximum tolerated dose of Sdc2 fragment of Example 3
Secondary: To determine whether in vitro response of Sdc2 fragment of Example 3 is associated with clinical response Phase I The maximum tolerated dose (MTD) will be determined in the phase I section of the trial.

1.1 The maximum tolerated dose (MTD) will be determined in the phase I section of the trial.

1.2 Patients who fulfill eligibility criteria will be entered into the trial to Sdc2 fragment of Example 3.

1.3 The goal is to identify the highest dose of Sdc2 fragment of Example 3 that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of Sdc2 fragment of Example 3 results in at least a 20% response rate.

Primary Outcome for the Phase II—To determine if therapy of Sdc2 fragment of Example 3 results in at least 20% of patients achieving a clinical response (blast response, minor response, partial response, or complete response)

Eligibility:

Histologically confirmed newly diagnosed aggressive colon carcinoma according to the current World Health Organisation Classification, from 2001 to 2007

Any stage of disease.

Treatment with R-CHOP or R-CHOP like regimens (+/− transplant).

Age ≥18 years

Karnofsky performance status ≥50% or ECOG performance status 0-2

Life expectancy ≥6 weeks

Example 7: Treatment of Autoimmune Disease

This is a Phase I/II clinical trial for studying the Sdc2 fragment of Example 3 as a treatment for rheumatoid arthritis.

Study Outcomes:

Primary: Maximum tolerated dose of Sdc2 fragment of Example 3

Secondary: To determine whether in vitro response of Sdc2 fragment of Example 3 is associated with clinical response Phase I The maximum tolerated dose (MTD) will be determined in the phase I section of the trial.

1.1 The maximum tolerated dose (MTD) will be determined in the phase I section of the trial.

1.2 Patients who fulfill eligibility criteria will be entered into the trial to Sdc2 fragment of Example 3.

1.3 The goal is to identify the highest dose of Sdc2 fragment of Example 3 that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of Sdc2 fragment of Example 3 results in at least a 20% response rate.

Primary Outcome for the Phase II—To determine if therapy of Sdc2 fragment of Example 3 results in at least 20% of patients achieving a clinical response (blast response, minor response, partial response, or complete response)

Eligibility:

Patients 18 years of age and older who have had rheumatoid arthritis for less than 2 years and who have four or more affected joints may be eligible for this 1-year study. Patients must have received methotrexate treatment in the past without complete success, and must not have been treated previously with Anti-Thymocyte therapy.

Example 8: Treatment of Fibrosis

This is a Phase I/II clinical trial for studying the Sdc2 fragment of Example 3 as a treatment for idiopathic pulmonary fibrosis.

Study Outcomes:

Primary: Maximum tolerated dose of Sdc2 fragment of Example 3

Secondary: To determine whether in vitro response of Sdc2 fragment of Example 3 is associated with clinical response Phase I The maximum tolerated dose (MTD) will be determined in the phase I section of the trial.

1.1 The maximum tolerated dose (MTD) will be determined in the phase I section of the trial.

1.2 Patients who fulfill eligibility criteria will be entered into the trial to Sdc2 fragment of Example 3.

1.3 The goal is to identify the highest dose of Sdc2 fragment of Example 3 that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of Sdc2 fragment of Example 3 results in at least a 20% response rate.

Primary Outcome for the Phase II—To determine if therapy of Sdc2 fragment of Example 3 results in at least 20% of patients achieving a clinical response (blast response, minor response, partial response, or complete response)

Eligibility:

Inclusion Criteria:

Signed Informed Consent consistent with ICH-GCP and local laws signed prior to entry into the trial;

Male or female patients aged >=40 years at Visit 1;

IPF diagnosis based upon the American Thoracic Society (ATS)/European Respiratory Society (ERS)/Japanese Respiratory Society (JRS)/Latin American Thoracic Society (ALAT) IPF 2011 guideline within 5 years of visit 1;

Carbon monoxide diffusing capacity (DLCO)(corrected for Haemoglobin (Hb)): 30%-79% predicted of normal, per institutional standards at the clinic site, at Visit 1;

Forced Vital Capacity (FVC) >=50% predicted of normal, per institutional standards at the clinic site, at Visit 1.

Example 9: Treatment of Cancer (Phase III)

This randomized phase III trial studies how well the Sdc2 fragment of Example 3 works compared to observation in treating patients with remaining (residual) basal-like triple-negative breast cancer after surgery. It is not yet known whether the Sdc2 fragment of Example 3 is more effective than observation in treating patients with residual triple negative basal-like breast cancer (TNBC). Patients are given intravenous doses ranging from 0.1 mg to 2 mg to determine the most effective dose.

Primary Outcome Measures:

Invasive disease free survival (IDFS) of patients with basal-like TNBC (Time Frame: From randomization to the earliest of documented disease recurrence (local, regional and/or distant), invasive contralateral breast cancer, invasive any other second primary cancer, or death, assessed up to 86 months after study activation.)

The distributions of IDFS is estimated using the Kaplan-Meier method, with 95% confidence intervals (CI) calculated using Greenwood's formula. The primary analysis of IDFS comparisons between two treatment arms is performed using stratified log-rank tests, stratifying on the randomization stratification factors. Stratified Cox proportional-hazard models are also built to estimate the hazard ratios for treatment effect for IDFS as a supportive analysis.

Secondary Outcome Measures:

Incidence of toxicity graded using the National Cancer Institute CTCAE v. 4.0 (Time Frame: Up to 86 months after study activation.)

All treatment-emergent and baseline adverse events and hematological/biochemical toxicities based on laboratory measurements are summarized for patients treated with the Sdc2 fragment of Example 3. The incidence of deaths and treatment-emergent serious adverse events is calculated along with exact 95% CI based on binomial distribution. Also, the incidence of adverse events leading to discontinuation of chemotherapy and/or withdrawal from the study is summarized and listed as well.

Overall survival (OS) of patients with basal-like TNBC with residual disease after neoadjuvant chemotherapy (Time Frame: Time from randomization to death from any cause, assessed up to 116 months after study activation.)

The distributions of OS are estimated using the Kaplan-Meier method, with 95% CI calculated using Greenwood's formula. The primary analysis of OS comparisons between two treatment arms is performed using stratified log-rank tests, stratifying on the randomization stratification factors.

Rate of basal-like gene expression using PAM50 analysis by digital mRNA quantification (Time Frame: Baseline).

The proportion of basal-like TNBC in all screened TNBC patients is calculated with exact 95% CI based on binomial distribution.

Disease Free Survival (DFS) (Time Frame: Up to 86 months after study activation)

The distributions of DFS are estimated using the Kaplan-Meier method, with 95% CI calculated using Greenwood's formula. The primary analysis of DFS comparisons between two treatment arms is performed using stratified log-rank tests, stratifying on the randomization stratification factors.

What is claimed is:

1. A method of inhibiting a Th17 cell activity in a subject in need thereof comprising administering to the subject a composition comprising (a) a fusion polypeptide comprising a first portion and a second portion, wherein the first portion binds to a syndecan-2 protein and the second portion comprises a dimerization domain and (b) a pharmaceutically acceptable buffer or excipient, wherein the first portion comprises a fragment of syndecan-2 selected from the list consisting of SEQ ID NOs: 4-6 and 8-13.

2. The method of claim 1, wherein the dimerization domain comprises an Fc domain or a leucine zipper.

3. The method of claim 1, further comprising administering a stromal stem cell population comprising stem cells at least 30% of which are positive for syndecan-2.

4. The method of claim 1, further comprising administering at least one autoimmune disease agent selected from the group consisting of a non-steroidal anti-inflammatory drug (NSAID), ibuprofen, naproxen, meloxicam, etodolac, nabumetone, sulindac, tolementin, choline magnesium trisalicylate, diclofenac, diflusinal, indomethacin, ketoprofen, oxaprozin, piroxicam, celecoxib, etoricoxib, lumiracoxib, a corticosteroid, methotrexate, hydroxychloroquine, sulfasalazine, leflunomide, a TNFa inhibitor, etanercept, adalimumab, infliximab, certolizumab pegol, golimumab, abatacept, rituximab, tociluzumab, anakinra, cyclosporine, antithymocyte globulin, mycophenolate mofetil, and cyclophosphamide.

5. The method of claim 1, further comprising administering at least one living immune effector cell selected from the list consisting of a tumor infiltrating lymphocyte (TIL), a stem central memory T cell, a CAR-T cell, a TCR-T cell, and a Natural Killer (NK) cell.

6. The method of claim 1, further comprising administering a CD4+CD25+Foxp3+ regulatory T cell.

7. The method of claim 1, wherein the pharmaceutically acceptable buffer or excipient is selected from the group consisting of maleic acid, tartaric acid, lactic acid, citric acid, acetic acid, sodium bicarbonate, sodium phosphate, histadine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylenesorbitanmonooleate.

8. The method of claim 1, wherein the composition is administered intravenously, topically, orally, bucally, or nasally.

9. The method of claim 1, wherein the composition is administered one time, daily, weekly, biweekly, or monthly.

* * * * *

SEQUENCE LISTING

```
<160> NUMBER OF SEQ ID NOS: 13

<210> SEQ ID NO 1
<211> LENGTH: 201
<212> TYPE: PRT
<213> ORGANISM: Homo sapiens

<400> SEQUENCE: 1

Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
    130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                165                 170                 175

Gly Ser Tyr Asp Leu Gly Glu Arg Lys Pro Ser Ser Ala Ala Tyr Gln
            180                 185                 190
```

Lys Ala Pro Thr Lys Glu Phe Tyr Ala
        195                 200

<210> SEQ ID NO 2
<211> LENGTH: 126
<212> TYPE: PRT
<213> ORGANISM: Homo sapiens

<400> SEQUENCE: 2

Glu Ser Arg Ala Glu Leu Thr Ser Asp Lys Asp Met Tyr Leu Asp Asn
1               5                   10                  15

Ser Ser Ile Glu Glu Ala Ser Gly Val Tyr Pro Ile Asp Asp Asp Asp
            20                  25                  30

Tyr Ala Ser Ala Ser Gly Ser Gly Ala Asp Glu Asp Val Glu Ser Pro
        35                  40                  45

Glu Leu Thr Thr Ser Arg Pro Leu Pro Lys Ile Leu Leu Thr Ser Ala
    50                  55                  60

Ala Pro Lys Val Glu Thr Thr Thr Leu Asn Ile Gln Asn Lys Ile Pro
65                  70                  75                  80

Ala Gln Thr Lys Ser Pro Glu Glu Thr Asp Lys Glu Lys Val His Leu
                85                  90                  95

Ser Asp Ser Glu Arg Lys Met Asp Pro Ala Glu Glu Asp Thr Asn Val
            100                 105                 110

Tyr Thr Glu Lys His Ser Asp Ser Leu Phe Lys Arg Thr Glu
        115                 120                 125

<210> SEQ ID NO 3
<211> LENGTH: 3485
<212> TYPE: DNA
<213> ORGANISM: Homo sapiens

<400> SEQUENCE: 3
agtcgcccag gggagcccgg agaagcaggc tcaggaggga gggagccaga ggaaaagaag      60
aggaggagaa ggaggaggac ccggggaggg aggcgcggcg cgggaggagg aggggcgcag     120
ccgcggagcc agtggccccg cttggacgcg ctgctctcca gatacccccg gagctccagc     180
cgcgcggatc gcgcgctccc gccgctctgc cctaaaactt ctgccgtagc tccctttcaa     240
gccagcgaat ttattcctta aaaccagaaa ctgaacctcg gcacgggaaa ggagtccgcg     300
gaggagcaaa accacagcag agcaagaaga gcttcagaga gcagccttcc cggagcacca     360
actccgtgtc gggagtgcag aaaccaacaa gtgagagggc gccgcgttcc cggggcgcag     420
ctgcgggcgg cgggagcagg cgcaggagga ggaagcgagc gccccgagc cccgagcccg      480 agtccccgag cctgagccgc aatcgctgcg gtactctgct ccggattcgt gtgcgcgggc     540
tgcgccgagc gctgggcagg aggcttcgtt ttgccctggt tgcaagcagc ggctgggagc     600
agccggtccc tggggaatat gcggcgcgcg tggatcctgc tcaccttggg cttggtggcc     660
tgcgtgtcgg cggagtcgag agcagagctg acatctgata agacatgta ccttgacaac      720 agctccattg aagaagcttc aggagtgtat cctattgatg acgatgacta cgcttctgcg     780
tctggctcgg gagctgatga ggatgtagag agtccagagc tgacaacatc tcgaccactt     840
ccaaagatac tgttgactag tgctgctcca aaagtggaaa ccacgacgct gaatatacag     900
aacaagatac ctgctcagac aaagtcacct gaagaaactg ataagagaa agttcacctc     960 tctgactcag aaaggaaaat ggacccagcc gaagaggata caaatgtgta tactgagaaa    1020
cactcagaca gtctgtttaa acggacagaa gtcctagcag ctgtcattgc tggtggagtt    1080

```
attggctttc tctttgcaat ttttcttatc ctgctgttgg tgtatcgcat gagaaagaag    1140
gatgaaggaa gctatgacct tggagaacgc aaaccatcca gtgctgctta tcagaaggca    1200
cctactaagg agttttatgc gtaaaactcc aacttagtgt ctctatttat gagatcactg    1260
aacttttcaa aataaagctt ttgcatagaa taatgaagat ctttgttttt tgttttcatt    1320
aaagagccat tctggcactt taatgataaa atcccattgt atttaaaaca tttcatgtat    1380
ttctttagaa caacataaaa ttaaaattta acatctgcag tgttctgtga atagcagtgg    1440
caaaatatta tgttatgaaa accctcgatg ttcatggaat tggtttaaac ttttatgcgc    1500
aaatacaaaa tgattgtctt tttcctatga ctcaaagatg aaagctgttt catttgtgtc    1560
agcatgtctc agattgacct taccaagttg gtcttacttt gttaatttat ctgttgtccc    1620
cttcctctcc tctgccctcc cttcttgtgc ccttaaaacc aaaccctatg ccttttgtag    1680
ctgtcatggt gcaatttgtc tttggaaaat tcagataatg gtaatttagt gtatatgtga    1740
ttttcaaata tgtaaacttt aacttccact ttgtataaat ttttaagtgt cagactatcc    1800
attttacact tgctttattt ttcattacct gtagctttgg gcagatttgc aacagcaaat    1860
taatgtgtaa aattggatta ttactacaaa accgtttagt catatctatc taatcagatc    1920
ttcttttggg aggatttgat gtaagttact gacaagcctc agcaaaccca aagatgttaa    1980
cagtatttta agaagttgct gcagattcct ttggccactg tatttgttaa tttcttgcaa    2040
tttgaaggta cgagtagagg tttaagaaaa atcagttttt tgttcttaaa aatgcattta    2100
agttgtaaac gtcttttttaa gcctttgaag tgcctctgat tctatgtaac ttgttgcaga    2160
ctggtgttaa tgagtatatg taacagttta aaaaaaaagt tggtatttta taagcacaga    2220
caattctaat ggtaactttt gtagtcttat gaatagacat aaattgtaat ttgggaacat    2280
aaaaactact gaataaatca tgtggcctaa tattgaaaat gtcactgtta taaattttgt    2340 acattttga tcaaatgtac atctcccctt tgctaacggc cgtctgctct caaggatgac    2400
gtgggtttga tttctaagtg tttcacagtg tctgtaaatc aagaccaaag agcctgtcga    2460
tgagactgtt tattaccaga ttcacttctg aattggccag aggaaatctg aatgtattat    2520
cctgtgtgtg tctaggtaga gatattggaa ggctgccagg ggatttcgaa gtttgcaacc    2580
tttataggat aactgatggc aatattaaga cagacgcctg cttttgcaaa taacttacaa    2640
gactgtaaat tccaaagatc tgaatggggc tttcctgatg ttggtatcta aggcttaggc    2700
ctatagattg atttaccttt ggaattgtgc tccaaatgtc tactgaagct taaccgaaga    2760
actaataaat ggactacagt agctcacgtt acagggaagg agggtaggca gggaggctct    2820
gtgtgttaaa atgagggtct cactgcttta ggattgaagt ggctggaaag agtgatgcct    2880
ggggaaggag atggagttat gagggtactg tggctggtac tttctgtact aaacatttcc    2940
tttttctatt ttaccactaa ttttgtttta aactgtgagc cgtccaagtc agaagaagac    3000
agcaaaaaaa gcaacttttc caacatacaa tttactttta ataaagtatg aatatttcat    3060
tttgagaaca ttccctggaa ttgccacata attcattaaa acatttttt taagcaacac    3120 ttggaacagt gtttacttta aatccttaat ggccttaatt aattctcaga ttcctgcccc    3180
atcacttaca gaaccaattc actttagagt gactaaaagg aaacgatagc ctagcttttct   3240 aaagccacgc tgtgtccctc aattacagag ggtaggaatg ggtatacctc taactgtgca    3300
aagcagagtg aaattcaatt catagaataa caactgctgg gaatatccgt gccaggaaaa    3360
gaaaaatttc tggcaaatat tttgtcactg ctgtaaagca aaatatttgt gaaagtgcca    3420
aaataaagtc tgtcatgcca aaagtaaatc attgtataga ctgacatcca gttttcttca    3480
``` actgt 3485

<210> SEQ ID NO 4
<211> LENGTH: 79
<212> TYPE: PRT
<213> ORGANISM: Homo sapiens

<400> SEQUENCE: 4

Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu
65                  70                  75

<210> SEQ ID NO 5
<211> LENGTH: 87
<212> TYPE: PRT
<213> ORGANISM: Homo sapiens

<400> SEQUENCE: 5

Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu
                85

<210> SEQ ID NO 6
<211> LENGTH: 100
<212> TYPE: PRT
<213> ORGANISM: Homo sapiens

<400> SEQUENCE: 6

Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Leu Asn Ile Gln Asn Lys
                85                  90                  95

Ile Pro Ala Gln

100

<210> SEQ ID NO 7
<211> LENGTH: 144
<212> TYPE: PRT
<213> ORGANISM: Homo sapiens

<400> SEQUENCE: 7

```
Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
    130                 135                 140
```

<210> SEQ ID NO 8
<211> LENGTH: 169
<212> TYPE: PRT
<213> ORGANISM: Homo sapiens

<400> SEQUENCE: 8

```
Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
    130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr
                165
```

```
<210> SEQ ID NO 9
<211> LENGTH: 71
<212> TYPE: PRT
<213> ORGANISM: Homo sapiens

<400> SEQUENCE: 9

Thr Leu Gly Leu Val Ala Cys Val Ser Ala Glu Ser Arg Ala Glu Leu
1               5                   10                  15

Thr Ser Asp Lys Asp Met Tyr Leu Asp Asn Ser Ser Ile Glu Glu Ala
            20                  25                  30

Ser Gly Val Tyr Pro Ile Asp Asp Asp Tyr Ala Ser Ala Ser Gly
        35                  40                  45

Ser Gly Ala Asp Glu Asp Val Glu Ser Pro Glu Leu Thr Thr Ser Arg
    50                  55                  60

Pro Leu Pro Lys Ile Leu Leu
65                  70

<210> SEQ ID NO 10
<211> LENGTH: 69
<212> TYPE: PRT
<213> ORGANISM: Homo sapiens

<400> SEQUENCE: 10

Glu Ser Arg Ala Glu Leu Thr Ser Asp Lys Asp Met Tyr Leu Asp Asn
1               5                   10                  15

Ser Ser Ile Glu Glu Ala Ser Gly Val Tyr Pro Ile Asp Asp Asp
            20                  25                  30

Tyr Ala Ser Ala Ser Gly Ser Gly Ala Asp Glu Asp Val Glu Ser Pro
        35                  40                  45

Glu Leu Thr Thr Ser Arg Pro Leu Pro Lys Ile Leu Leu Thr Ser Ala
    50                  55                  60

Ala Pro Lys Val Glu
65

<210> SEQ ID NO 11
<211> LENGTH: 82
<212> TYPE: PRT
<213> ORGANISM: Homo sapiens

<400> SEQUENCE: 11

Glu Ser Arg Ala Glu Leu Thr Ser Asp Lys Asp Met Tyr Leu Asp Asn
1               5                   10                  15

Ser Ser Ile Glu Glu Ala Ser Gly Val Tyr Pro Ile Asp Asp Asp
            20                  25                  30

Tyr Ala Ser Ala Ser Gly Ser Gly Ala Asp Glu Asp Val Glu Ser Pro
        35                  40                  45

Glu Leu Thr Thr Ser Arg Pro Leu Pro Lys Ile Leu Leu Thr Ser Ala
    50                  55                  60

Ala Pro Lys Val Glu Thr Thr Thr Leu Asn Ile Gln Asn Lys Ile Pro
65                  70                  75                  80

Ala Gln

<210> SEQ ID NO 12
<211> LENGTH: 151
<212> TYPE: PRT
<213> ORGANISM: Homo sapiens

<400> SEQUENCE: 12

Glu Ser Arg Ala Glu Leu Thr Ser Asp Lys Asp Met Tyr Leu Asp Asn
```

```
1               5                   10                  15
Ser Ser Ile Glu Glu Ala Ser Gly Val Tyr Pro Ile Asp Asp Asp Asp
            20                  25                  30

Tyr Ala Ser Ala Ser Gly Ser Gly Ala Asp Glu Asp Val Glu Ser Pro
            35                  40                  45

Glu Leu Thr Thr Ser Arg Pro Leu Pro Lys Ile Leu Leu Thr Ser Ala
            50                  55                  60

Ala Pro Lys Val Glu Thr Thr Thr Leu Asn Ile Gln Asn Lys Ile Pro
65                  70                  75                  80

Ala Gln Thr Lys Ser Pro Glu Glu Thr Asp Lys Glu Lys Val His Leu
                85                  90                  95

Ser Asp Ser Glu Arg Lys Met Asp Pro Ala Glu Glu Asp Thr Asn Val
                100                 105                 110

Tyr Thr Glu Lys His Ser Asp Ser Leu Phe Lys Arg Thr Glu Val Leu
                115                 120                 125

Ala Ala Val Ile Ala Gly Gly Val Ile Gly Phe Leu Phe Ala Ile Phe
            130                 135                 140

Leu Ile Leu Leu Leu Val Tyr
145                 150

<210> SEQ ID NO 13
<211> LENGTH: 183
<212> TYPE: PRT
<213> ORGANISM: Homo sapiens

<400> SEQUENCE: 13

Glu Ser Arg Ala Glu Leu Thr Ser Asp Lys Asp Met Tyr Leu Asp Asn
1               5                   10                  15

Ser Ser Ile Glu Glu Ala Ser Gly Val Tyr Pro Ile Asp Asp Asp Asp
            20                  25                  30

Tyr Ala Ser Ala Ser Gly Ser Gly Ala Asp Glu Asp Val Glu Ser Pro
            35                  40                  45

Glu Leu Thr Thr Ser Arg Pro Leu Pro Lys Ile Leu Leu Thr Ser Ala
            50                  55                  60

Ala Pro Lys Val Glu Thr Thr Thr Leu Asn Ile Gln Asn Lys Ile Pro
65                  70                  75                  80

Ala Gln Thr Lys Ser Pro Glu Glu Thr Asp Lys Glu Lys Val His Leu
                85                  90                  95

Ser Asp Ser Glu Arg Lys Met Asp Pro Ala Glu Glu Asp Thr Asn Val
                100                 105                 110

Tyr Thr Glu Lys His Ser Asp Ser Leu Phe Lys Arg Thr Glu Val Leu
                115                 120                 125

Ala Ala Val Ile Ala Gly Gly Val Ile Gly Phe Leu Phe Ala Ile Phe
            130                 135                 140

Leu Ile Leu Leu Leu Val Tyr Arg Met Arg Lys Lys Asp Glu Gly Ser
145                 150                 155                 160

Tyr Asp Leu Gly Glu Arg Lys Pro Ser Ser Ala Ala Tyr Gln Lys Ala
                165                 170                 175

Pro Thr Lys Glu Phe Tyr Ala
            180
```